(12) United States Patent
Bassaganya-Riera et al.

(10) Patent No.: US 11,548,885 B2
(45) Date of Patent: Jan. 10, 2023

(54) NLRX1 LIGANDS

(71) Applicant: Landos Biopharma, Inc., Blacksburg, VA (US)

(72) Inventors: Josep Bassaganya-Riera, Blacksburg, VA (US); Andrew Leber, Blacksburg, VA (US); Nuria Tubau-Juni, Blacksburg, VA (US); Raquel Hontecillas, Blacksburg, VA (US)

(73) Assignee: Landos Biopharma, Inc., Blacksburg, VA (US)

( * ) Notice: Subject to any disclaimer, the term of this patent is extended or adjusted under 35 U.S.C. 154(b) by 0 days.

(21) Appl. No.: 17/479,337

(22) Filed: Sep. 20, 2021

(65) Prior Publication Data

US 2022/0089586 A1 Mar. 24, 2022

Related U.S. Application Data

(60) Provisional application No. 63/081,016, filed on Sep. 21, 2020.

(51) Int. Cl.
*C07D 413/14* (2006.01)
*A61P 37/02* (2006.01)

(52) U.S. Cl.
CPC ................ *C07D 413/14* (2013.01)

(58) Field of Classification Search
CPC .. C07D 401/12; C07D 401/06; C07D 403/12; C07D 403/14; C07D 413/14; A61P 37/02; A61P 35/00
See application file for complete search history.

(56) References Cited

U.S. PATENT DOCUMENTS

| | | | |
|---|---|---|---|
| 6,348,433 | B1 | 2/2002 | Jimbo |
| 7,060,705 | B2 | 6/2006 | Fraley |
| 8,143,285 | B2 | 3/2012 | Kugimiya |
| 8,642,609 | B2 | 2/2014 | Makings |
| 2003/0092721 | A1 | 5/2003 | Pitts et al. |
| 2003/0207879 | A1 | 11/2003 | Baraldi et al. |
| 2004/0077667 | A1 | 4/2004 | Matsuoka et al. |
| 2004/0198716 | A1 | 10/2004 | Arad et al. |
| 2009/0053192 | A1 | 2/2009 | Millan et al. |
| 2009/0318479 | A1 | 12/2009 | Denny et al. |
| 2015/0175601 | A1 | 6/2015 | Qian |
| 2015/0202208 | A1 | 7/2015 | Kiyama et al. |

FOREIGN PATENT DOCUMENTS

| | | |
|---|---|---|
| CN | 102838600 A | 12/2012 |
| CN | 109134434 A | 1/2019 |
| EP | 1072952 A1 | 1/2001 |
| EP | 1646615 A1 | 4/2006 |
| EP | 1422218 B1 | 3/2012 |
| EP | 3793979 A1 | 3/2021 |
| JP | 11080110 A | 3/1999 |
| JP | 2000239263 A | 9/2000 |
| WO | WO 98/18466 A2 | 5/1998 |
| WO | WO 98/56376 A1 | 12/1998 |
| WO | WO 2002/48117 A1 | 6/2002 |
| WO | WO 2002/055012 A2 | 7/2002 |
| WO | WO 2007/057782 A2 | 5/2007 |
| WO | WO 2008/153701 A1 | 12/2008 |
| WO | WO 2010/127208 A1 | 11/2010 |
| WO | WO-2012087938 A1 * | 6/2012 ......... A61K 31/7056 |
| WO | WO 2014/087165 A1 | 6/2014 |

OTHER PUBLICATIONS

International Search Report and Written Opinion for PCT Application PCT/US2021/051068 dated Jan. 20, 2022.
Abreu, M.T., Toll-like receptor signalling in the intestinal epithelium: how bacterial recognition shapes intestinal function, Nat Rev Immunol, 2010, 10(2): p. 131-144.
Allen, I.C., C.B. Moore, M. Schneider, Y. Lei, B.K. Davis, M.A. Scull, D. Gris, K.E. Roney, A.G. Zimmermann, J.B. Bowzard, P. Ranjan, K.M. Monroe, R.J. Pickles, S. Sambhara, and J.P. Ting, NLRX1 protein attenuates inflammatory responses to infection by interfering with the RIG-I-MAVS and TRAF6-NF-kappaB signaling pathways. Immunity, 2011, 34(6): p. 854-865.
Amoult, D., F. Soares, I. Tattoli, C. Castanier, D.J. Philpott, and S.E. Girardin, An N-terminal addressing sequence targets NLRX1 to the mitochondrial matrix. J Cell Sci, 2009, 122(Pt 17): p. 3161-3168.
Costford, S.R., I. Tattoli, FT. Duan, A. Volchuk, A. Klip, D.J. Philpott, M. Woo, and S.E. Girardin, Male Mice Lacking NLRX1 Are Partially Protected From High-Fat Diet-Induced Hyperglycemia. J Endocr Soc, 2018, 2(4): p. 336-347.
Coutermarsh-Ott, S., A. Simmons, V. Capria, T. LeRoith, J.E. Wilson, B. Heid, C.W. Philipson, Q. Qin, R. Hontecillas-Magarzo, J. Bassaganya-Riera, J.P. Ting, N. Dervisis, and I.C. Allen, NLRX1 suppresses tumorigenesis and attenuates histiocytic sarcoma through the negative regulation of NF-λB signaling. Oncotarget, 2016, 7(22): p. 33096-33110.
Dattatreya et al., A Brief Review on Immune Mediated Diseases. J Clin Cell Immunol 2011, S11. DOI: 10.4172/2155-9899.S11-001 ISSN:2155-9899 JCCI.
Davis, B.K., C. Philipson, R. Hontecillas, K. Eden, J. Bassaganya-Riera, and I.C. Allen, Emerging significance of NLRs in inflammatory bowel disease. Inflamm Bowel Dis, 2014, 20(12): p. 2412-2432.

(Continued)

*Primary Examiner* — Samira J Jean-Louis
(74) *Attorney, Agent, or Firm* — Daniel A. Blasiole; DeWitt LLP

(57) ABSTRACT

Provided are compounds that target the nucleotide-binding oligomerization domain, leucine rich repeat containing X1 (NLRX1) pathway. The compounds can be used to treat conditions such as autoimmune diseases, allergic diseases, chronic and/or inflammatory central nervous system diseases, chronic and/or inflammatory respiratory diseases, cancer, and infectious diseases. Exemplary conditions include multiple sclerosis, asthma, Alzheimer's disease, Parkinson's disease, neuroinflammation resulting from, for example, stroke, traumatic brain injury, or spinal cord injury, chronic obstructive pulmonary disease, idiopathic pulmonary fibrosis, and inflammatory bowel disease.

29 Claims, 12 Drawing Sheets

(56) References Cited

OTHER PUBLICATIONS

Eitas, T.K., W.C. Chou, H. Wen, D. Gris, G.R. Robbins, J. Brickey, Y. Oyama, and J.P. Ting, The nucleotide-binding leucine-rich repeat (NLR) family member NLRX1 mediates protection against experimental autoimmune encephalomyelitis and represses macrophage/microglia-induced inflammation. J Biol Chem, 2014. 289(7):p. 4173-4179.

Feng, H., E.M. Lenarcic, D. Yamane, E. Wauthier, J. Mo, H. Guo, D.R. McGivern, O. Gonzalez-Lopez, I. Misumi, L.M. Reid, J.K. Whitmire, J.P. Ting, J.A. Duncan, N.J. Moorman, and S.M. Lemon, NLRX1 promotes immediate IRF1-directed antiviral responses by limiting dsRNA-activated translational inhibition mediated by PKR, Nat Immunol, 2017, 18(12): p. 1299-1309.

Guo, H., R. Konig, M. Deng, M. Riess, J. Mo, L. Zhang, A. Petrucelli, S.M. Yoh, B. Barefoot, M. Samo, G.D. Sempowski, A. Zhang, A.M. Colberg-Poley, H. Feng, S.M. Lemon, Y. Liu, Y. Zhang, H. Wen, Z. Zhang, B. Damania, L.C. Tsao, Q. Wang, L. Su, J.A. Duncan, S.K. Chanda, and J.P. Ting, NLRX1 Sequesters STING to Negatively Regulate the Interferon Response, Thereby Facilitating the Replication of HIV-1 and DNA Viruses. Cell Host Microbe, 2016. 19(4): p. 515-528.

Hong, M., S.I. Yoon, and I.A. Wilson, Structure and functional characterization of the RNA-binding element of the NLRX1 innate immune modulator. Immunity, 2012, 36(3): p. 337-347.

Jaworska, J., F. Coulombe, J. Downey, F. Tzelepis, K. Shalaby, I. Tattoli, J. Berube, S. Rousseau, J.G. Martin, S.E. Girardin, J.A. McCullers, and M. Divangahi, NLRX1 prevents mitochondrial induced apoptosis and enhances macrophage antiviral immunity by interacting with influenza virus PB1-F2 protein. Proc Natl Acad Sci USA, 2014, 111(20): p. E2110-2119.

Kale, S.D., T. Ayubi, D. Chung, N. Tubau-Juni, A. Leber, H.X. Dang, S. Karyala, R. Hontecillas, C.B. Lawrence, R.A. Cramer, and J. Bassaganya-Riera, Modulation of Immune Signaling and Metabolism Highlights Host and Fungal Transcriptional Responses in Mouse Models of Invasive Pulmonary Aspergillosis. Sci Rep, 2017. 7(1): p. 17096.

Kang, M.J., C M. Yoon, B.H. Kim, C M. Lee, Y. Zhou, M. Sauler, R. Homer, A. Dhamija, D. Boffa, A.P. West, G.S. Shadel, J.P. Ting, J.R. Tedrow, N. Kaminski, W.J. Kim, C.G. Lee, Y.M. Oh, and J.A. Elias, Suppression of NLRX1 in chronic obstructive pulmonary disease. J Clin Invest, 2015, 125(6): p. 2458-2462.

Kim, J.H., M E. Park, C. Nikapitiya, T.H. Kim, MB. Uddin, H.C. Lee, E. Kim, J.Y. Ma, J.U. Jung, C.J. Kim, and U.S. Lee, FAS-associated factor-1 positively regulates type I interferon response to RNA virus infection by targeting NLRX1. PLoS Pathog, 2017, 13(5): p. e1006398.

Koblansky, A.A., A.D. Truax, R. Liu, S.A. Montgomery, S. Ding, J.E. Wilson, W.J. Brickey, M. Muhlbauer, R.M. McFadden, P. Hu, Z. Li, C. Jobin, P. K. Lund, and J.P. Ting, The Innate Immune Receptor NLRX1 Functions as a Tumor Suppressor by Reducing Colon Tumorigenesis and Key Tumor-Promoting Signals. Cell Rep, 2016, 14(11): p. 2562-2575.

Kors, L., E. Rampanelli, G. Stokman, L .M. Butter, N.M. Held, N. Claessen, P. W.B. Larsen, J. Verheij, C.J. Zuurbier, G. Liebisch, G. Schmitz, S.E. Girardin, S. Florquin, R.H. Houtkooper, and J.C. Leemans, Deletion of NLRX1 increases fatty acid metabolism and prevents diet-induced hepatic steatosis and metabolic syndrome. Biochim Biophys Acta, 2018, 1864(5 Pt A): p. 1883-1895.

Leber, A., R. Hontecillas, N. Tubau-Juni, V. Zoccoli-Rodriguez, M. Hulver, R. McMillan, K. Eden, I.C. Allen, and J. Bassaganya-Riera, NLRX1 Regulates Effector and Metabolic Functions of CD4+ T Cells. J Immunol, 2017.

Leber, A., R. Hontecillas, N. Tubau-Juni, V. Zoccoli-Rodriguez, V. Abedi, and J. Bassaganya-Riera, NLRX1 Modulates Immunometabolic Mechanisms Controlling the Host-Gut Microbiota Interactions during Inflammatory Bowel Disease. Front Immunol, 2018, 9: p. 363.

Lei, Y., B.A. Kansy, J. Li, L. Cong, Y. Liu, S. Trivedi, H. Wen, J.P. Ting, H Ouyang, and R.L. Ferris, EGFR-targeted mAb therapy modulates autophagy in head and neck squamous cell carcinoma through NLRX1-TUFM protein complex. Oncogene, 2016, 35(36): p. 4698-4707.

Li, H., S. Zhang, F. Li, and L. Qin, NLRX1 attenuates apoptosis and inflammatory responses in myocardial ischemia by inhibiting MAVS-dependent NLRP3 inflammasome activation. Mol Immunol, 2016, 76: p. 90-97.

Lu, P., R. Hontecillas, V. Abedi, S. Kale, A. Leber, C. Heltzel, M. Langowski, V. Godfrey, C. Philipson, N. Tubau-Juni, A. Carbo, S. Girardin, A. Uren, and J. Bassaganya-Riera, Modeling-Enabled Characterization of Novel NLRX1 Ligands. PLoS One, 2015, 10(12): p. e0145420.

Ma, Z., S.E. Hopcraft, F. Yang, A. Petrucelli, H. Guo, J.P. Ting, D P. Dittmer, and B. Damania, NLRX1 negatively modulates type I IFN to facilitate KSHV reactivation from latency. PLoS Pathog, 2017, 13(5): p. e1006350.

Moore, C.B., D.T. Bergstralh, J.A. Duncan, Y. Lei, T.E. Morrison, A.G. Zimmermann, M.A. Accavitti-Loper, V.J. Madden, L. Sun, Z. Ye, J.D. Lich, M.T. Heise, Z. Chen, and J.P. Ting, NLRX1 is a regulator of mitochondrial antiviral immunity. Nature, 2008, 451(7178): p. 573-577.

Philipson, C.W., J. Bassaganya-Riera, M. Viladomiu, B. Kronsteiner, V. Abedi, S. Hoops, P. Michalak, L. Kang, S.E. Girardin, and R. Hontecillas, Modeling the Regulatory Mechanisms by Which NLRX1 Modulates Innate Immune Responses to Helicobacter pylori Infection, PLoS One, 2015, 10(9): p. e0137839.

Qin, Y., B. Xue, C. Liu, X. Wang, R. Tian, Q. Xie, M. Guo, G. Li, D. Yang, and H. Zhu, NLRX1 mediates MAVS degradation to attenuate hepatitis C virus-induced innate immune response through PCBP2, J Virol, 2017.

Shurin MR, Smolkin YS. Immune-mediated diseases: where do we stand? Adv Exp Med Biol. 2007;601:3-12.

Singh, K., A. Poteryakhina, A. Zheltukhin, K. Bhatelia, P. Prajapati, L . Sripada, D. Tomar, R. Singh, A.K. Singh, P.M. Chumakov, and R. Singh, NLRX1 acts as tumor suppressor by regulating TNF-alpha induced apoptosis and metabolism in cancer cells. Biochim Biophys Acta, 2015, 1853(5): p. 1073-1086.

Soares, F., I. Tattoli, M.A. Rahman, S.J. Robertson, A. Belcheva, D. Liu, C. Streutker, S. Winer, D.A. Winer, A. Martin, D.J. Philpott, D. Arnoult, and S.E. Girardin, The mitochondrial protein NLRX1 controls the balance between extrinsic and intrinsic apoptosis. J Biol Chem, 2014, 289(28): p. 19317-19330.

Tattoli, I., S.A. Killackey, E.G. Foerster, R. Molinaro, C. Maisonneuve, M.A. Rahman, S. Winer, D.A. Winer, C.J. Streutker, D.J. Philpott, and S.E. Girardin, NLRX1 Acts as an Epithelial-Intrinsic Tumor Suppressor through the Modulation of TNF-Mediated Proliferation, Cell Rep, 2016, 14(11): p. 2576-2586.

Theus, M.H., T. Brickler, A.L. Meza, S. Coutermarsh-Ott, A. Hazy, D. Gris, and I.C. Allen, Loss of NLRX1 Exacerbates Neural Tissue Damage and NF-kappaB Signaling following Brain Injury, J Immunol, 2017, 199(10): p. 3547-3558.

Wang, Y.G., W.L. Fang, J. Wei, T. Wang, N. Wang, J.L. Ma, and M. Shi, The involvement of NLRX1 and NLRP3 in the development of nonalcoholic steatohepatitis in mice. J Chin Med Assoc, 2013, 76(12): p. 686-692.

* cited by examiner

| ID | Structure | Affinity (kcal/mol) |
|---|---|---|
| NX-64-1 | 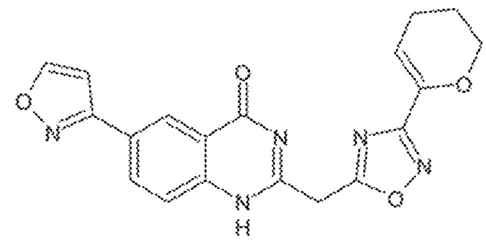 | -10.5 |
| NX-64-2 | 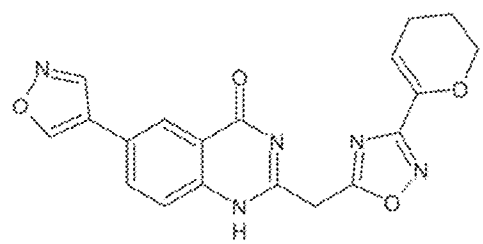 | -9.8 |
| NX-64-3 | 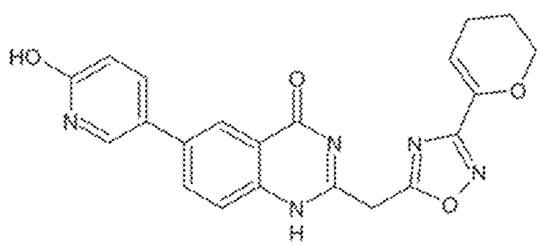 | -10.4 |
| NX-64-4 | 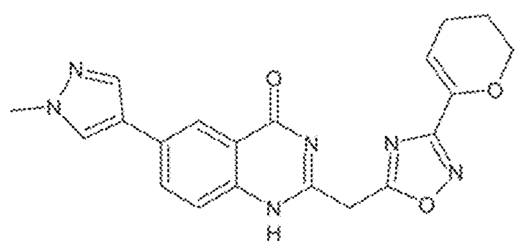 | -9.8 |
| NX-64-5 | 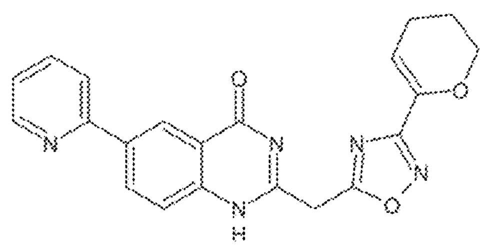 | -10.1 |

| ID | Structure | Affinity (kcal/mol) |
|---|---|---|
| NX-64-6 | 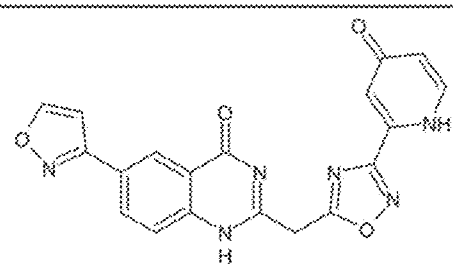 | -9.4 |
| NX-64-7 | 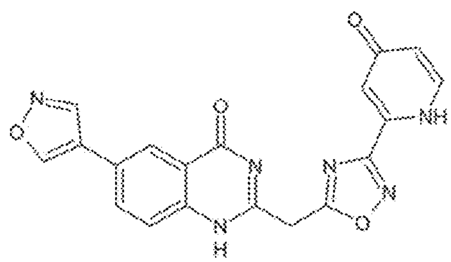 | -9.0 |
| NX-64-8 | 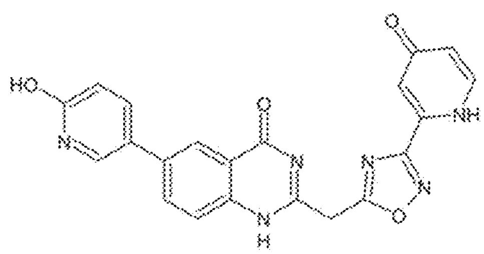 | -9.8 |
| NX-64-9 | 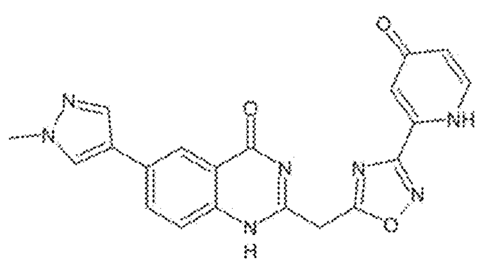 | -9.7 |
| NX-64-10 | 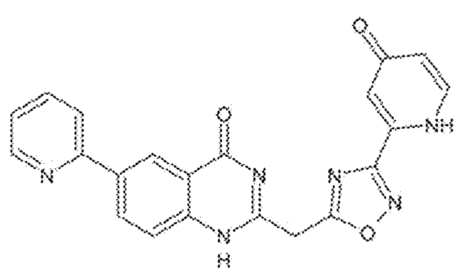 | -9.3 |

FIG. 1B

| ID | Structure | Affinity (kcal/mol) |
|---|---|---|
| NX-64-11 | 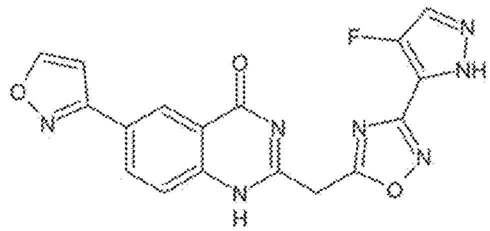 | -9.7 |
| NX-64-12 | 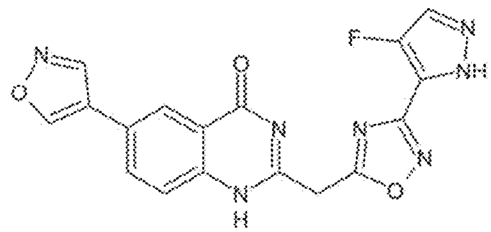 | -9.4 |
| NX-64-13 | 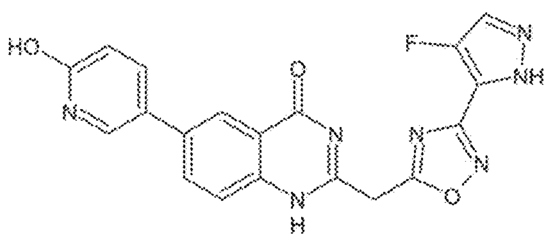 | -10.1 |
| NX-64-14 | 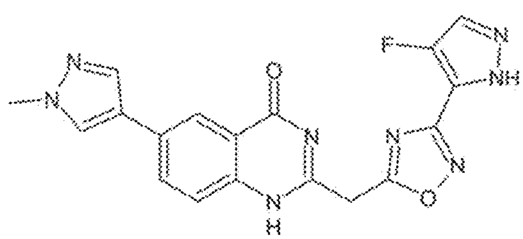 | -8.9 |
| NX-64-15 | 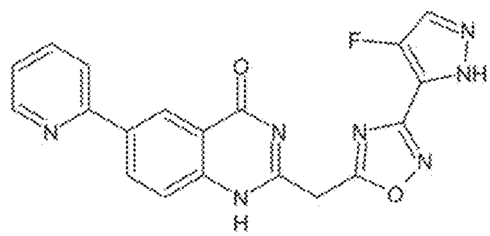 | -9.6 |

| ID | Structure | Affinity (kcal/mol) |
|---|---|---|
| NX-64-16 | 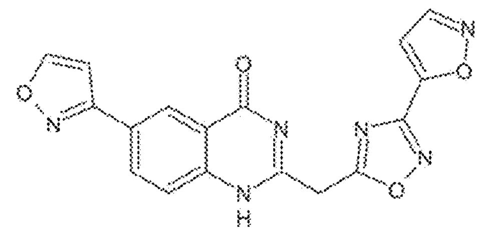 | -9.7 |
| NX-64-17 | 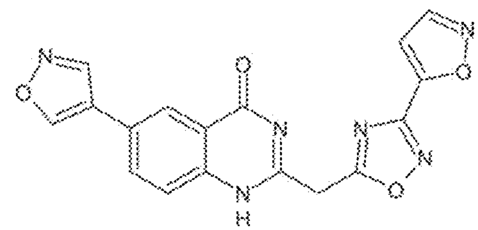 | -9.7 |
| NX-64-18 | 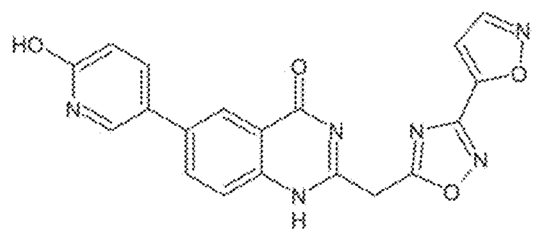 | -9.8 |
| NX-64-19 | 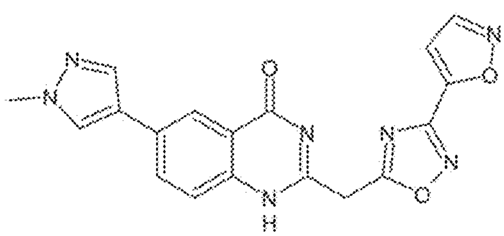 | -9.4 |
| NX-64-20 | 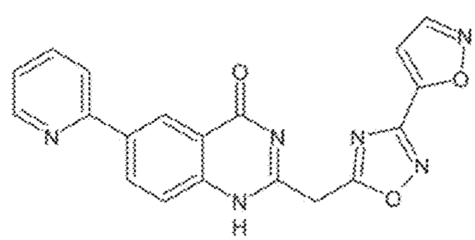 | -9.3 |

| ID | Structure | Affinity (kcal/mol) |
|---|---|---|
| NX-64-21 | 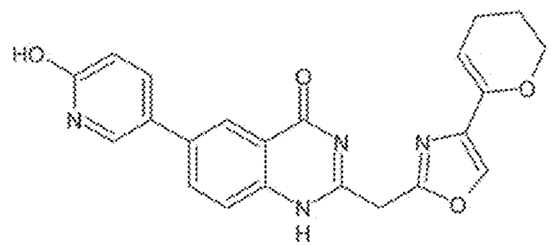 | -8.7 |
| NX-64-22 | 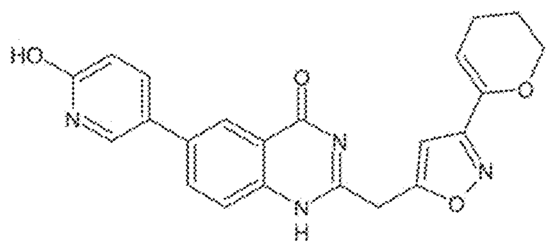 | -9.1 |
| NX-64-23 | 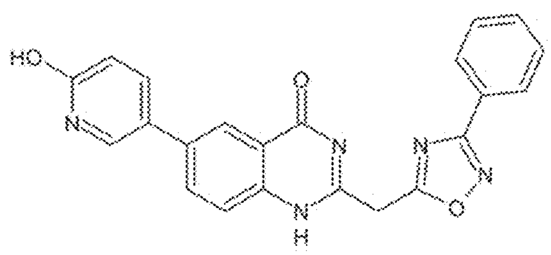 | -9.3 |
| NX-64-24 | 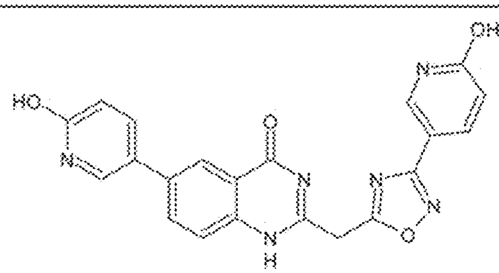 | -8.8 |
| NX-64-25 | 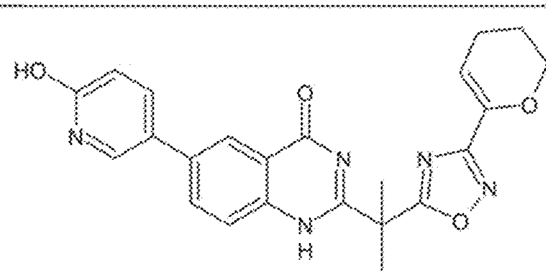 | -10.1 |

FIG. 1E

| ID | Structure | Affinity (kcal/mol) |
|---|---|---|
| NX-64-26 | 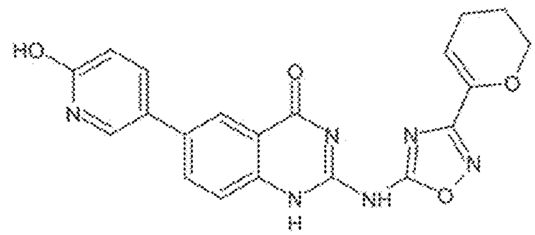 | -8.8 |
| NX-64-27 | 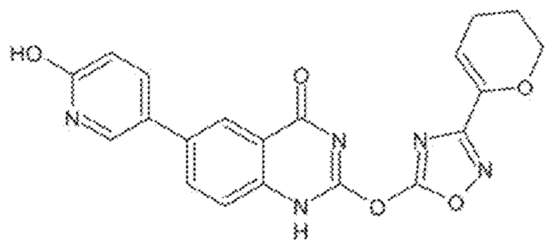 | -9.5 |
| NX-64-28 | 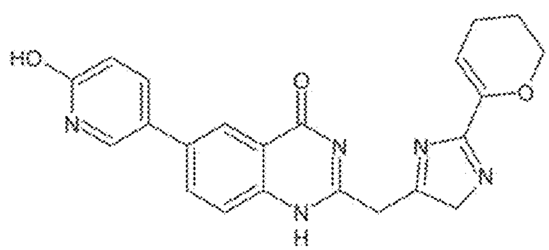 | -9.3 |
| NX-64-29 | 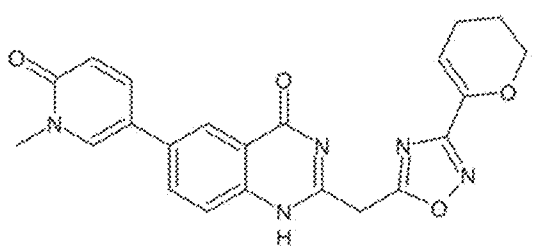 | -9.5 |
| NX-64-30 | 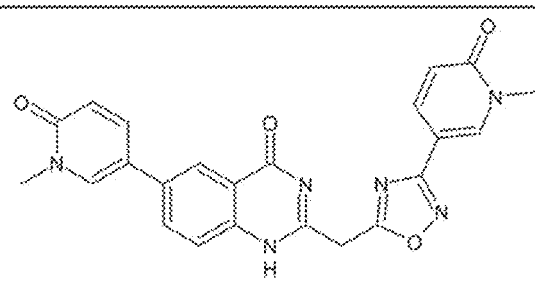 | -9.1 |

NLRX1 LIGANDS

FIELD OF THE INVENTION

The present invention relates to ligands of nucleotide-binding oligomerization domain, leucine rich repeat containing X1 (NLRX1) and methods of treating diseases and disorders with same.

BACKGROUND

Nucleotide-binding oligomerization domain, leucine rich repeat containing X1 (NLRX1) (also called "NOD-like receptor X1" or "NLR family member X1" or "NOD9") is a signaling pathway protein that is expressed in immune cells, the gastrointestinal tract, and skin, lung, muscle, endocrine, and reproductive tissues (Davis et al. 2014). The NLRX1 molecule has three distinct domains and localizes to the mitochondria (Arnoult et al. 2009).

Published results indicate that the loss of NLRX1 worsens disease severity and alters immune cell metabolism (Leber et al. 2017) in models of inflammatory bowel disease (Leber et al. 2018, Lu et al. 2015, Soares et al. 2014). The NLRX1 protein has also been implicated in models of viral responses (Allen et al. 2011, Feng et al. 2017, Guo et al. 2016, Jaworska et al. 2014, Kim et al. 2017, Ma et al. 2017, Moore et al. 2008, Qin et al. 2017), bacterial infection (Philipson et al. 2015), fungal infection (Kale et al. 2017), cancer (Coutermarsh-Ott et al. 2016, Koblansky et al. 2016, Lei et al. 2016, Lei et al. 2016, Singh et al. 2015, Tattoli et al. 2016), hepatic steatosis (Kors et al. 2018, Wang et al. 2013), type 2 diabetes (Costford et al. 2018), brain injury (Theus et al. 2017), myocardial ischemia (Li et al. 2016), chronic obstructive pulmonary disease (Kang et al. 2015), and autoimmune encephalomyelitis (Eitas et al. 2014).

There are clear clinical needs for safe, efficacious treatments for diseases in which NLRX1 is implicated. These include autoimmune diseases, inflammatory and degenerative central nervous system (CNS) diseases, such as Alzheimer's disease, cancers, and infectious diseases. Viral nucleic acids (Hong et al. 2012) and dietary lipids have been identified as natural ligands of NLRX1 (Lu et al. 2015). There is a need to develop novel ligands of the NLRX1 pathway to allow treatments to be tailored specifically to individual diseases and to potentially maximize their efficacy.

The present invention provides compounds that bind to the NLRX1 protein and thus induce a beneficial response in various disease conditions, including but not limited to autoimmune diseases, allergic diseases, chronic and/or inflammatory central nervous system diseases, chronic and/or inflammatory respiratory diseases, cancer, and infectious diseases, such as multiple sclerosis, asthma, Alzheimer's disease, Parkinson's disease, neuroinflammation chronic obstructive pulmonary disease, idiopathic pulmonary fibrosis, and inflammatory bowel disease.

SUMMARY OF THE INVENTION

The invention provides compounds of Formula (I) having an A ring, a B ring, a C ring, a D ring, and an E ring:

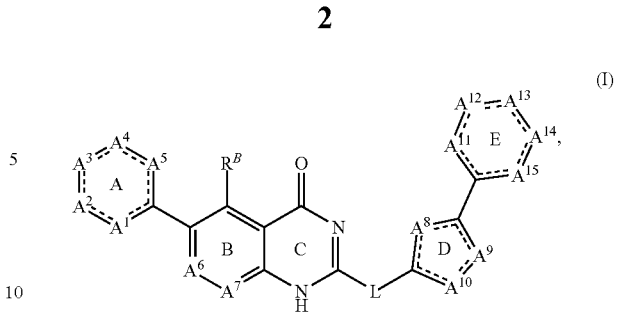

or a salt or ester thereof, wherein:

$A^1$ and $A^5$ are each independently O, $N(R^A)$, $N(R^{ALK})$, $C(R^A)_2$, $C(R^A)$, or N;

$A^2$, $A^3$, and $A^4$ are each independently O, $N(R^A)$, $N(R^{ALK})$, $C(R^A)_2$, $C(R^A)$, N, $C(R^A)(R^O)$, $C(R^O)$, or $C(=O)$, with the proviso that $A^4$ is optionally absent;

$A^6$ and $A^7$ are each independently $C(R^A)$ or N;

$A^8$, $A^9$, and $A^{10}$ are each independently O, $N(R^A)$, $N(R^{ALK})$, $C(R^A)_2$, $C(R^A)$, or N;

$A^{11}$, $A^{12}$, $A^{13}$, $A^{14}$, and $A^{15}$ are each independently O, $N(R^A)$, $N(R^{ALK})$, $C(R^A)_2$, $C(R^A)$, N, $C(R^A)(R^O)$, $C(R^O)$, or $C(=O)$, with the proviso that $A^{14}$ is optionally absent;

each - - - between adjacent atoms represents a bond that is present or absent;

L is O, $N(R^L)$, or $C(R^L)_2$;

$R^O$ in each instance is independently hydroxyl or optionally substituted alkyloxy;

$R^{ALK}$ in each instance is independently C1-C6 alkyl;

$R^A$, $R^B$, and $R^L$ in each instance is independently, hydrogen, halogen, optionally substituted alkyl, optionally substituted alkenyl, optionally substituted alkynyl, optionally substituted cycloalkyl, optionally substituted cycloalkenyl, hydroxyl, carboxyl, optionally substituted alkyloxy, optionally substituted alkenyloxy, optionally substituted alkynyloxy, optionally substituted cycloalkyloxy, optionally substituted cycloalkenyloxy, mercapto, optionally substituted alkylthio, optionally substituted alkenylthio, optionally substituted alkynylthio, optionally substituted alkylsulfinyl, optionally substituted alkylsulfonyl, optionally substituted alkylsulfonyloxy, optionally substituted cycloalkylthio, optionally substituted cycloalkylsulfinyl, optionally substituted cycloalkylsulfonyl, optionally substituted cycloalkylsulfonyloxy, optionally substituted cycloalkenylthio, optionally substituted cycloalkenylsulfinyl, optionally substituted cycloalkenylsulfonyl, optionally substituted cycloalkenylsulfonyloxy, optionally substituted amino, acyl, optionally substituted alkyloxycarbonyl, optionally substituted alkenyloxycarbonyl, optionally substituted alkynyloxycarbonyl, optionally substituted aryloxycarbonyl, optionally substituted carbamoyl, optionally substituted sulfamoyl, cyano, nitro, optionally substituted aryl, optionally substituted aryloxy, optionally substituted arylthio, optionally substituted arylsulfinyl, optionally substituted arylsulfonyl, optionally substituted arylsulfonyloxy, optionally substituted heteroaryl, optionally substituted heteroaryloxy, optionally substituted heteroarylthio, optionally substituted heteroarylsulfinyl, optionally substituted heteroarylsulfonyl, optionally substituted heteroarylsulfonyloxy, or an optionally substituted non-aromatic heterocyclic group.

In some versions, $A^1$ is O. In some versions, $A^1$ is $N(R^A)$. In some versions, $A^1$ is $N(R^{ALK})$. In some versions, $A^1$ is $C(R^A)_2$. In some versions, $A^1$ is $C(R^A)$. In some versions, $A^1$ is N. In some versions, each $R^A$ of $A^1$ is hydrogen or halogen. In some versions, each $R^A$ of $A^1$ is hydrogen.

In some versions, $A^2$ is O. In some versions, $A^2$ is $N(R^A)$. In some versions, $A^2$ is $N(R^{ALK})$. In some versions, $A^2$ is $C(R^A)_2$. In some versions, $A^2$ is $C(R^A)$. In some versions, $A^2$ is N. In some versions, $A^2$ is $C(R^A)(R^O)$. In some versions, $A^2$ is $C(R^O)$. In some versions, $A^2$ is $C(=O)$. In some versions, each $R^A$ of $A^2$ is hydrogen or halogen. In some versions, each $R^A$ of $A^2$ is hydrogen. In some versions, each $R^O$ of $A^2$ is hydroxyl.

In some versions, $A^3$ is O. In some versions, $A^3$ is $N(R^A)$. In some versions, $A^3$ is $N(R^{ALK})$. In some versions, $A^3$ is $C(R^A)_2$. In some versions, $A^3$ is $C(R^A)$. In some versions, $A^3$ is N. In some versions, $A^3$ is $C(R^A)(R^O)$. In some versions, $A^3$ is $C(R^O)$. In some versions, $A^3$ is $C(=O)$. In some versions, each $R^A$ of $A^3$ is hydrogen or halogen. In some versions, each $R^A$ of $A^3$ is hydrogen. In some versions, each $R^O$ of $A^3$ is hydroxyl.

In some versions, $A^4$ is O. In some versions, $A^4$ is $N(R^A)$. In some versions, $A^4$ is $N(R^{ALK})$. In some versions, $A^4$ is $C(R^A)_2$. In some versions, $A^4$ is $C(R^A)$. In some versions, $A^4$ is N. In some versions, $A^4$ is $C(R^A)(R^O)$. In some versions, $A^4$ is $C(R^O)$. In some versions, $A^4$ is $C(=O)$. In some versions, each $R^A$ of $A^4$ is hydrogen or halogen. In some versions, each $R^A$ of $A^4$ is hydrogen. In some versions, each $R^O$ of $A^4$ is hydroxyl. In some versions, $A^4$ is absent.

In some versions, $A^5$ is O. In some versions, $A^5$ is $N(R^A)$. In some versions, $A^5$ is $N(R^{ALK})$. In some versions, $A^5$ is $C(R^A)_2$. In some versions, $A^5$ is $C(R^A)$. In some versions, $A^5$ is N. In some versions, each $R^A$ of $A^5$ is hydrogen or halogen. In some versions, each $R^A$ of $A^5$ is hydrogen.

In some versions, $A^6$ is $C(R^A)$. In some versions, $A^6$ is N. In some versions, $A^7$ is $C(R^A)$. In some versions, $A^7$ is N. In some versions, one of $A^6$ and $A^7$ is $C(R^A)$. In some versions, one of $A^6$ and $A^7$ is N. In some versions, one of $A^6$ and $A^7$ is $C(R^A)$ and the other of $A^6$ and $A^7$ is N. In some versions, both of $A^6$ and $A^7$ is $C(R^A)$. In some versions, each $R^A$ of $A^6$ is hydrogen or halogen. In some versions, each $R^A$ of $A^6$ is hydrogen. In some versions, each $R^A$ of $A^7$ is hydrogen or halogen. In some versions, each $R^A$ of $A^7$ is hydrogen.

In some versions, $A^8$ is O. In some versions, $A^8$ is $N(R^A)$. In some versions, $A^8$ is $N(R^{ALK})$. In some versions, $A^8$ is $C(R^A)_2$. In some versions, $A^8$ is $C(R^A)$. In some versions, $A^8$ is N. In some versions, each $R^A$ of $A^8$ is hydrogen or halogen. In some versions, each $R^A$ of $A^8$ is hydrogen.

In some versions, $A^9$ is O. In some versions, $A^9$ is $N(R^A)$. In some versions, $A^9$ is $N(R^{ALK})$. In some versions, $A^9$ is $C(R^A)_2$. In some versions, $A^9$ is $C(R^A)$. In some versions, $A^9$ is N. In some versions, each $R^A$ of $A^9$ is hydrogen or halogen. In some versions, each $R^A$ of $A^9$ is hydrogen.

In some versions, $A^{10}$ is O. In some versions, $A^{10}$ is $N(R^A)$. In some versions, $A^{10}$ is $N(R^{ALK})$. In some versions, $A^{10}$ is $C(R^A)_2$. In some versions, $A^{10}$ is $C(R^A)$. In some versions, $A^{10}$ is N. In some versions, each $R^A$ of $A^{10}$ is hydrogen or halogen. In some versions, each $R^A$ of $A^{10}$ is hydrogen.

In some versions, $A^{11}$ is O. In some versions, $A^{11}$ is $N(R^A)$. In some versions, $A^{11}$ is $N(R^{ALK})$. In some versions, $A^{11}$ is $C(R^A)_2$. In some versions, $A^{11}$ is $C(R^A)$. In some versions, $A^{11}$ is N. In some versions, $A^{11}$ is $C(R^A)(R^O)$. In some versions, $A^{11}$ is $C(R^O)$. In some versions, $A^{11}$ is $C(=O)$. In some versions, each $R^A$ of $A^{11}$ is hydrogen or halogen. In some versions, each $R^A$ of $A^{11}$ is hydrogen. In some versions, each $R^O$ of $A^{11}$ is hydroxyl.

In some versions, $A^{12}$ is O. In some versions, $A^{12}$ is $N(R^A)$. In some versions, $A^{12}$ is $N(R^{ALK})$. In some versions, $A^{12}$ is $C(R^A)_2$. In some versions, $A^{12}$ is $C(R^A)$. In some versions, $A^{12}$ is N. In some versions, $A^{12}$ is $C(R^A)(R^O)$. In some versions, $A^{12}$ is $C(R^O)$. In some versions, $A^{12}$ is $C(=O)$. In some versions, each $R^A$ of $A^{12}$ is hydrogen or halogen. In some versions, each $R^A$ of $A^{12}$ is hydrogen. In some versions, each $R^O$ of $A^{12}$ is hydroxyl.

In some versions, $A^{13}$ is O. In some versions, $A^{13}$ is $N(R^A)$. In some versions, $A^{13}$ is $N(R^{ALK})$. In some versions, $A^{13}$ is $C(R^A)_2$. In some versions, $A^{13}$ is $C(R^A)$. In some versions, $A^{13}$ is N. In some versions, $A^{13}$ is $C(R^A)(R^O)$. In some versions, $A^{13}$ is $C(R^O)$. In some versions, $A^{13}$ is $C(=O)$. In some versions, each $R^A$ of $A^{13}$ is hydrogen or halogen. In some versions, each $R^A$ of $A^{13}$ is hydrogen. In some versions, each $R^O$ of $A^{13}$ is hydroxyl.

In some versions, $A^{14}$ is O. In some versions, $A^{14}$ is $N(R^A)$. In some versions, $A^{14}$ is $N(R^{ALK})$. In some versions, $A^{14}$ is $C(R^A)_2$. In some versions, $A^{14}$ is $C(R^A)$. In some versions, $A^{14}$ is N. In some versions, $A^{14}$ is $C(R^A)(R^O)$. In some versions, $A^{14}$ is $C(R^O)$. In some versions, $A^{14}$ is $C(=O)$. In some versions, each $R^A$ of $A^{14}$ is hydrogen or halogen. In some versions, each $R^A$ of $A^{14}$ is hydrogen. In some versions, each $R^O$ of $A^{14}$ is hydroxyl. In some versions, $A^{14}$ is absent.

In some versions, $A^{15}$ is O. In some versions, $A^{15}$ is $N(R^A)$. In some versions, $A^{15}$ is $N(R^{ALK})$. In some versions, $A^{15}$ is $C(R^A)_2$. In some versions, $A^{15}$ is $C(R^A)$. In some versions, $A^{15}$ is N. In some versions, $A^{15}$ is $C(R^A)(R^O)$. In some versions, $A^{15}$ is $C(R^O)$. In some versions, $A^{15}$ is $C(=O)$. In some versions, each $R^A$ of $A^{15}$ is hydrogen or halogen. In some versions, each $R^A$ of $A^{15}$ is hydrogen. In some versions, each $R^O$ of $A^{15}$ is hydroxyl.

In some versions, L is O. In some versions, L is $N(R^L)$. In some versions, L is $C(R^L)_2$. In some versions, each $R^L$ of $A^{15}$ is hydrogen or halogen. In some versions, each $R^L$ of $A^{15}$ is hydrogen. In some versions, In some versions, at least one $R^L$ of $A^{15}$ is alkyl. In some versions, each $R^L$ of $A^{15}$ is alkyl.

In some versions, $R^A$ in each instance is independently hydrogen, halogen, optionally substituted C1-C6 alkyl, hydroxyl, carboxyl, optionally substituted cycloalkyl, optionally substituted C1-C6 alkyloxy, optionally substituted amino, acyl, optionally substituted alkyloxycarbonyl, optionally substituted aryl, optionally substituted heteroaryl, or optionally substituted non-aromatic heterocyclic group. In some versions, $R^A$ in each instance is independently hydrogen, halogen, unsubstituted C1-C6 alkyl, hydroxyl, carboxyl, unsubstituted cycloalkyl, unsubstituted C1-C6 alkyloxy, unsubstituted amino, acyl, unsubstituted alkyloxycarbonyl, unsubstituted aryl, unsubstituted heteroaryl, or unsubstituted non-aromatic heterocyclic group. In some versions, $R^A$ in each instance is hydrogen or halogen. In some versions, $R^A$ in each instance is hydrogen.

In some versions, $R^B$ in each instance is independently hydrogen, halogen, optionally substituted C1-C6 alkyl, hydroxyl, carboxyl, optionally substituted cycloalkyl, optionally substituted C1-C6 alkyloxy, optionally substituted amino, acyl, optionally substituted alkyloxycarbonyl, optionally substituted aryl, optionally substituted heteroaryl, or optionally substituted non-aromatic heterocyclic group. In some versions, $R^B$ in each instance is independently hydrogen, halogen, unsubstituted C1-C6 alkyl, hydroxyl, carboxyl, unsubstituted cycloalkyl, unsubstituted C1-C6 alkyloxy, unsubstituted amino, acyl, unsubstituted alkyloxycarbonyl, unsubstituted aryl, unsubstituted heteroaryl, or unsubstituted non-aromatic heterocyclic group. In some versions, $R^B$ in each instance is hydrogen or halogen. In some versions, $R^B$ in each instance is hydrogen.

In some versions, $R^L$ in each instance is independently hydrogen, halogen, optionally substituted C1-C6 alkyl, hydroxyl, carboxyl, optionally substituted cycloalkyl, optionally substituted C1-C6 alkyloxy, optionally substituted amino, acyl, optionally substituted alkyloxycarbonyl, optionally substituted aryl, optionally substituted heteroaryl, or optionally substituted non-aromatic heterocyclic group. In some versions, $R^L$ in each instance is independently hydrogen, halogen, unsubstituted C1-C6 alkyl, hydroxyl, carboxyl, unsubstituted cycloalkyl, unsubstituted C1-C6 alkyloxy, unsubstituted amino, acyl, unsubstituted alkyloxycarbonyl, unsubstituted aryl, unsubstituted heteroaryl, or unsubstituted non-aromatic heterocyclic group. In some versions, $R^L$ in each instance is hydrogen or halogen. In some versions, $R^L$ in each instance is hydrogen.

In some versions, Ring A is aromatic. In some versions, Ring D is aromatic. In some versions, Ring E is aromatic.

In some versions, $A^{14}$ is present and $A^{11}$ is $C(R^4)$. In some versions, $A^{14}$ is present and $A^{11}$, $A^{13}$, and $A^{14}$, are each $C(R^4)$.

In some versions:

each optionally substituted alkyl, optionally substituted alkyloxy, optionally substituted alkylthio, optionally substituted alkylsulfinyl, optionally substituted alkylsulfonyl, optionally substituted alkylsulfonyloxy, and optionally substituted alkyloxycarbonyl, when substituted, is independently substituted with one to three substituent(s) selected from the group consisting of cycloalkyl, alkylene optionally containing one or two heteroatom(s), hydroxy, oxo, alkyloxy optionally substituted with a substituent group A at one to three position(s), mercapto, alkylthio, a halogen atom, nitro, cyano, carboxy, alkyloxycarbonyl, optionally substituted amino, optionally substituted carbamoyl, acyl, aryl optionally substituted with a substituent group B at one to three position(s), heteroaryl optionally substituted with a substituent group C at one to three position(s), an optionally substituted non-aromatic heterocyclic ring group optionally substituted with a substituent group C at one to three position(s), aryloxy optionally substituted with a substituent group B at one to three position(s), and alkylsulfonyl; each optionally substituted alkenyl, optionally substituted alkynyl, optionally substituted alkenyloxy, optionally substituted alkynyloxy, optionally substituted alkenylthio, optionally substituted alkynylthio, optionally substituted alkenyloxycarbonyl, optionally substituted alkynyloxy carbonyl, optionally substituted cycloalkyl, optionally substituted cycloalkenyl, optionally substituted cycloalkyloxy, optionally substituted cycloalkenyloxy, optionally substituted cycloalkylthio, optionally substituted cycloalkenylthio, optionally substituted cycloalkylsulfinyl, optionally substituted cycloalkenylsulfinyl, optionally substituted cycloalkylsulfonyl, optionally substituted cycloalkenylsulfonyl, optionally substituted cycloalkylsulfonyloxy, optionally substituted cycloalkenylsulfonyloxy, and optionally substituted alkylene optionally containing one or two heteroatom(s), when substituted, is independently substituted with one or more substituent(s) selected from the group consisting of alkyl optionally substituted with a substituent group D at one to three position(s), cycloalkyl, hydroxy, oxo, alkyloxy optionally substituted with a substituent group A at one to three position(s), mercapto, alkylthio, a halogen atom, nitro, cyano, carboxy, alkyloxycarbonyl, optionally substituted amino, optionally substituted carbamoyl, acyl, acyloxy, aryl optionally substituted with a substituent group B at one to three position(s), heteroaryl optionally substituted with a substituent group C at one to three position(s), non-aromatic heterocyclic group optionally substituted with a substituent group C at one to three position(s), aryloxy optionally substituted with a substituent group C at one to three position(s), and alkylsulfonyl;

each optionally substituted aryl, optionally substituted aryloxy, optionally substituted aryloxycarbonyl, optionally substituted arylthio, optionally substituted arylsulfinyl, optionally substituted arylsulfonyl, optionally substituted arylsulfonyloxy, optionally substituted heteroaryl, optionally substituted heteroaryloxy, optionally substituted heteroarylthio, optionally substituted heteroarylsulfinyl, optionally substituted heteroarylsulfonyl, optionally substituted heteroarylsulfonyloxy, and optionally substituted non-aromatic heterocyclic group, when substituted, are each independently substituted with one or more substituent(s) selected from the group consisting of alkyl optionally substituted with a substituent group D at one to three position(s), oxo, cycloalkyl, alkenyl, alkynyl, hydroxy, alkyloxy optionally substituted with a substituent group A at one to three position(s), aryloxy optionally substituted with a substituent group B at one to three position(s), mercapto, alkylthio, a halogen atom, nitro, cyano, carboxy, alkyloxycarbonyl, acyl, alkylsulfonyl, optionally substituted amino, optionally substituted carbamoyl, aryl optionally substituted with a substituent group B at one to three position(s), heteroaryl optionally substituted with a substituent group C at one to three position(s), and non-aromatic heterocyclic group optionally substituted with a substituent group C at one to three position(s);

each optionally substituted amino, optionally substituted carbamoyl, and optionally substituted sulfamoyl, when substituted, is independently substituted with one or two substituent(s) selected from the group consisting of alkyl, alkenyl, alkynyl, cycloalkyl, cycloalkynyl, aryl, heteroaryl, acyl, alkyloxycarbonyl, alkenyloxycarbonyl, alkynyloxycarbonyl, alkyl sulfonyl, alkenylsulfonyl, alkynylsulfonyl, arylsulfonyl, and heteroaryl sulfonyl;

each substituent group A is independently selected from the group consisting of a halogen atom and phenyl optionally substituted with one to three substituent(s) selected from substituent group B;

each substituent group B is independently selected from the group consisting of a halogen atom, alkyl, alkyloxy, cyano, and nitro;

each substituent group C is independently selected from the group consisting of a halogen atom and alkyl; and each substituent group D is independently selected from the group consisting of a halogen atom and alkyloxy.

The compounds of Formula I provided herein are ligands of NLRX1.

Exemplary compounds are shown in FIGS. 1A-1F and 2A-2E. These include NX-64-1, NX-64-2, NX-64-3, NX-64-4, NX-64-5, NX-64-6, NX-64-7, NX-64-8, NX-64-9, NX-64-10, NX-64-11, NX-64-12, NX-64-13, NX-64-14, NX-64-15, NX-64-16, NX-64-17, NX-64-18, NX-64-19, NX-64-20, NX-64-21, NX-64-22, NX-64-23, NX-64-24, NX-64-25, NX-64-26, NX-64-27, NX-64-28, NX-64-29, and NX-64-30:

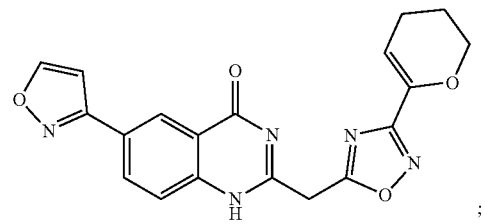

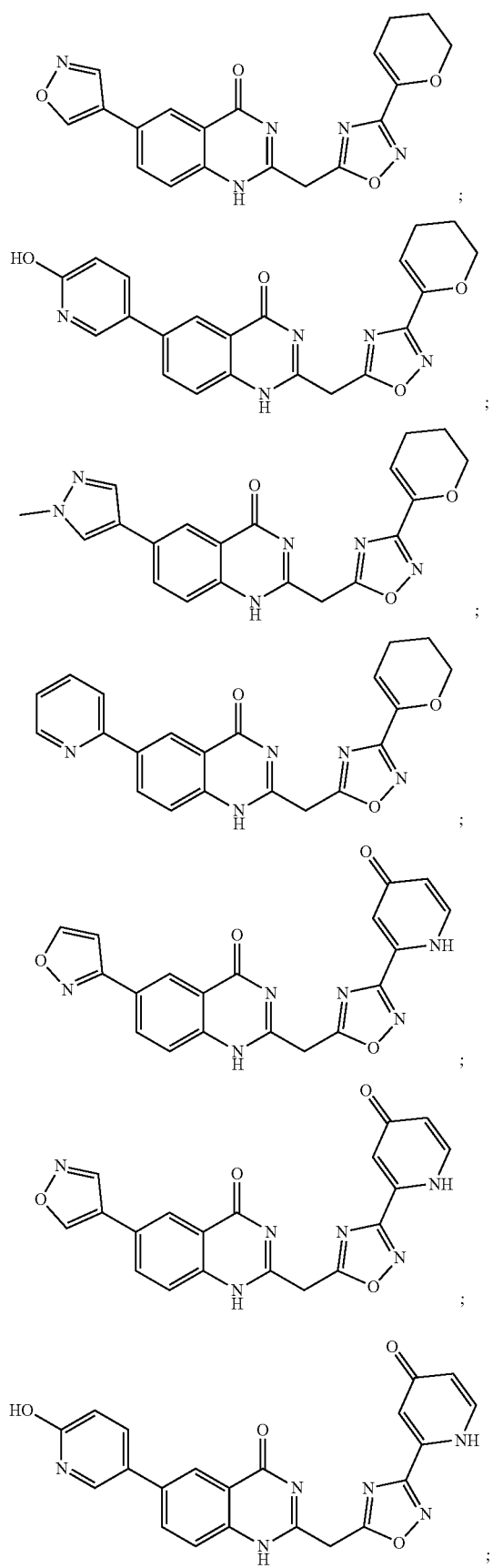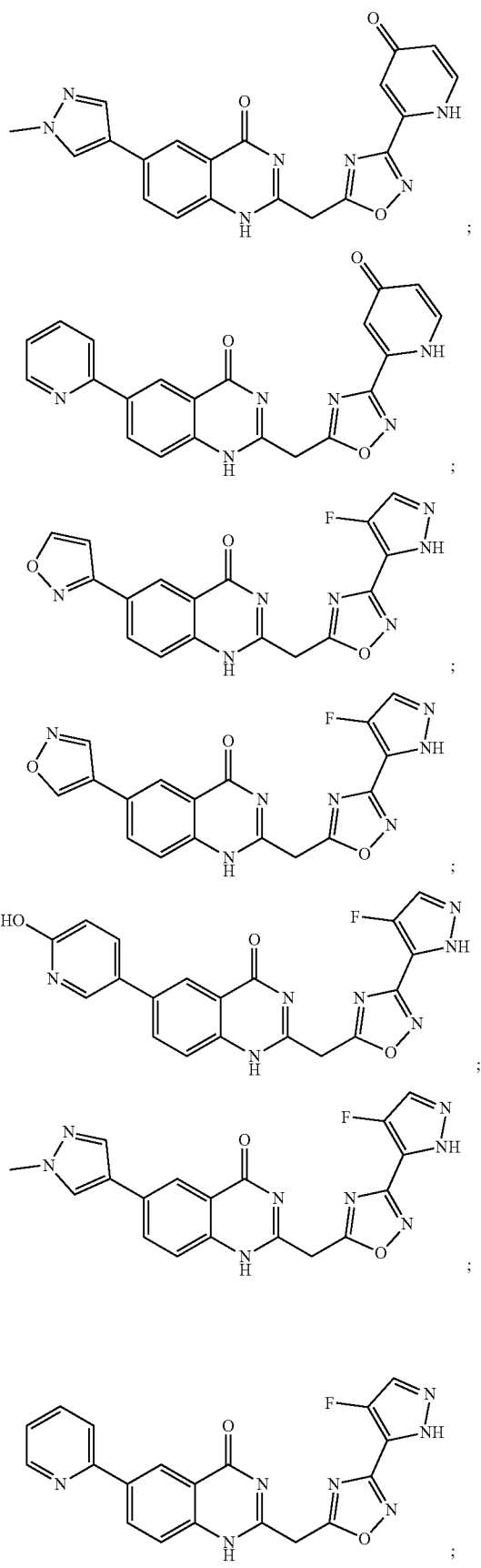

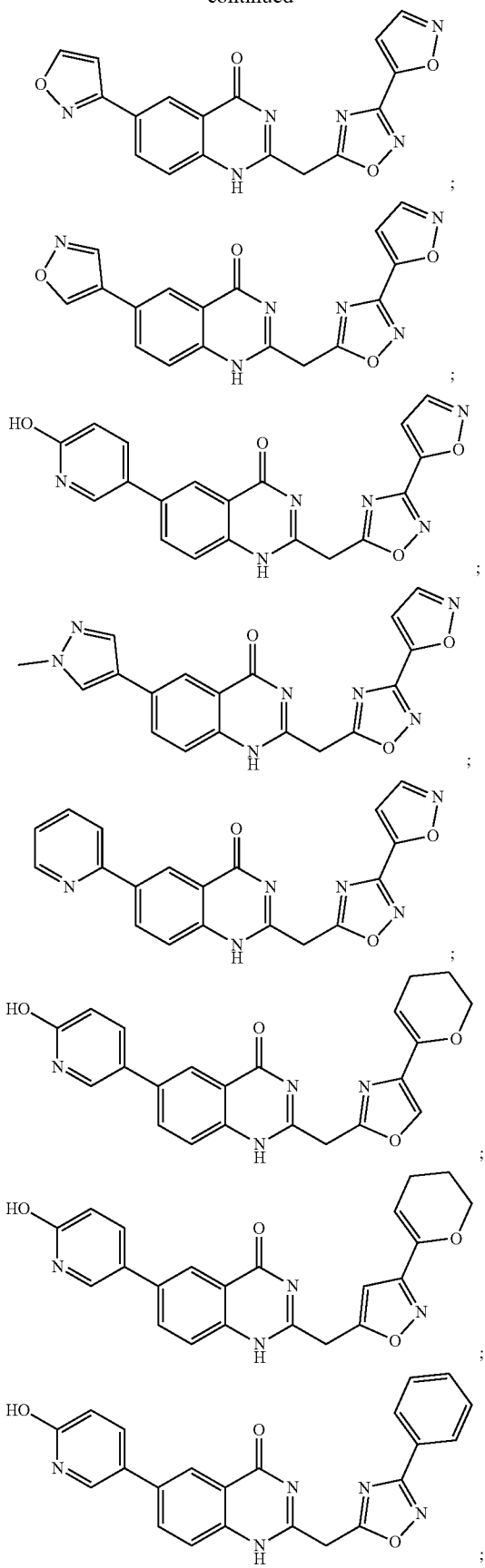
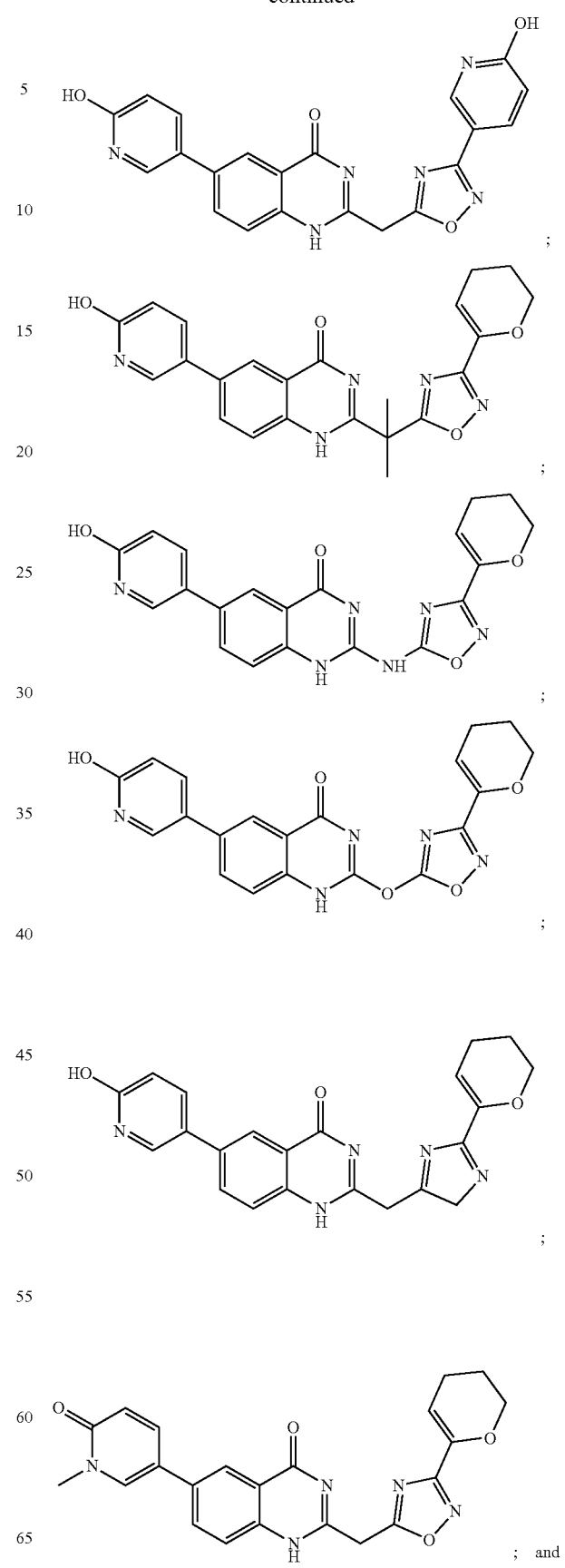

-continued

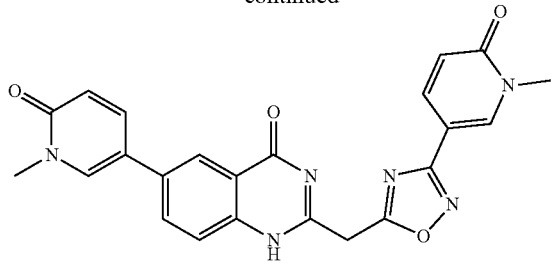

The invention also provides methods of treating a condition in an animal with a compound as described herein. The methods comprise administering an effective amount of the compound to the animal. The condition may be selected from the group consisting of an autoimmune disease, an allergic disease, a chronic and/or inflammatory central nervous system disease, a chronic and/or inflammatory respiratory disease, cancer, and an infectious disease. Exemplary conditions comprise multiple sclerosis, asthma, Alzheimer's disease, Parkinson's disease, neuroinflammation (e.g., such as neuroinflammation resulting from stroke, traumatic brain injury, or spinal cord injury), chronic obstructive pulmonary disease, idiopathic pulmonary fibrosis, or inflammatory bowel disease.

The objects and advantages of the invention will appear more fully from the following detailed description of the preferred embodiment of the invention made in conjunction with the accompanying drawings.

BRIEF DESCRIPTION OF THE DRAWINGS

FIGS. 1A-1F. Computational prediction of binding of selected compounds to NLRX1 in kcal/mol.

DETAILED DESCRIPTION OF THE INVENTION

Figure 1A:
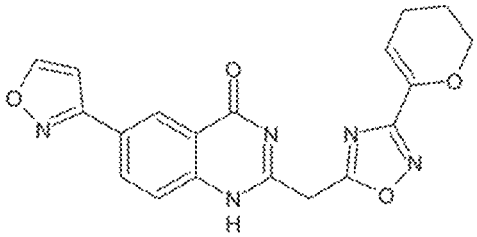
Figure 1A:
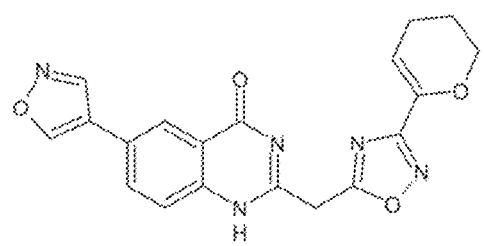
Figure 1A:
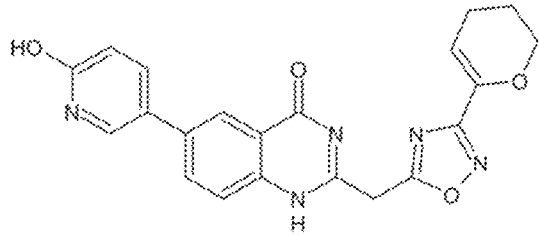
Figure 1A:
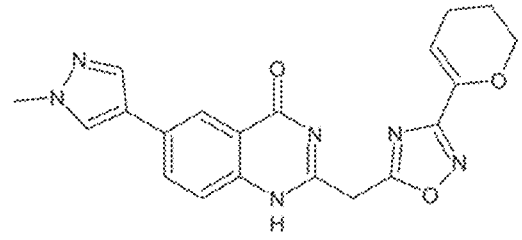
Figure 1A:
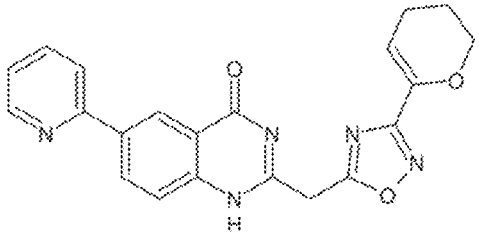
Figure 1C:
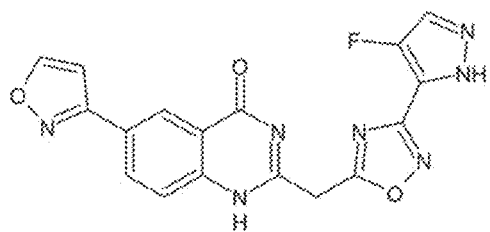
Figure 1C:
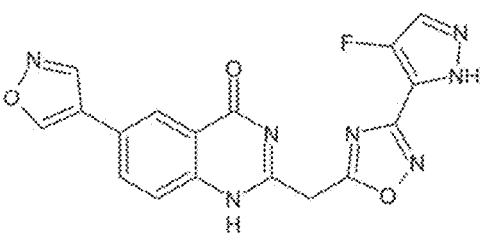
Figure 1C:
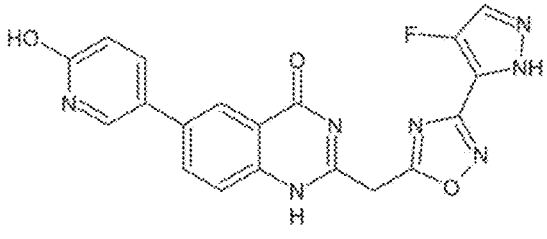
Figure 1C:
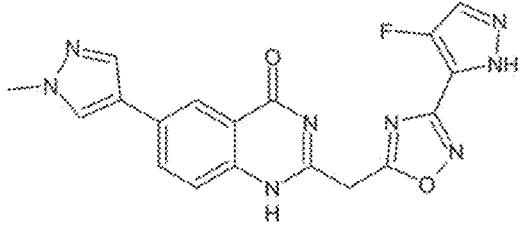
Figure 1C:
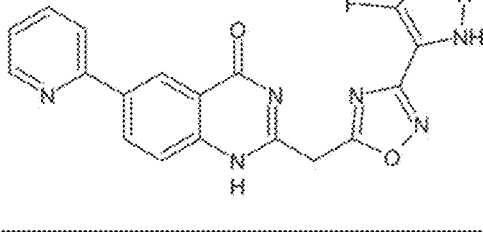
Figure 1D:
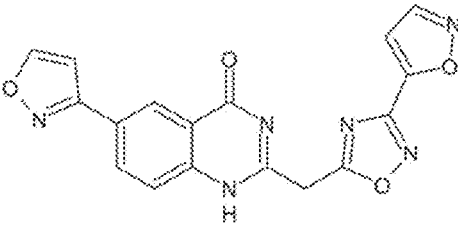
Figure 1D:
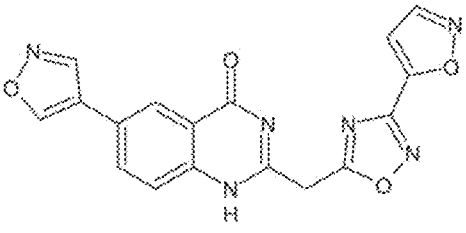
Figure 1D:
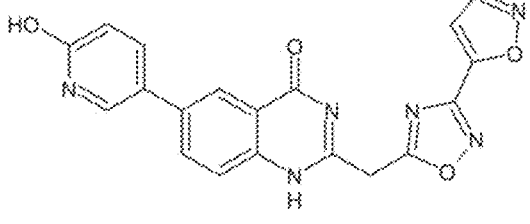
Figure 1D:
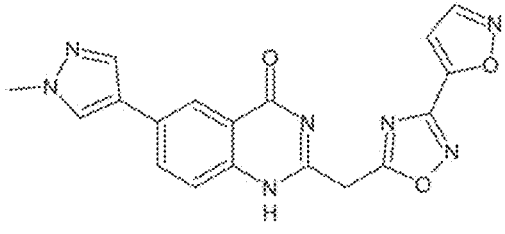
Figure 1D:
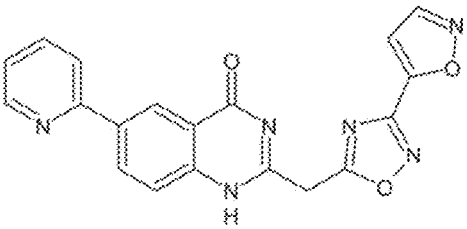
Figure 1F:
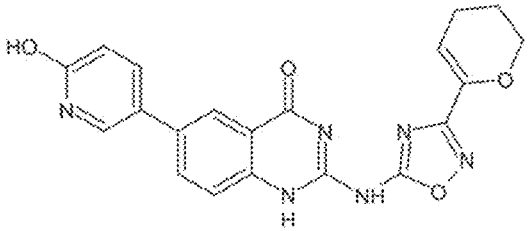
Figure 1F:
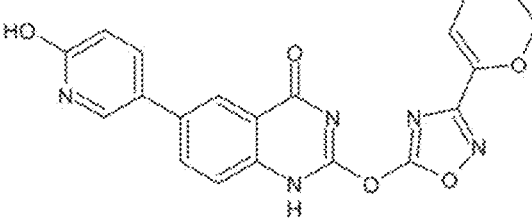
Figure 1F:
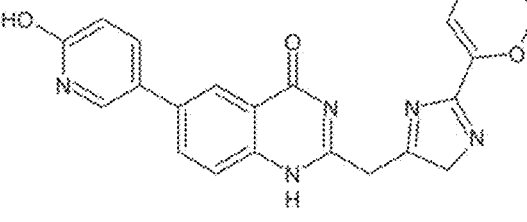
Figure 1F:
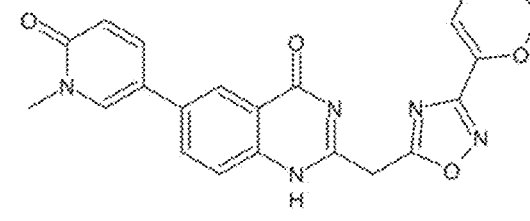
Figure 1F:
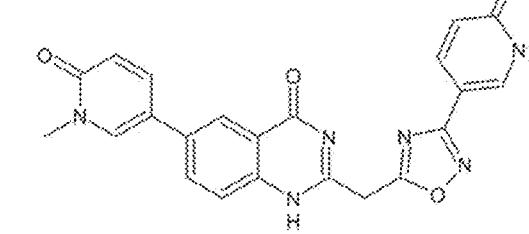

The term "substantially pure" refers to having a purity of at least 90% by weight, preferably at least 95% by weight such as at least 98%, 99% or about 100% by weight.

The term "halogen" refers to fluorine, chlorine, bromine, and iodine. Fluorine, chlorine, and bromine are preferred.

The term "hetero atom" refers to an oxygen atom, a sulfur atom, and a nitrogen atom.

The term "alkyl" includes a monovalent straight or branched hydrocarbon group having one to eight carbon atom(s). Examples include methyl, ethyl, n-propyl, isopropyl, n-butyl, isobutyl, sec-butyl, tert-butyl, n-pentyl, isopentyl, neo-pentyl, n-hexyl, isohexyl, n-heptyl, n-octyl, and the like. C1-C6 alkyl is preferred. C1-C4 alkyl or C1-C3 alkyl is further preferred. When a number of carbons is specified, it means "alkyl" having the carbon number within the range.

The term "alkenyl" includes a monovalent straight or branched hydrocarbon group having two to eight carbon atoms and one or more double bond(s). Examples include vinyl, allyl, 1-propenyl, 2-butenyl, 2-pentenyl, 2-hexenyl, 2-heptenyl, 2-octenyl, and the like. C2-C6 alkenyl is preferred. C2-C4 or C2-C3 alkenyl is further preferred.

The term "alkynyl" includes a monovalent straight or branched hydrocarbon group having two to eight carbon atoms and one or more triple bond(s). Examples include ethynyl, 1-propynyl, 2-propynyl, 2-butynyl, 2-pentynyl, 2-hexynyl, 2-heptynyl, 2-octynyl, and the like. C2-C6 alkynyl is preferred. C2-C4 or C2-C3 alkynyl is further preferred.

The term "cycloalkyl" includes a cycloalkyl having three to eight carbon atoms. Examples include cyclopropyl, cyclobutyl, cyclopentyl, cyclohexyl, cycloheptyl, cyclooctyl, and the like. C3-C6 cycloalkyl is preferred.

The term "cycloalkenyl" includes a cycloalkenyl having three to eight carbon atoms. Examples include cyclopropenyl, cyclobutenyl, cyclopentenyl, cyclohexenyl, cycloheptenyl, cyclooctenyl, and the like. C3-C6 cycloalkenyl is preferred.

The term "alkyloxy" includes a group wherein an oxygen atom is substituted with one "alkyl" as described herein. Examples include methyloxy, ethyloxy, n-propyloxy, isopropyloxy, n-butyloxy, isobutyloxy, sec-butyloxy, tert-butyloxy, n-pentyloxy, isopentyloxy, 2-pentyloxy, 3-pentyloxy, n-hexyloxy, isohexyloxy, 2-hexyloxy, 3-hexyloxy, n-heptyloxy, n-octyloxy, and the like. C1-C6 alkyloxy is preferred. C1-C4 alkyloxy or C1-C3 alkyloxy is further preferred. When a number of carbons is specified, it means "alkyloxy" having the carbon number within the range.

The term "alkenyloxy" includes a group wherein an oxygen atom is substituted with one "alkenyl" as described herein. Examples include vinyloxy, allyloxy, 1-propenyloxy, 2-butenyloxy, 2-pentenyloxy, 2-hexenyloxy, 2-heptenyloxy, 2-octenyloxy, and the like. C2-C6 alkenyloxy is preferred. Moreover, C2-C4 or C2-C3 alkenyloxy is further preferred. When a number of carbons is specified, it means "alkenyloxy" having the carbon number within the range.

The term "alkynyloxy" includes a group wherein an oxygen atom is substituted with one "alkynyl" as described herein. Examples include ethynyloxy, 1-propynyloxy, 2-propynyloxy, 2-butynyloxy, 2-pentynyloxy, 2-hexynyloxy, 2-heptynyl oxy, 2-octynyloxy, and the like. C2-C6 alkynyloxy is preferred. C2-C4 or C2-C3 alkynyloxy is further preferred. When a number of carbons is specified, it means "alkynyloxy" having the carbon number within the range.

The term "cycloalkyloxy" includes a group wherein an oxygen atom is substituted with one "cycloalkyl" as described herein. Examples include cyclopropyloxy, cyclobutyloxy, cyclopentyloxy, cyclohexyloxy, cycloheptyloxy, and cyclooctyloxy. C3-C6 cycloalkyloxy is preferred. When a number of carbons is specified, it means "cycloalkyloxy" having the carbon number within the range.

The term "cycloalkenyloxy" includes a group wherein an oxygen atom is substituted with one "cycloalkenyl" as described herein. Examples include cyclopropenyloxy, cyclobutenyloxy, cyclopentenyloxy, cyclohexenyloxy, cycloheptenyloxy, and cyclooctenyloxy. C3-C6 cycloalkenyloxy is preferred. When a number of carbons is specified, it means "cycloalkenyloxy" having the carbon number within the range.

The term "alkylthio" includes a group wherein a sulfur atom is substituted with one "alkyl" as described herein. Examples include methylthio, ethylthio, n-propylthio, isopropylthio, n-butylthio, isobutylthio, sec-butylthio, tert-butylthio, n-pentylthio, isopentylthio, 2-pentylthio, 3-pentylthio, n-hexylthio, isohexylthio, 2-hexylthio, 3-hexylthio, n-heptylthio, n-octylthio, and the like. C1-C6 Alkylthio is preferred. C1-C4 alkylthio is further preferred. C1-C3, C1-C2, or C1 alkylthio is further preferred. When a number of carbons is specified, it means "alkylthio" having the carbon number within the range.

The term "alkenylthio" includes a group wherein a sulfur atom is substituted with one "alkenyl" as described herein. Examples include vinylthio, allylthio, 1-propenylthio, 2-butenylthio, 2-pentenylthio, 2-hexenylthio, 2-heptenylthio, 2-octenylthio, and the like. C2-C6 Alkenylthio is preferred. C2-C4 or C2-C3 alkylthio is further preferred. When a number of carbons is specified, it means "alkenylthio" having the carbon number within the range. The term "alkynylthio" includes a group wherein a sulfur atom is substituted with one "alkynyl" as described herein. Examples include ethynylthio, 1-propynylthio, 2-propynylthio, 2-butynylthio, 2-pentynylthio, 2-hexynylthio, 2-heptynylthio, 2-octynylthio, and the like. C2-C6 alkynylthio is preferred. C2-C4 or C2-C3 alkynylthio is further preferred. When a number of carbons is specified, it means "alkynylthio" having the carbon number within the range.

The term "alkylsulfinyl" includes a group wherein sulfinyl is substituted with one "alkyl" as described herein. Examples include methylsulfinyl, ethylsulfinyl, n-propylsulfinyl, isopropylsulfinyl, n-butylsulfinyl, isobutylsulfinyl, sec-butylsulfinyl, tert-butylsulfinyl, n-pentylsulfinyl, isopentylsulfinyl, 2-pentylsulfinyl, 3-pentylsulfinyl, n-hexylsulfinyl, isohexylsulfinyl, 2-hexylsulfinyl, 3-hexylsulfinyl, n-heptylsulfinyl, n-octylsulfinyl, and the like. C1-C6 alkylsulfinyl is preferred. C1-C4 or C1-C3 alkylsulfinyl is further preferred.

The term "alkylsulfonyl" includes a group wherein sulfonyl is substituted with one "alkyl" as described herein. Examples include methylsulfonyl, ethylsulfonyl, n-propylsulfonyl, isopropylsulfonyl, n-butylsulfonyl, isobutylsulfonyl, sec-butylsulfonyl, tert-butylsulfonyl, n-pentylsulfonyl, isopentylsulfonyl, 2-pentylsulfonyl, 3-pentylsulfonyl, n-hexylsulfonyl, isohexylsulfonyl, 2-hexylsulfonyl, 3-hexylsulfonyl, n-heptylsulfonyl, n-octylsulfonyl, and the like. C1-C6 alkylsulfonyl is preferred. C1-C4 or C1-C3 alkylsulfonyl is further preferred.

The term "alkylsulfonyloxy" includes a group wherein an oxygen atom is substituted with one "alkylsulfonyl" as described herein. Examples include methylsulfonyloxy, ethylsulfonyloxy, n-propylsulfonyloxy, isopropylsulfonyloxy, n-butylsulfonyloxy, isobutylsulfonyloxy, sec-butylsulfonyloxy, tert-butylsulfonyloxy, n-pentylsulfonyloxy, isopentylsulfonyloxy, 2-pentylsulfonyloxy, 3-pentylsulfonyloxy, n-hexylsulfonyloxy, isohexylsulfonyloxy, 2-hexylsulfonyloxy, 3-hexylsulfonyloxy, n-heptylsulfonyloxy, n-octylsulfonyloxy, and the like. C1-C6 alkylsulfonyl is preferred. C1-C4 or C1-C3 alkylsulfonyl is further preferred.

The term "cycloalkylthio" includes a group wherein a sulfur atom is substituted with one "cycloalkyl" as described herein. Examples include cyclopropylthio, cyclobutylthio, cyclopentylthio, cyclohexylthio, cycloheptylthio, cyclooctylthio, and the like. C3-C6 cycloalkylthio is preferred. When a number of carbons is specified, it means "cycloalkylthio" having the carbon number within the range.

The term "cycloalkylsulfinyl" includes a group in which sulfinyl is substituted with one "cycloalkyl" as described herein. Examples include cyclopropylsulfinyl, cyclobutylsulfinyl, cyclopentylsulfinyl, cyclohexylsulfinyl, cycloheptylsulfinyl, and cyclooctylsulfinyl. Preferably C3-C6 cycloalkylsulfinyl.

The term "cycloalkylsulfonyl" includes a group in which sulfonyl is substituted with one "cycloalkyl" as described herein. Examples include cyclopropylsulfonyl, cyclobutylsulfonyl, cyclopentylsulfonyl, cyclohexylsulfonyl, cycloheptylsulfonyl, and cyclooctylsulfonyl. C3-C6 cycloalkylsulfonyl is preferred.

The term "cycloalkylsulfonyloxy" includes a group in which an oxygen atom is substituted with one "cycloalkylsulfonyl" as described herein. Examples include cyclopropylsulfonyloxy, cyclobutylsulfonyloxy, cyclopentyl sulfonyloxy, cyclohexyl sulfonyloxy, cycloheptylsulfonyloxy, and cyclooctylsulfonyloxy. C6-C3 cycloalkylsulfonyloxy is preferred.

The term "cycloalkenylthio" includes a group in which a sulfur atom is substituted with one "cycloalkenyl" as described herein. Examples include cyclopropenylthio, cyclobutenylthio, cyclopentenylthio, cyclohexenylthio, cycloheptenylthio, and cyclooctenylthio. C3-C6 cycloalkenylthio is preferred. When a number of carbons is specified, it means "cycloalkenylthio" having the carbon number within the range.

The term "cycloalkenylsulfinyl" includes a group in which sulfinyl is substituted with one "cycloalkenyl" as described herein. Examples include cyclopropenylsulfinyl, cyclobutenylsulfinyl, cyclopentenylsulfinyl, cyclohexenylsulfinyl, cycloheptenylsulfinyl, and cyclooctenylsulfinyl. C3-C6 cycloalkenylsulfinyl is preferred.

The term "cycloalkenylsulfonyl" includes a group in which sulfonyl is substituted with one "cycloalkenyl" as described herein. Examples include cyclopropenylsulfonyl, cyclobutenylsulfonyl, cyclopentenylsulfonyl, cyclohexenylsulfonyl, cycloheptenylsulfonyl, and cyclooctenylsulfonyl. Preferably C3-C6 cycloalkenylsulfonyl is preferred.

The term "cycloalkenylsulfonyloxy" includes a group in which an oxygen atom is substituted with one "cycloalkenylsulfonyl" described as described herein. Examples include cyclopropenylsulfonyloxy, cyclobutenylsulfonyloxy, cyclopentenylsulfonyloxy, cyclohexenylsulfonyloxy, cycloheptenylsulfonyloxy, and cyclooctenylsulfonyloxy. C3-C6 cycloalkenylsulfonyloxy is preferred.

The term "alkyloxycarbonyl" includes a group in which carbonyl is substituted with one "alkyloxy" as described herein. Examples include methyloxy carbonyl, ethyloxycarbonyl, n-propyloxycarbonyl, isopropyloxycarbonyl, n-butyloxycarbonyl, tert-butyloxycarbonyl, and n-pentyloxycarbonyl. C1-C6, C1-C4, or C1-C3 alkyloxycarbonyl is preferred. C1-C2 alkyloxycarbonyl is further preferred.

The term "alkenyloxycarbonyl" includes a group in which carbonyl is substituted with one "alkenyloxy" as described herein. Examples include vinyloxycarbonyl, allyloxycarbonyl, 1-propenyloxycarbonyl, 2-butenyloxycarbonyl, and 2-pentenyloxyarbonyl.

C2-C6, C2-C4, or C2-C3 alkyloxycarbonyl is preferred.

The term "alkynyloxycarbonyl" includes a group in which carbonyl is substituted with one "alkynyloxy" as described herein. Examples include ethynyloxycarbonyl, 1-propynyloxycarbonyl, 2-propynyloxycarbonyl, 2-butynyloxyarbonyl, and 2-pentynyloxycarbonyl. C2-C6, C2-C4, or C2-C3 alkynyloxycarbonyl is preferred.

The term "acyl" includes alkylcarbonyl wherein the part of alkyl is "alkyl" as described herein, alkenylcarbonyl wherein the part of alkenyl is "alkenyl" as described herein, alkynylcarbonyl wherein the part of alkynyl is "alkynyl" as described herein, cycloalkylcarbonyl wherein the part of cycloalkyl is "cycloalkyl" as described herein, arylcarbonyl wherein the part of aryl is "aryl" as described herein, heteroaryl carbonyl wherein the part of heteroaryl is "heteroaryl" as described herein, and non-aromatic heterocycliccarbonyl wherein the part of non-aromatic heterocyclic group is "non-aromatic heterocyclic group" as described herein. "Alkyl," "alkenyl," "alkynyl," "cycloalkyl," "aryl," "heteroaryl," and "non-aromatic heterocyclic group" may be substituted respectively with substituent groups exemplified in "optionally substituted alkyl," "optionally substituted alkenyl," "optionally substituted alkynyl," "optionally substituted cycloalkyl," "optionally substituted aryl," "optionally substituted heteroaryl," and "optionally substituted non-aromatic heterocyclic group" as described herein. Examples of the acyl group include acetyl, propionyl, butyroyl, cyclohexylcarbonyl, benzoyl, pyridinecarbonyl, and the like.

The term "optionally substituted amino" includes an amino group which may be substituted with one or two group(s) of "alkyl" as described herein, "alkenyl" as described herein, "alkynyl" as described herein, "cycloalkyl" as described herein, "cycloalkynyl" as described herein, "aryl" as described herein, "heteroaryl" as described herein, "acyl" as described herein, "alkyloxycarbonyl" as described herein, "alkenyloxycarbonyl" as described herein, "alkynyloxycarbonyl" as described herein, "alkyl sulfonyl," "alkenylsulfonyl," "alkynylsulfonyl," "aryl sulfonyl," and/or "heteroaryl sulfonyl" as described herein. Examples of the optionally substituted amino group include amino, methylamino, dimethylamino, ethylamino, diethylamino, ethylmethylamino, benzylamino, acetylamino, benzoylamino, methyloxycarbonylamino, and methanesulfonylamino. Amino, methylamino, dimethylamino, ethylmethylamino, diethylamino, acetylamino, and methanesulfonylamino are preferred.

The term "optionally substituted carbamoyl" includes an aminocarbonyl group wherein the part of optionally substituted amino is "optionally substituted amino" as described herein. Examples of the optionally substituted carbamoyl group includes carbamoyl, N-methylcarbamoyl, N,N-dimethylcarbamoyl, N-ethyl-N-methylcarbamoyl, N,N-diethylcarbamoyl, N-phenylcarbamoyl, N-benzylcarbamoyl, N-acetylcarbamoyl, and N-methylsulfonylcarbamoyl etc. Carbamoyl, N-methylcarbamoyl, N,N-dimethylcarbamoyl, and N-methylsulfonylcarbamoyl etc. are preferred.

The term "optionally substituted sulfamoyl" includes an aminosulfonyl group wherein the part of optionally substituted amino is "optionally substituted amino" as described herein. Examples of the optionally substituted sulfamoyl group include sulfamoyl, N-methyl sulfamoyl, N,N-dimethylsulfamoyl, N-ethyl-N-methyl sulfamoyl, N,N-diethylsulfamoyl, N-phenylsulfamoyl, N-benzylsulfamoyl, N-acetylsulfamoyl, and N-methyl sulfonyl sulfamoyl etc. Sulfamoyl, N-methylsulfamoyl, N,N-dimethylsulfamoyl, and N-methylsulfonylsulfamoyl etc. are preferred.

The term "alkylene" means a straight or branched alkylene group having one to eight carbon atom(s). Examples include methylene, ethylene, 1-methylethylene, trimethylene, 1-methyltrimethylene, pentamethylene, hexamethylene, and the like. C1-C4 or $C_{1-3}$ alkylenes are preferred. C1-C2 or C1 alkylene is further preferred.

The term "aryl" includes an aromatic monocyclic or aromatic fused cyclic hydrocarbons. It may be fused with "cycloalkyl" as described herein, "cycloalkenyl" as described herein or "non-aromatic heterocyclic group" as described herein at any possible position. Both of monocyclic ring and fused ring may be substituted at any position. Examples include phenyl, 1-naphthyl, 2-naphthyl, anthryl, tetrahydronaphthyl, 1,3-benzodioxolyl, 1,4-benzodioxanyl etc. Phenyl, 1-naphthyl, and 2-naphthyl are preferred. Phenyl is further preferred.

The term "non-aromatic heterocyclic group" includes a 5- to 7-membered non-aromatic heterocyclic ring containing one or more of heteroatom(s) selected independently from oxygen, sulfur, and nitrogen atoms or a multi cyclic ring formed by fusing the two or more rings thereof. Examples include pyrrolidinyl (e.g., 1-pyrrolidinyl, 2-pyrrolidinyl), pyrrolinyl (e.g., 3-pyrrolinyl), imidazolidinyl (e.g., 2-imidazolidinyl), imidazolinyl (e.g., imidazolinyl), pyrazolidinyl (e.g., 1-pyrazolidinyl, 2-pyrazolidinyl), pyrazolinyl (e.g., pyrazolinyl), piperidyl (e.g., piperidino, 2-piperidyl), piperazinyl (e.g., 1-piperazinyl), indolinyl (e.g., 1-indolinyl), isoindolinyl (e.g., isoindolinyl), morpholinyl (e.g., morpholino, 3-morpholinyl) etc.

The term "heteroaryl" includes a 5- to 6-membered aromatic ring containing one or more of heteroatom(s) selected independently from oxygen, sulfur, and nitrogen atoms. It may be fused with "cycloalkyl" as described herein, "aryl" as described herein, "non-aromatic heterocyclic group" as described herein, or other heteroaryl at any possible position. The heteroaryl group may be substituted at any position whenever it is a monocyclic ring or a fused ring. Examples include pyrrolyl (e.g., 1-pyrrolyl, 2-pyrrolyl, 3-pyrrolyl), furyl (e.g., 2-furyl, 3-furyl), thienyl (e.g., 2-thienyl, 3-thienyl), imidazolyl (e.g., 2-imidazolyl, 4-imidazolyl), pyrazolyl (e.g., 1-pyrazolyl, 3-pyrazolyl), isothiazolyl (e.g., 3-isothiazolyl), isoxazolyl (e.g., 3-isoxazolyl), oxazolyl (e.g., 2-oxazolyl), thiazolyl (e.g., 2-thiazolyl), pyridyl (e.g., 2-pyridyl, 3-pyridyl, 4-pyridyl), pyrazinyl (e.g., 2-pyrazinyl), pyrimidinyl (e.g., 2-pyrimidinyl, 4-pyrimidinyl), pyridazinyl (e.g., 3-pyridazinyl), tetrazolyl (e.g., 1H-tetrazolyl), oxadiazolyl (e.g., 1,3,4-oxadiazolyl), thiadiazolyl (e.g., 1,3,4-thiadiazolyl), indolidinyl (e.g., 2-indolidinyl, 6-indolidinyl), isoindolynyl (e.g., 2-isoindolynyl), indolyl (e.g., 1-indolyl, 2-indolyl, 3-indolyl), indazolyl (e.g., 3-indazolyl), purinyl (e.g., 8-purinyl), quinolidinyl (e.g., 2-quinolidinyl), isoquinolyl (e.g., 3-isoquinolyl), quinolyl (e.g., 2-quinolyl, 5-quinolyl), phtharazinyl (e.g., 1-phtharazinyl), naphthylidinyl (e.g., 2-naphthylidinyl), quinolanyl (e.g., 2-quinolanyl), quinazolinyl (e.g., 2-quinazolinyl), cinnolinyl (e.g., 3-cinnolinyl), pteridinyl (e.g., 2-pteridinyl), carbazolyl (e.g., 2-carbazolyl, 4-carbazolyl), phenanthridinyl (e.g., 2-phenanthridinyl, 3-phenanthridinyl), acridinyl (e.g., 1-acridinyl, 2-acridinyl), dibenzofuranyl (e.g., 1-dibenzofuranyl, 2-dibenzofuranyl), benzoimidazolyl (e.g., 2-benzoimidazolyl), benzoisoxazolyl (e.g., 3-benzoisoxazolyl), benzooxazolyl (e.g., 2-benzooxazolyl), benzooxadiazolyl (e.g., 4-benzooxadiazolyl), benzoisothiazolyl (e.g., 3-benzoisothiazolyl), benzothiazolyl (e.g., 2-benzothiazolyl), benzofuryl (e.g., 3-benzofuryl), benzothienyl (e.g., 2-benzothienyl), dibenzothienyl (e.g., 2-dibenzothienyl), and benzodioxolyl (e.g., 1,3-benzodioxolyl), etc.

The term "aryloxy" includes a group in which an oxygen atom is substituted with one "aryl" as described herein. Examples include phenyloxy and naphthyloxy, etc.

The term "arylthio" includes a group in which a sulfur atom is substituted with one "aryl" as described herein. Examples include phenylthio and naphthylthio, etc.

The term "arylsulfinyl" includes a group in which sulfinyl is substituted with one "aryl" as described herein. Examples include phenyl sulfinyl and naphthylsulfinyl, etc.

The term "arylsulfonyl" includes a group in which sulfonyl is substituted with one "aryl" as described herein. Examples include phenyl sulfonyl and naphthylsulfoinyl, etc.

Examples of "arylsulfonyloxy" include phenylsulfonyloxy and naphthylsulfonyloxy, etc.

The term "aryloxycarbonyl" includes a group in which carbonyl is substituted with one "aryloxy" as described herein. Examples include phenyloxy carbonyl, 1-naphthyloxycarbonyl and 2-naphthyloxycarbonyl, etc.

The term "heteroaryloxy" includes a group in which an oxygen atom is substituted with one "heteroaryl" as described herein. Examples include pyrrolyloxy, furyloxy, thienyloxy, imidazolyloxy, pyrazolyloxy, isothiazolyloxy, isoxazolyloxy, oxazolyloxy, thiazolyloxy, pyridyloxy, pyrazinyloxy, pyrimidinyloxy, pyridazinyloxy, tetrazolyloxy, oxadiazolyloxy, thiadiazolyloxy, indolidinyloxy, isoindolynyloxy, indolyloxy, indazolyloxy, purinyloxy, quinolidinyloxy, isoquinolyloxy, quinolyloxy, phtharazinyloxy, naphthylidinyloxy, quinolanyloxy, quinazolinyloxy, cinnolinyloxy, pteridinyloxy, carbazolyloxy, phenanthridinyloxy, acridinyloxy, dibenzofuranyloxy, benzoimidazolyloxy, benzoisoxazolyloxy, benzooxazolyloxy, benzooxadiazolyloxy, benzoisothiazolyloxy, benzothiazolyloxy, benzofuryloxy, benzothienyloxy, dibenzothienyloxy, and benzodioxolyloxy. Preferably furyloxy, thienyloxy, imidazolyloxy, pyrazolyloxy, isothiazolyloxy, isoxazolyloxy, oxazolyloxy, thiazolyloxy, pyridyloxy, pyrazinyloxy, pyrimidinyloxy, and pyridazinyloxy, etc.

The term "heteroarylthio" includes a group in which a sulfur atom is substituted with one "heteroaryl" as described herein. Examples include pyrrolylthio, furylthio, thienylthio, imidazolylthio, pyrazolylthio, isothiazolylthio, isoxazolylthio, oxazolylthio, thiazolylthio, pyridylthio, pyrazinylthio, pyrimidinylthio, pyridazinylthio, tetrazolylthio, oxadiazolylthio, thiadiazolylthio, indolidinylthio, isoindolynylthio, indolylthio, indazolylthio, purinylthio, quinolidinylthio, isoquinolylthio, quinolylthio, phtharazinylthio, naphthylidinylthio, quinolanylthio, quinazolinylthio, cinnolinylthio, pteridinylthio, carbazolylthio, phenanthridinylthio, acridinylthio, dibenzofuranylthio, benzoimidazolylthio, benzoisoxazolylthio, benzooxazolylthio, benzooxadiazolylthio, benzoisothiazolylthio, benzothiazolylthio, benzofurylthio, benzothienylthio, dibenzothienylthio, and benzodioxolylthio, etc. Preferably furylthio, thienylthio, imidazolylthio, pyrazolylthio, isothiazolylthio, isoxazolylthio, oxazolylthio, thiazolylthio, pyridylthio, pyrazinylthio, pyrimidinylthio, and pyridazinylthio, etc.

The term "heteroaryl sulfinyl" includes a group in which sulfinyl is substituted with one "heteroaryl" as described herein. Examples include pyrrolylsulfinyl, furylsulfinyl, thienyl sulfinyl, imidazolylsulfinyl, pyrazolylsulfinyl, isothiazolylsulfinyl, isoxazolylsulfinyl, oxazolylsulfinyl, thiazolylsulfinyl, pyridylsulfinyl, pyrazinylsulfinyl, pyrimidinylsulfinyl, pyridazinylsulfinyl, tetrazolylsulfinyl, oxadiazolylsulfinyl, thiadiazolylsulfinyl, indolidinylsulfinyl, isoindolylsulfinyl, indolylsulfinyl, indazolylsulfinyl, purinylsulfinyl, quinolidinylsulfinyl, isoquinolylsulfinyl, quinolylsulfinyl, phtharazinyl sulfinyl, naphthylidinylsulfinyl, quinolanylsulfinyl, quinazolinylsulfinyl, cinnolinylsulfinyl, pteridinylsulfinyl, carbazolylsulfinyl, phenanthridinylsulfinyl, acridinylsulfinyl, dibenzofuranylsulfinyl, benzoimidazolylsulfinyl, benzoisoxazolylsulfinyl, benzooxazolylsulfinyl, benzooxadiazolylsulfinyl, benzoisothiazolylsulfinyl, benzothiazolylsulfinyl, benzofurylsulfinyl, benzothienylsulfinyl, dibenzothienylsulfinyl, and benzodioxolylsulfinyl. Furylsulfinyl, thienylsulfinyl, imidazolylsulfinyl, pyrazolylsulfinyl, isothiazolylsulfinyl, isoxazolylsulfinyl, oxazolylsulfinyl, thiazolylsulfinyl, pyridyl sulfinyl, pyrazinylsulfinyl, pyrimidinylsulfinyl, and pyridazinylsulfinyl are preferred.

The term "heteroarylsulfonyl" includes a group in which sulfonyl is substituted with one "heteroaryl" as described herein. Examples include pyrrolylsulfonyl, furylsulfonyl, thienylsulfonyl, imidazolylsulfonyl, pyrazolylsulfonyl, isothiazolylsulfonyl, isoxazolylsulfonyl, oxazolylsulfonyl, thiazolylsulfonyl, pyridyl sulfonyl, pyrazinylsulfonyl, pyrimidinylsulfonyl, pyridazinylsulfonyl, tetrazolylsulfonyl, oxadiazolylsulfonyl, thiadiazolylsulfonyl, indolizinyl sulfonyl, isoindolylsulfonyl, indolylsulfonyl, indazolylsulfonyl, purinylsulfonyl, quinolidinylsulfonyl, isoquinolylsulfonyl, quinolylsulfonyl, phtharazinylsulfonyl, naphthilidinylsulfonyl, quinolanylsulfonyl, quinazolinylsulfonyl, cinnolinyl sulfonyl, pteridinyl sulfonyl, carbazolylsulfonyl, phenanthridinylsulfonyl, acridinylsulfonyl, dibenzofuranylsulfonyl, benzoimidazolylsulfonyl, benzoisoxazolylsulfonyl, benzooxazolylsulfonyl, benzooxadiazolylsulfonyl, benzoisothiazolylsulfonyl, benzothiazolylsulfonyl, benzofurylsulfonyl, benzothienylsulfonyl, dibenzothienylsulfonyl, and benzodioxolylsulfonyl, etc. Furylsulfonyl, thienylsulfonyl, imidazolylsulfonyl, pyrazolylsulfonyl, isothiazolylsulfonyl, isoxazolylsulfonyl, oxazolylsulfonyl, thiazolylsulfonyl, pyridylsulfonyl, pyrazinylsulfonyl, pyrimidinylsulfonyl, and pyridazinylsulfonyl are preferred.

The term "heteroarylsulfonyloxy" includes a group in which an oxygen atom is substituted with one "heteroaryl sulfonyl" as described herein. Examples include pyrrolylsulfonyloxy, furylsulfonyloxy, thienylsulfonyloxy, imidazolylsulfonyloxy, pyrazolylsulfonyloxy, isothiazolylsulfonyloxy, isoxazolylsulfonyloxy, oxazolylsulfonyloxy, thiazolylsulfonyloxy, pyridylsulfonyloxy, pyrazinylsulfonyloxy, pyrimidinylsulfonyloxy, pyridazinylsulfonyloxy, tetrazolylsulfonyloxy, oxadiazolylsulfonyloxy, thiadiazolylsulfonyloxy, indolizinylsulfonyloxy, isoindolylsulfonyloxy, indolylsulfonyloxy, indazolylsulfonyloxy, purinylsulfonyloxy, quinolidinylsulfonyloxy, isoquinolylsulfonyloxy, quinolylsulfonyloxy, phtharazinylsulfonyloxy, naphthilidinylsulfonyloxy, quinolanyl sulfonyloxy, quinazolinylsulfonyloxy, cinnolinylsulfonyloxy, pteridinylsulfonyloxy, carbazolylsulfonyloxy, phenanthridinylsulfonyloxy, acridinylsulfonyloxy, dibenzofuranylsulfonyloxy, benzoimidazolylsulfonyloxy, benzoisoxazolylsulfonyloxy, benzooxazolylsulfonyloxy, benzooxadiazolylsulfonyloxy, benzoisothiazolylsulfonyloxy, benzothiazolylsulfonyloxy, benzofuryl sulfonyloxy, benzothienylsulfonyloxy, dibenzothienylsulfonyloxy, and benzodioxolylsulfonyloxy, etc. Furylsulfonyloxy, thienylsulfonyloxy, imidazolylsulfonyloxy, pyrazolylsulfonyloxy, isothiazolylsulfonyloxy, isoxazolylsulfonyloxy, oxazolylsulfonyloxy, thiazolylsulfonyloxy, pyridylsulfonyloxy, pyrazinylsulfonyloxy, pyrimidinylsulfonyloxy, and pyridazinylsulfonyloxy are preferred.

The term "aromatic carbocyclic ring" includes an aromatic monocyclic or aromatic fused carbocyclic ring. Examples include a benzene ring, a naphthalene ring, and an anthracene ring. A benzene ring is preferred.

The term "aromatic heterocyclic ring" includes an aromatic monocyclic or aromatic fused heterocyclic ring. Examples include a pyrrole ring, a furan ring, a thiophen ring, a pyrazole ring, an imidazole ring, an isothiazole ring, an isoxazole ring, an oxazole ring, a thiazole ring, a pyrazine ring, a pyrimidine ring, a pyridazine ring, a tetrazole ring, an oxadiazole ring, a thiadiazole ring, an indolizine ring, an isoindole ring, an indole ring, an indazole ring, a purine ring, a quinolidine ring, an isoquinoline ring, a quinoline ring, a phtharazine ring, a naphthyridine ring, a quinolane ring, a quinazoline ring, a cinnoline ring, a pteridine ring, a carbazole ring, a phenanthridine ring, an acridine ring, a dibenzofuran ring, a benzimidazole ring, a benzisoxazole ring, a benzoxazole ring, a benzoxadiazole ring, a benzisothiazole ring, a benzothiazole ring, a benzofuran ring, a benzothiophene ring, a dibenzothiophene ring, and a benzodixolane ring are exemplified. Preferably a pyridine ring, a furan ring, and a thiophen ring are exemplified.

The term "C1-C6 alkylene" includes a straight or branched alkylene group having one to six carbon atom(s). Examples include —CH$_2$—, —CH(CH$_3$)—, —C(CH$_3$)$_2$—, —CH$_2$CH$_2$—, —CH(CH$_3$)CH$_2$—, —C(CH$_3$)$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$—, and —CH$_2$CH$_2$CH$_2$CH$_2$CH$_2$CH$_2$—. Preferred are —CH$_2$—, —CH$_2$CH$_2$—, —CH$_2$CH$_2$CH$_2$—, and —CH$_2$CH$_2$CH$_2$CH$_2$—.

The term "alkylene optionally containing one or two heteroatom(s)" of "optionally substituted alkylene optionally containing one or two heteroatom(s)" includes a straight or branched alkylene group having one to six carbon atoms, optionally containing one or two heteroatom(s) which may be substituted with "alkyl" as described herein. Examples include —CH$_2$—, —CH(CH$_3$)—, —C(CH$_3$)$_2$—, —CH$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$—, —CH$_2$CH$_2$CH$_2$CH$_2$CH$_2$CH$_2$—, —CH$_2$O—, —OCH$_2$—, —CH$_2$CH$_2$O—, —OCH$_2$CH$_2$—, —CH$_2$S—, —SCH$_2$—, —CH$_2$CH$_2$S—, —SCH$_2$CH$_2$—, —CH$_2$CH$_2$OCH$_2$CH$_2$—, —OCH$_2$CH$_2$O—, —OCH$_2$O—, —NHCH$_2$—, —N(CH$_3$)CH$_2$—, —N$^+$(CH$_3$)$_2$CH$_2$—, —NHCH$_2$CH$_2$—, and —N(CH$_3$)CH$_2$CH$_2$CH$_2$—, etc. Preferred are —CH$_2$—, —CH$_2$CH$_2$—, —CH$_2$CH$_2$CH$_2$—, —CH$_2$CH$_2$CH$_2$CH$_2$—, —OCH$_2$CH$_2$O—, —OCH$_2$O—, and —N(CH$_3$)CH$_2$CH$_2$CH$_2$—.

The term "alkenylene optionally containing one or two heteroatom(s)" of "optionally substituted alkenylene optionally containing one or two heteroatom(s)" includes a straight or branched alkenylene group having two to six carbon atoms, optionally containing one or two heteroatom(s) which may be substituted with "alkyl" as described herein. Examples include —CH═CHCH═CH—, —CH═CHO—, —OCH═CH—, —CH═CHS—, —SCH═CH—, —CH═CHNH—, —NHCH═CH—, —CH═CH—CH═N—, and —N═CH—CH═CH—. Preferred are, —CH═CHCH═CH—, —CH═CHCH═N—, and —N═CHCH═CH—.

The term "alkynylene optionally containing one or two heteroatom(s)" includes a straight or branched alkynylene group having two to six carbon atoms, optionally containing one or two heteroatom(s) which may be substituted with "alkyl" as described herein.

Examples include —C≡CCH$_2$—, —CH$_2$C≡CCH$_2$—, —CH$_2$C≡CCH$_2$O—, —OCH$_2$C≡CH—, —CH$_2$C≡CCH$_2$S—, —SCH$_2$C≡CH—, —CH$_2$C≡CCH$_2$NH—, —NHCH$_2$C≡CH—, —CH$_2$C≡CCH$_2$N(CH$_3$)—, and —N(CH$_3$)CH$_2$C≡CH—. Especially, —CH$_2$C≡CCH$_2$—, and —OCH$_2$C≡CH— are preferred.

The term "3- to 8-membered nitrogen-containing non-aromatic heterocyclic ring" includes a ring of any of the formulas described as such in U.S. Pat. No. 8,143,285, which is incorporated herein by reference in its entirety.

The term "3- to 8-nitrogen-containing aromatic heterocyclic ring" includes a 3- to 8-membered aromatic heterocyclic ring containing one or more of nitrogen atom(s), and further optionally an oxygen atom and/or sulfur atom in the ring. Examples include pyrrolyl (e.g., 1-pyrrolyl, 2-pyrrolyl, 3-pyrrolyl), imidazolyl (e.g., 2-imidazolyl, 4-imidazolyl), pyrazolyl (e.g., 1-pyrazolyl, 3-pyrazolyl), isothiazolyl (e.g., 3-isothiazolyl), isoxazolyl (e.g., 3-isoxazolyl), oxazolyl (e.g., 2-oxazolyl), thiazolyl (e.g., 2-thiazolyl), pyridyl (e.g., 2-pyridyl, 3-pyridyl, 4-pyridyl), pyrazinyl (e.g., 2-pyrazinyl), pyrimidinyl (e.g., 2-pyrimidinyl, 4-pyrimidinyl), pyridazinyl (e.g., 3-pyridazinyl), tetrazolyl (e.g., 1H-tetrazolyl), oxadiazolyl (e.g., 1,3,4-oxadiazolyl), and thiadiazolyl (e.g., 1,3,4-thiadiazolyl).

The term "4- to 8-membered nitrogen-containing heterocyclic ring containing one or two nitrogen atom(s)" means a ring of any of the formulas described as such in U.S. Pat. No. 8,143,285, which is incorporated herein by reference in its entirety.

The term "oxo" refers to an ═O group.

"Optionally substituted" is used interchangeably herein with "substituted or unsubstituted."

In the present specification, examples of substituents in "optionally substituted alkyl," "optionally substituted alkyloxy," "optionally substituted alkylthio," "optionally substituted alkylsulfinyl," "optionally substituted alkylsulfonyl," "optionally substituted alkylsulfonyloxy," and "the" include cycloalkyl, alkylene optionally containing one or two heteroatom(s), hydroxyl, oxo, alkyloxy optionally substituted with a substituent group A at one to three position(s), thiol, alkylthio, halogen, nitro, cyano, carboxyl, sulfino (—SO$_2$H), alkyloxycarbonyl, optionally substituted amino, optionally substituted carbamoyl, acyl, aryl (e.g., phenyl) optionally substituted with a substituent group B at one to three position(s), heteroaryl (e.g., pyridyl, furyl, thienyl, imidazolyl, oxazolyl, thiazolyl, pyrazolyl) optionally substituted with a substituent group C at one to three position(s), an optionally substituted non-aromatic heterocyclic ring group (e.g., morpholinyl, pyrrolidinyl, piperazinyl) which may be substituted with a substituent group C at one to three position(s), aryloxy (e.g., phenyloxy) optionally substituted with a substituent group B at one to three position(s), alkylsulfonyl, and the like. The above-referenced "optionally substituted" moieties can be substituted with one to three of the above-referenced substituent(s) at any possible position.

In the present specification, examples of substituents in "optionally substituted alkenyl," "optionally substituted alkynyl," "optionally substituted alkenyloxy," "optionally substituted alkynyloxy," "optionally substituted alkenylthio," "optionally substituted alkynylthio," "optionally substituted alkenyloxycarbonyl," "optionally substituted alkynyloxycarbonyl," "optionally substituted cycloalkyl," "optionally substituted cycloalkenyl," "optionally substituted cycloalkyloxy," "optionally substituted cycloalkenyloxy," "optionally substituted cycloalkylthio," "optionally substituted cycloalkenylthio," "optionally substituted cycloalkylsulfinyl," "optionally substituted cycloalkenylsulfinyl," "optionally substituted cycloalkylsulfonyl," "optionally substituted cycloalkenylsulfonyl," "optionally substituted cycloalkylsulfonyloxy," "optionally substituted cycloalkenylsulfonyloxy," "optionally substituted alkenyloxycarbonyl," "optionally substituted alkylene," "optionally substituted C1-C6 alkylene," "optionally substituted alkylene optionally containing one or two heteroatom(s)," "optionally substituted alkenylene," "optionally substituted alkenylene optionally containing one or two heteroatom(s)," "optionally substituted alkynylene," and "optionally substituted alkynylene optionally containing one or two heteroatom(s)" include alkyl (such as dialkyl) optionally substituted with a substituent group D at one to three position(s), cycloalkyl, hydroxyl, oxo, alkyloxy optionally substituted with a substituent group A at one to three position(s), thiol, alkylthio, halogen, nitro, cyano, carboxyl, sulfino, alkyloxycarbonyl, optionally substituted amino, optionally substituted carbamoyl, acyl acyloxy, aryl (e.g., phenyl) optionally substituted with a substituent group B at one to three position(s), heteroaryl (e.g., pyridyl, furyl, thienyl, imidazolyl, oxazolyl, thiazolyl, pyrazolyl) optionally substituted with a substituent group C at one to three position(s), non-aromatic heterocyclic group (e.g., morpholinyl, pyrrolidinyl, piperazinyl) optionally substituted with a substituent group C at one to three position(s), aryloxy (e.g., phenyloxy) optionally substituted with a substituent group C at one to three position(s), alkylsulfonyl, and the like. The above-referenced "optionally substituted" moieties can be substituted with one or more of the above-referenced substituent(s) at any possible position.

In the present specification, examples of substituents in "optionally substituted aryl," "optionally substituted phenoxy," "optionally substituted aryloxy," "optionally substituted phenylthio," "optionally substituted arylthio," "optionally substituted arylsulfinyl," "optionally substituted arylsulfonyl," "optionally substituted arylsulfonyloxy," "optionally substituted heteroaryl," "optionally substituted heteroaryloxy," "optionally substituted heteroarylthio," "optionally substituted heteroarylsulfinyl," "optionally substituted heteroarylsulfonyl," "optionally substituted heteroarylsulfonyloxy," "optionally substituted non-aromatic heterocyclic group," "optionally substituted C6 arene-fiddiamine-$N^1$,$N^4$-diyl," and "substituted C6 arene-1,4-diamine-$N^1$,$N^4$-diyl," include alkyl optionally substituted with a substituent group D at one to three position(s), cycloalkyl, alkenyl, alkynyl, hydroxyl, alkyloxy optionally substituted with a substituent group A at one to three position(s), aryloxy (e.g., phenoxy) optionally substituted with a substituent group B at one to three position(s), thiol, alkylthio, halogen, nitro, cyano, carboxyl, sulfino, alkyloxycarbonyl, acyl, alkylsulfonyl, optionally substituted amino, optionally substituted carbamoyl, aryl (e.g., phenyl) optionally substituted with a substituent group B at one to three position(s), heteroaryl (e.g., pyridyl, furyl, thienyl, imidazolyl, oxazolyl, thiazolyl, pyrazolyl) optionally substituted with a substituent group C at one to three position(s), non-aromatic heterocyclic group (e.g., morpholinyl, pyrrolidinyl, piperazinyl) optionally substituted with a substituent group C at one to three position(s), and the like. The above-referenced "optionally substituted" moieties can be substituted with one or more of the above-referenced substituent(s) at any possible position.

Substituent group A is comprised of halogen and phenyl optionally substituted with one to three substituent(s) selected from the Substituent group B.

Substituent group B is comprised of halogen, alkyl, alkyloxy, cyano, and nitro.

Substituent group C is comprised of halogen and alkyl.

Substituent group D is comprised of halogen and alkyloxy.

"- - -" between adjacent atoms indicates a bond that is present or absent depending on the valency of the adjacent atoms in a given specified structural context. The bond may comprise localized electrons between the adjacent atoms or delocalized electrons depending on the given specified structural context.

"Optionally absent" is used interchangeably herein with "present or absent."

It is preferred that Ring A includes no more than three constituent ring heteroatoms.

In some versions, Ring A includes no more than two constituent ring heteroatoms. In some versions, Ring A includes no more than one constituent ring heteroatom.

It is preferred that Ring D includes no more than three constituent ring heteroatoms.

In some versions, Ring D includes no more than two constituent ring heteroatoms. In some versions, Ring D includes no more than one constituent ring heteroatom.

It is preferred that Ring E includes no more than three constituent ring heteroatoms. In some versions, Ring E includes no more than two constituent ring heteroatoms. In some versions, Ring E includes no more than one constituent ring heteroatom.

In some versions, at least one substituent in any pair of substituents of constituent ring atoms of Rings A, D, and E, unless explicitly specified otherwise, is a non-cyclic moiety. In some versions, at least one substituent in any pair of substituents of constituent ring atoms of Rings A, D, and E, unless explicitly specified otherwise, is independently hydrogen, halogen, or optionally substituted C1-C6 alkyl. In some versions, at least one substituent in any pair of substituents of constituent ring atoms of Rings A, D, and E, unless explicitly specified otherwise, is independently hydrogen or halogen. In some versions, at least one substituent in any pair of substituents of constituent ring atoms of Rings A, D, and E, unless explicitly specified otherwise, is hydrogen. "Vicinal" in this context refers to any two substituents bonded to adjacent constituent ring atoms.

In the course of the methods of the present invention, a therapeutically effective amount of a compound of the invention can be administered to an animal, including mammals and humans, in many ways. While in the preferred embodiment, the compounds of the invention are administered orally, parenterally, or topically, other forms of administration such as through medical compounds or aerosols are also contemplated.

For oral administration, the effective amount of compounds may be administered in, for example, a solid, semisolid, liquid, or gas state. Specific examples include tablet, capsule, powder, granule, solution, suspension, syrup, and elixir agents. However, the compounds are not limited to these forms.

To formulate the compounds of the invention into tablets, capsules, powders, granules, solutions, or suspensions, the compound is preferably mixed with a binder, a disintegrating agent and/or a lubricant. If necessary, the resultant composition may be mixed with a diluent, a buffer, an infiltrating agent, a preservative and/or a flavor, using known methods. Examples of the binder include crystalline cellulose, cellulose derivatives, cornstarch, cyclodextrins, and gelatin. Examples of the disintegrating agent include cornstarch, potato starch, and sodium carboxymethylcellulose. Examples of the lubricant include talc and magnesium stearate. Further, additives, which have been conventionally used, such as lactose and mannitol, may also be used.

For parenteral administration, the compounds of the present invention may be administered rectally or by injection. For rectal administration, a suppository may be used. The suppository may be prepared by mixing the compounds of the present invention with a pharmaceutically suitable excipient that melts at body temperature but remains solid at room temperature. Examples include but are not limited to cacao butter, carbon wax, and polyethylene glycol. The resulting composition may be molded into any desired form using methods known to the field.

For administration by injection, the compounds of the present invention may be injected hypodermically, intracutaneously, intravenously, or intramuscularly. Medicinal drugs for such injection may be prepared by dissolving, suspending or emulsifying the compounds of the invention into an aqueous or non-aqueous solvent such as vegetable oil, glyceride of synthetic resin acid, ester of higher fatty acid, or propylene glycol by a known method. If desired, additives such as a solubilizing agent, an osmoregulating agent, an emulsifier, a stabilizer, or a preservative, which has been conventionally used may also be added. While not required, it is preferred that the composition be sterile or sterilized.

To formulate the compounds of the invention into suspensions, syrups, or elixirs, a pharmaceutically suitable solvent may be used. Included among these is the non-limiting example of water.

For topical administration, topical formulations can be in a form of gel, cream, lotion, liquid, emulsion, ointment, spray, solution, suspension, and patches. Inactive ingredients in the topical formulations for example include, but not limited to, lauryl lactate (emollient/permeation enhancer), diethylene glycol monoethylether (emollient/permeation enhancer), DMSO (solubility enhancer), silicone elastomer (rheology/texture modifier), caprylic/capric triglyceride, (emollient), octisalate, (emollient/UV filter), silicone fluid (emollient/diluent), squalene (emollient), sunflower oil (emollient), and silicone dioxide (thickening agent).

The compounds of the invention may also be used together with an additional compound having other pharmaceutically suitable activity to prepare a medicinal drug. A drug, either containing a compound of the invention as a stand-alone compound or as part of a composition, may be used in the treatment of subjects in need thereof.

The compounds of the invention may also be administered in the form of an aerosol or inhalant prepared by charging the compounds in the form of a liquid or fine powder, together with a gaseous or liquid spraying agent and, if necessary, a known auxiliary agent such as an inflating agent, into a non-pressurized container such as an aerosol container or a nebulizer. A pressurized gas of, for example, dichlorofluoromethane, propane or nitrogen may be used as the spraying agent.

The compounds of the invention may be administered as a pharmaceutical composition, such as tablets, capsules, solutions, or emulsions. Administration of other forms of the compounds described in this invention, including but not limited to esters thereof, pharmaceutically suitable salts thereof, metabolites thereof, structurally related compounds thereof, analogs thereof, and combinations thereof, in a single dose or a multiple dose, are also contemplated by the present invention.

The compounds of the invention may also be administered as a nutritional additive, either as a food or nutraceutical supplement.

The terms "preventing," "treating," or "ameliorating" and similar terms used herein, include prophylaxis and full or partial treatment. The terms may also include reducing symptoms, ameliorating symptoms, reducing the severity of symptoms, reducing the incidence of the disease, or any other change in the condition of the patient, which improves the therapeutic outcome.

The compounds described in this invention are preferably used and/or administered in the form of a composition. Suitable compositions are, preferably, a pharmaceutical composition, a foodstuff, or a food supplement. These compositions provide a convenient form in which to deliver the compounds. Compositions of the invention may comprise an antioxidant in an amount effective to increase the stability of the compounds with respect to oxidation or solubility.

The amount of compound that is administered in the method of the invention or that is for administration in the use of the invention is any suitable amount. Examples include from 1 ng/kg body weight to 20 g/kg body weight, such as from 1 μg/kg body weight to 1 g/kg body weight or from 1 mg/kg body weight to 100 mg/kg body weight of compound per day. Suitable compositions can be formulated accordingly. Those of skill in the art of dosing of biologically active agents will be able to develop particular dosing regimens for various subjects based on known and well understood parameters.

A preferred composition according to the invention is a pharmaceutical composition, such as in the form of tablets, pills, capsules, caplets, multiparticulates (including granules, beads, pellets and micro-encapsulated particles), powders, elixirs, syrups, suspensions, and solutions. Pharmaceutical compositions will typically comprise a pharmaceutically acceptable diluent or carrier. Pharmaceutical compositions are preferably adapted for administration parenterally or orally. Orally administrable compositions may be in solid or liquid form and may take the form of tablets, powders, suspensions, and syrups, among other things. Optionally, the compositions comprise one or more flavoring and/or coloring agents. In general, therapeutic and nutritional compositions may comprise any substance that does not significantly interfere with the action of the compounds on the subject.

Pharmaceutically acceptable carriers suitable for use in such compositions are well known in the art of pharmacy. The compositions of the invention may contain 0.01-99% by weight of the compounds of the invention. The compositions of the invention are generally prepared in unit dosage form. Examples of unit dosages of the compounds of the invention include from 0.1 mg to 2000 mg, such as 50 mg to 1000 mg. The excipients used in the preparation of these compositions are the excipients known in the art.

Further examples of product forms for the composition are food supplements, such as in the form of a soft gel or a hard capsule comprising an encapsulating material selected from the group consisting of gelatin, starch, modified starch, starch derivatives such as glucose, sucrose, lactose, and fructose. The encapsulating material may optionally contain cross-linking or polymerizing agents, stabilizers, antioxidants, light absorbing agents for protecting light-sensitive fills, preservatives, and the like.

In general, the term "carrier" represents a composition with which the compounds described may be mixed, be it a pharmaceutical carrier, foodstuff, nutritional supplement, or dietary aid. The materials described above may be considered carriers for the purposes of the invention. In certain embodiments of the invention, the carrier has little to no biological activity on the compounds of the invention.

Dose: The methods of the present invention can comprise administering a therapeutically effective amount of compound to an animal in need thereof. The effective amount of compound depends on the form of the compound administered, the duration of the administration, the route of administration (e.g., oral or parenteral), the age of the animal, and the condition of the animal, including mammals and humans. Exemplary amounts range from 1 ng/kg/day to 20 g/kg/day, such as 50 µg/kg/day to 5 g/kg/day or 1 to 100 mg/kg/day. The effective amount of compound is most effective in treating or preventing the condition when administered for periods ranging from about 1 to 1000 days or longer, such as from 7 to 300 days or from 30 to 90 days. The effective amount of compound may be continued beyond these periods for maintenance of beneficial responses in chronic diseases.

When the effective amount of the compound of the present invention is administered in a nutritional, therapeutic, medical, or veterinary composition, an exemplary dose ranges from about 0.001 to 10.0% wt/wt to the food or nutraceutical product.

When practiced, the methods of the invention can be by way of administering the compounds to a subject via any acceptable administration route using any acceptable form, as is described above, and allowing the body of the subject to distribute the compounds to the target tissues and cells through natural processes. As is described above, administering can likewise be by direct injection to a site (e.g., organ, tissue) containing a target cell (i.e., a cell to be treated).

The amount to be administered will vary depending on the subject, stage of disease or disorder, age of the subject, general health of the subject, and various other parameters known and routinely taken into consideration by those of skill in the medical arts. As a general matter, a sufficient amount of compound will be administered in order to make a detectable change in the amount of inflammation systemically or in any particular tissue or site in the body. Reduction of inflammation may be related to amount of pain experienced by the subject, insulin, anti-nuclear antigen antibodies, TNFα, or C-reactive protein levels in the blood, the percent of regulatory T-cells in the blood, or concentration of calprotectin in feces.

The methods of the present invention can provide treatments for reducing inflammation by affecting the metabolism of immune cells. The methods can reduce inflammation systemically (i.e., throughout the subject's body) or locally (e.g., at the site of administration or the site of inflammatory cells, including but not limited to T cells and macrophages). In treating or preventing inflammation through immunometabolism, one effect that may be observed is a shift in the metabolism of glucose. In particular, the shift may be from the production of lactate from pyruvate towards the entrance into the tricarboxylic acid cycle that is tied with immunoinflammatory actions. More specifically, this shift in metabolism can be associated with an increase in the proportion of CD4+CD25+FOXP3+ or other regulatory CD4+ T-cells relative to effector CD4+ T-cells such as IL17+ Th17 or IFNγ+ Th1 effector cells. Another observed effect may be decreased cellular proliferation resulting from the combination of decreased anaerobic metabolism and increased immune checkpoint pathways. Another effect of shifts in metabolism triggered therapeutically may be decreased expression of inflammatory chemokines such as MCP-1, IL-8, or CXCL9 resulting from altered processing and storage of fatty acids. The methods can thus also be considered methods of affecting or altering the immune response of a subject to whom the therapy is administered, thereby intercepting inflammation, disease and pathology.

The methods of the present invention can provide methods of reducing inflammation. The methods can reduce inflammation systemically (i.e., throughout the subject's body) or locally (e.g., at the site of administration or the site of inflammatory cells, including but not limited to T cells and macrophages). In treating or preventing inflammation according to the methods of the present invention, one effect that may be seen is the decrease in the number of blood monocytes or macrophages and lymphocytes infiltrating a given tissue. Another may be the increase in regulatory immune cell populations, such as $CD4^+CD25^+FoxP3^+$ regulatory T-cells, or an increase in regulatory properties of lymphocytes or macrophages (e.g. increased interleukin 4 (IL-4) or IL-10 or decreased TNF-α and IL-6). Another may be the decreased presence of inflammatory genes and/or adhesion molecules. The methods can thus also be considered methods of affecting or altering the immune response of a subject to whom the therapy is administered. The subject may have any condition in which the immunomodulation of T cells or downregulation of cellular adhesion molecules is a desired outcome.

The invention provides methods of treating inflammatory or immune-mediated disease. The inflammatory or immune-mediated disease can include any disease described in Dattatreya et al. 2011 and Shurin et al. 2007, among others.

The invention provides methods of treating autoimmune diseases, such as inflammatory autoimmune diseases, with the compounds described herein. Non-limiting examples of autoimmune diseases include inflammatory bowel disease (IBD) (e.g., Crohn's disease and ulcerative colitis), irritable bowel syndrome (IBS), lupus, systemic lupus erythematosus, rheumatoid arthritis, Sjogren's syndrome, systemic scleroderma, type 1 diabetes, psoriasis, autoimmune encephalitis, multiple sclerosis, sarcoidosis, Guillain-Barre syndrome, Grave's disease, antiphospholipid syndrome and cancer-immunotherapy-induced autoimmune diseases, among others. Non-limiting examples of cancer-immunotherapy-induced autoimmune diseases include cancer immunotherapy-induced rheumatic diseases.

Non-limiting examples of multiple sclerosis include relapsing-remitting multiple sclerosis, secondary progressive multiple sclerosis, and primary progressive multiple sclerosis. The invention also provides methods of treating inflammation associated with autoimmune diseases.

The compounds of the invention can be used to treat or ameliorate the complications arising from type 1 diabetes or other autoimmune diseases. Non-limiting examples of complications from autoimmune disease include diabetic nephropathy, diabetic retinopathy, chronic pain, neuropathy, deep vein thrombosis, or atherosclerosis.

The invention provides methods of treating chronic inflammatory diseases with the compounds described herein. Non-limiting examples of chronic inflammatory diseases includes metabolic syndrome, obesity, prediabetes, cardiovascular disease, type 2 diabetes, non-alcoholic fatty liver disease, non-alcoholic steatohepatitis, cirrhosis, asthma, allergies, chronic granulomatous disease, graft versus host disease, and tumor necrosis factor receptor associated periodic syndrome; muscle wasting, such as amyotrophic lateral sclerosis, Duchenne muscular dystrophy, scoliosis, and progressive muscular atrophy; and others.

The invention provides methods of treating other inflammatory diseases such as acute colonic diverticulitis and radiation-induced inflammation of the gastrointestinal tract with the compounds described herein. Non-limiting examples of radiation-induced inflammation of the gastrointestinal tract include radiation proctitis, radiation enteritis, and radiation proctosigmoiditis.

The invention provides methods of treating allergic diseases. Examples of allergic diseases include hay fever (seasonal allergies), sinusitis, asthma, eczema, hives, anaphylaxis.

The invention provides methods of treating chronic and/or inflammatory central nervous diseases. Non-limiting examples of chronic and/or inflammatory central nervous diseases include Alzheimer's disease, Parkinson's disease, neuroinflammation resulting from stroke, traumatic brain injury, or spinal cord injury.

The invention provides methods of treating chronic and/or inflammatory respiratory diseases. Non-limiting examples of chronic and/or inflammatory respiratory diseases include chronic obstructive pulmonary disease and idiopathic pulmonary fibrosis.

The invention provides methods of inhibiting inflammation in the GI tract, wherein relevant components of the GI tract can include the stomach, small intestine, large intestine, and rectum.

The invention provides methods of treating an infectious disease with the compounds described herein. Non-limiting examples of such infectious diseases include viral infections, bacterial infections, and fungal infections.

Non-limiting examples of viral infections include infections from viruses in the family adenoviridae, such as adenovirus; viruses in the family herpesviridae such as herpes simplex, type 1, herpes simplex, type 2, varicella-zoster virus, epstein-barr virus, human cytomegalovirus, human herpesvirus, and type 8; viruses in the family papillomaviridae such as human papillomavirus; viruses in the family polyomaviridae such as BK virus and JC virus; viruses in the family poxviridae such as smallpox; viruses in the family hepadnaviridae such as hepatitis B virus; viruses in the family parvoviridae such as human bocavirus and parvovirus B19; viruses in the family astroviridae such as human astrovirus; viruses in the family caliciviridae such as norwalk virus; viruses in the family picornaviridae such as coxsackievirus, hepatitis A virus, poliovirus, and rhinovirus; viruses in the family coronaviridae such as acute respiratory syndrome virus; viruses in the family flaviviridae such as hepatitis C virus, yellow fever virus, dengue virus, and West Nile virus, viruses in the family togaviridae such as rubella virus; viruses in the family hepeviridae such as hepatitis E virus; viruses in the family retroviridae such as human immunodeficiency virus (HIV); viruses in the family orthomyxoviridae such as influenza virus; viruses in the family arenaviridae such as guanarito virus, junin virus, lassa virus, machupo virus, and sabia virus; viruses in the family bunyaviridae such as Crimean-Congo hemorrhagic fever virus; viruses in the family filoviridae such as ebola virus and marburg virus; coronavirus (COVID-19); viruses in the family paramyxoviridae such as measles virus, mumps virus, parainfluenza virus, respiratory syncytial virus, human metapneumovirus, hendra virus, and nipah virus; viruses in the family rhabdoviridae such as rabies virus; unassigned viruses such as hepatitis D virus; and viruses in the family reoviridae such as rotavirus, orbivirus, coltivirus, and banna virus, among others.

Non-limiting examples of bacterial infections include infections with the bacteria described above, in addition to *Bacillus anthracis*, *Bacillus cereus*, *Bordetella pertussis*, *Borrelia burgdorferi*, *Brucella abortus*, *Brucella cams*, *Brucella melitensis*, *Brucella suis Campylobacter jejuni Chlamydia pneumoniae*, *Chlamydia trachomatis*, *Chlamydophila psittaci*, *Clostridium botulinum*, *Clostridium difficile*, *Clostridium perfringens*, *Clostridium tetani*, *Corynebacterium diphtheriae*, *Enterococcus faecalis*, *Enterococcus faecium*, *Escherichia coli*, *Francisella tularensis*, *Haemophilus influenzae*, *Helicobacter pylori*, *Legionella pneumophila*, *Leptospira interrogans*, *Listeria monocytogenes*, *Mycobacterium leprae*, *Mycobacterium tuberculosis*, *Mycobacterium ulcerans*, *Mycoplasma pneumoniae*, *Neisseria gonorrhoeae*, *Neisseria meningitidis*, *Pseudomonas aeruginosa*, *Rickettsia rickettsii*, *Salmonella typhi*, *Salmonella typhimurium*, *Shigella sonnei*, *Staphylococcus aureus*, *Staphylococcus epidermidis*, *Staphylococcus saprophyticus*, *Streptococcus agalactiae*, *Streptococcus pneumoniae*, *Streptococcus pyogenes*, *Treponema pallidum*, *Vibrio cholerae*, *Yersinia pestis*, *Yersinia enterocolitica*, *Yersinia pseudotuberculosis*, and other species from the genera of the above-mentioned organisms.

Non-limiting examples of fungal infections include infection with fungi of the genus *Aspergillus*, such as *Aspergillus fumigatus*, which cause aspergillosis; fungi of the genus *Blastomyces*, such as *Blastomyces dermatitidis*, which cause blastomycosis; fungi of the genus *Candida*, such as *Candida albicans*, which cause candidiasis; fungi of the genus *Coccidioides*, which cause coccidioidomycosis (valley fever); fungi of the genus *Cryptococcus*, such as *Cryptococcus neoformans* and *Cryptococcus gattii*, which cause cryptococcosis; dermatophytes fungi, which cause ringworm; fungi that cause fungal keratitis, such as *Fusarium* species, *Aspergillus* species, and *Candida* species; fungi of the genus *Histoplasma*, such as *Histoplasma capsulatum*, which cause histoplasmosis; fungi of the order Mucorales, which cause mucormycosis; fungi of the genus *Saccharomyces*, such as *Saccharomyces cerevisiae*; fungi of the genus *Pneumocystis*, such as *Pneumocystis jirovecii*, which cause *pneumocystis* pneumonia; and fungi of the genus *Sporothrix*, such as *Sporothrix schenckii*, which cause sporotrichosis.

The invention also provides methods of treating hyperproliferative disorders with the compounds described herein. Hyperproliferative disorders include conditions involving uncontrolled growth of cells, such as cancers or conditions involving the growth of tumors, adenomas, or polyps. Non-limiting examples of hyperproliferative disorders include colorectal cancer, familial adenomatous polyposis (PAP), throat cancer, thyroid cancer, gastric cancer, cancers of the gastrointestinal tract, pancreatic cancer, Hodgkin lymphoma, non-Hodgkin lymphoma, acute myeloid leukemia, hepatocellular cancer, gastrointestinal stromal tumors, acute lymphoblastic leukemia, chronic myeloproliferative disorders, hypereosinophilic syndrome, mastocytosis, among others.

The depiction or definition of any moiety or compound provided herein encompasses any tautomer of the moiety or compound, unless the context clearly dictates otherwise.

The depiction or definition of any moiety or compound provided herein encompasses any salt of the moiety or compound, unless the context clearly dictates otherwise.

The elements, embodiments, versions, and method steps described herein can be used in any compatible combination whether explicitly described or not.

All combinations of method steps as used herein can be performed in any order, unless otherwise specified or clearly implied to the contrary by the context in which the referenced combination is made.

As used herein, the singular forms "a," "an," and "the" include plural referents unless the content clearly dictates otherwise.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 5 to 6, from 1 to 9, from 3.6 to 4.6, from 3.5 to 9.9, and so forth.

All patents, patent publications, and peer-reviewed publications (i.e., "references") cited herein are expressly incorporated by reference to the same extent as if each individual reference were specifically and individually indicated as being incorporated by reference. In case of conflict between the present disclosure and the incorporated references, the present disclosure controls.

It is understood that the invention is not confined to the particular construction and arrangement of parts herein illustrated and described, but embraces such modified forms thereof as come within the scope of the claims.

EXAMPLES

Molecular Modeling

Example 1. Molecular Modeling of NLRX1 Ligands

Using previously described ligands of NLRX1, including viral RNA and dietary lipids (punicic acid and docosahexaenoic acid), we determined the existence of two high-potential binding sites on the NLRX1 protein (Lu et al. 2015). These ligands were docked onto the published structure for the C terminus of NLRX1 to establish important binding residues.

Methods

Virtual Screening. To provide additional insights into preliminary scaffolds, ligand databases were docked onto the NLRX1 using AutoDock Vina at each of the two sites using cuboid search grid of size (58×40×40 angstrom) to provide predicted binding affinities and conformations of ligands. Binding affinity was normalized to molecular weight of the ligand. Top ligands were selected for further examination of binding pose.

Compound generation. From the identified residues and predicted biochemical interactions, structures were generated for high affinity NLRX1 ligands. Structures were generated and chemically optimized. Structure files were generated in .pdb format and converted to .pdbqt format through calculation of charges by Gasteiger method. Structures were docked using AutoDock Vina to confirm binding affinity.

Analysis. Compounds were preliminarily ranked by lowest predicted binding affinity normalized to molecular weight representing the most favorable binding pose through a minimization of total intermolecular energy, total internal energy, and torsional free energy. Compounds were then prioritized based on favorable distances to critical binding residues on NLRX1.

Results

From the virtual screening and optimization of new chemical entities (NCEs), the highest affinity NLRX1-binding NCEs were largely comprised of compounds with a central quinazolinone ring system. In general, binding affinities were observed to be increased in compounds that contained hydrogen bonding potential group in the E ring (see Formula I for identification of the E ring). The binding affinities of selected family members are provided in FIGS. 1A, 1B, 1C, 1D, 1E, and 1F. The predicted binding affinities in the respective lowest energy binding configuration ranged from −8.7 kcal/mol to −10.5 kcal/mol. The highest binding compound in this class of NCEs was observed to be 2-((3-(3,4-dihydro-2H-pyran-6-yl)-1,2,4-oxadiazol-5-yl)methyl)-6-(1,2-isoxazol-3-yl)quinazolin-4(1H)-one, termed NX-64-1. Other compounds with high affinity used a similar backbone but included altered A and E rings. These included NX-64-3 (2-((3-(3,4-dihydro-2H-pyran-6-yl)-1,2,4-oxadiazol-5-yl)methyl)-6-(6-hydroxypyridin-3-yl)quinazolin-4(1H)-one) and NX-64-13 (2-((3-(4-fluoro-1H-pyrazol-3-yl)-1,2,4-oxadiazol-5-yl)methyl)-6-(6-hydroxypyridin-3-yl) quinazolin-4(1H)-one). Alterations to the linker group, as in NX-64-25 (2-((3-(3,4-dihydro-2H-pyran-6-yl)-1,2,4-oxadiazol-5-yl)tert-butyl)-6-(6-hydroxypyridin-3-yl)quinazolin-4 (1H)-one), also resulted in high binding. Based on binding results and predicted physicochemical properties compounds were selected from this class for synthesis.

Medicinal Chemistry

Example 2. NX-64-2

Figure 2A:
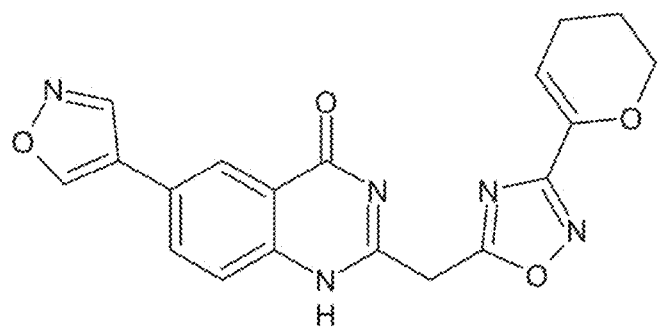
FIGS. 2A-2E. Exemplary compounds of the invention: NX-64-2 (FIG. 2A); NX-64-3 (FIG. 2B); NX-64-4 (FIG. 2C); NX-64-5 (FIG. 2D); NX-64-9 (FIG. 2E).

The synthesis of 2-((3-(3,4-dihydro-2H-pyran-6-yl)-1,2, 4-oxadiazol-5-yl)methyl)-6-(1,2-isoxazol-4-yl)quinazolin-4 (1H)-one (NX-64-2, FIG. 2A) was a five step process as detailed below.

$NH_2OH \cdot HCl$ and $Na_2CO_3$ were added to a stirred solution of 5,6-dihydro-4H-pyran-2-carbonitrile in ethanol and were allowed to stir for 2 hours at 82° C. After the completion of reaction, reaction mixture was filtered through celite, and the celite bed was washed twice. The combined organic filtrate was evaporated under reduced pressure and the obtained solid, (E)-N'-hydroxy-3, 4-dihydro-2H-pyran-6-carboximidamide, was directly taken to the next step.

Pyridine was added to a stirred solution of 2-amino-5-bromobenzamide in dichloromethane (DCM). The reaction mixture was allowed to stir for 20 minutes at room temperature. Ethyl 3-chloro-3-oxopropionate was added portion-wise while cooling. The reaction mixture was stirred at room temperature for 5 hours. The reaction mixture was quenched with water and extracted. The organic layer was dried over sodium sulfate and concentrated using rotary evaporator. The obtained crude was purified to obtain ethyl 2-((5-bromobenzamide) amino)-3-oxopropanoate.

Potassium hydroxide was added to a stirred solution of ethyl 2-((5-bromobenzamide) amino)-3-oxopropanoate in ethanol. The reaction mixture was stirred for 2 hours at room temperature. After the completion of reaction, solvent was evaporated and obtained residue was extracted. The combined organic layer was dried over sodium sulphate and evaporated under reduced pressure, and the obtained solid, containing 4(1H)-quinazolinone, 6-bromo-2-yl-ethyl acetate, was directly taken to the next step.

4(1H)-quinazolinone, 6-bromo-2-yl-ethyl acetate and (E)-N'-hydroxy-3,4-dihydro-2H-pyran-6-carboximidamide were stirred in toluene. Reaction mixture was irradiated by microwave for 12 hours. After the completion of reaction, solvent was evaporated and obtained residue was extracted. The combined organic layer was dried over sodium sulphate and evaporated under reduced pressure. Obtained crude was purified to obtain 2-((3-(3,4-dihydro-2H-pyran-6-yl)-1,2,4-oxadiazol-5-yl)methyl)-6-bromoquinazolin-4(1H)-one.

Cesium carbonate was added to a stirred solution of 2-((3-(3,4-dihydro-2H-pyran-6-yl)-1,2,4-oxadiazol-5-yl)methyl)-6-bromoquinazolin-4(1H)-one and 4-(4,4,5,5-Tetramethyl-1,3,2-dioxaborolan-2-yl)isoxazole in 1,4-dioxane and water (8:2). The reaction mixture was purged for 15 minutes with nitrogen. Pd(dppf)Cl$_2$ in DCM was added, and the reaction mixture was again purged for 10 minutes with nitrogen. The reaction mixture was stirred at 90° C. for 12 hours. The reaction mixture was filtered through celite, filtrate was concentrated under reduced pressure, and obtained residue was extracted. Organic layer was dried over sodium sulfate and concentrate using rotary evaporator. The crude was purified to obtain 2-((3-(3,4-dihydro-2H-pyran-6-yl)-1,2,4-oxadiazol-5-yl)methyl)-6-(1,2-isoxazol-4-yl)quinazolin-4(1H)-one as NX-64-2. NMR (401 MHz, DMSO) δ 12.63 (s, 1H), 11.89 (s, 1H), 11.32 (s, 1H), 11.01 (s, 1H), 9.59 (m, J=18.0 Hz, 1H), 9.30 (m, J=15.4 Hz, 1H), 8.42 (s, 1H), 8.22 (m, J=2.2 Hz, 1H), 8.14 (d, 1H), 8.00 (d, 1H), 7.62 (m, J=8.8 Hz, 1H), 7.23 (d, 1H), 5.96 (m, J=36.0 Hz, 1H), 5.02 (m, J=13.6 Hz, 1H), 4.45 (s, 1H), 4.12 (m, J=5.0 Hz, 2H), 2.24 (m, J=8.2 Hz, 2H), 1.86 (m, J=5.5 Hz, 2H), 1.24 (s, 1H).

Example 3. NX-64-3

Figure 2B:
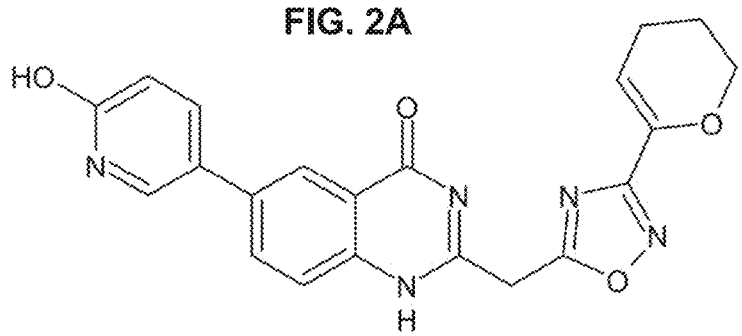

The synthesis of 2-((3-(3,4-dihydro-2H-pyran-6-yl)-1,2,4-oxadiazol-5-yl)methyl)-6-(6-hydroxypyridin-3-yl)quinazolin-4(1H)-one (NX-64-3, FIG. 2B) was a six step process as detailed below.

NH$_2$OH.HCl and Na$_2$CO$_3$ were added to a stirred solution of 5,6-dihydro-4H-pyran-2-carbonitrile in ethanol and were allowed to stir for 2 hours at 82° C. After the completion of reaction, the reaction mixture was filtered through celite, and the celite bed was washed twice. The combined organic filtrate was evaporated under reduced pressure, and the obtained solid, (E)-N'-hydroxy-3, 4-dihydro-2H-pyran-6-carboximidamide, was directly taken to the next step.

Cesium carbonate was added to a stirred solution of 2-amino-5-bromobenzamide and 2-methoxy-5-pyridineboronic acid in 1,2-dimethyxyethane (1,2-DME) and water (8:2). The reaction mixture was purged for 15 minutes with nitrogen. Pd(dppf)Cl$_2$ in DCM was added, and the reaction mixture was again purged for 10 minutes with nitrogen. The reaction mixture was stirred at 80° C. for 16 hours. The reaction mixture was filtered through celite, the filtrate was concentrated under reduced pressure, and the obtained residue was extracted. The organic layer was dried over sodium sulfate, and the remaining product was concentrated using rotary evaporator. The crude was purified to obtain 2-amino-5-(6-methoxypyridin-3-yl) benzamide as white solid.

Potassium carbonate was added to a stirred solution of 2-amino-5-(6-methoxypyridin-3-yl) benzamide in dimethylformamide (DMF). The reaction mixture was allowed to stir for 20 minutes at room temperature. Ethyl 3-chloro-3-oxopropionate was added portion-wise while cooling. The reaction mixture was stirred at room temperature for 8 hours. The reaction mixture was quenched and precipitated solid was filtered. The obtained solid, containing ethyl 3-((2-carbamoyl-4-(6-methoxypyridin-3-yl) phenyl) amino)-3-oxopropanoate), was directly taken to the next step.

Potassium hydroxide was added to a stirred solution of ethyl 3-((2-carbamoyl-4-(6-methoxypyridin-3-yl) phenyl) amino)-3-oxopropanoate) in ethanol. The reaction mixture was stirred for 2 hours at room temperature. After the completion of reaction, solvent was evaporated, and the obtained residue was extracted. The combined organic layer was dried over sodium sulphate and evaporated under reduced pressure. The obtained solid, containing ethyl 2-(6-(6-methoxypyridin-3-yl)-4-oxo-1,4-dihydroquinazolin-2-yl)acetate, was directly taken to the next step.

Ethyl 2-(6-(6-methoxypyridin-3-yl)-4-oxo-1,4-dihydroquinazolin-2-yl)acetate and (E)-N'-hydroxy-3, 4-dihydro-2H-pyran-6-carboximidamide were stirred in toluene. Potassium carbonate was added to the reaction mixture. The reaction mixture was irradiated by microwave for 2 hours. After the completion of reaction, solvent was evaporated, and the obtained residue was extracted. The combined organic layer was dried over sodium sulphate and evaporated under reduced pressure. The obtained crude was purified to obtain 2-((3-(3,4-dihydro-2H-pyran-6-yl)-1,2,4-oxadiazol-5-yl)methyl)-6-(6-methoxypyridin-3-yl)quinazolin-4(1H)-one as yellow solid. 2-((3-(3,4-dihydro-2H-pyran-6-yl)-1,2,4-oxadiazol-5-yl)methyl)-6-(6-methoxypyridin-3-yl)quinazolin-4(1H)-one was taken in DMF. LiCl and p-toluenesulsonic acid (PTSA) were added to the reaction mixture. The reaction mixture was heated at 130° C. for 5 hours. After the completion of reaction, the reaction mixture was quenched, and the precipitated solid was filtered and dried. The obtained product was purified to obtain 2-((3-(3, 4-dihydro-2H-pyran-6-yl)-1,2,4-oxadiazol-5-yl)methyl)-6-(6-hydroxypyridin-3-yl)quinazolin-4(1H)-one as NX-64-3. $^1$H NMR (401 MHz, DMSO) δ 12.57 (s, 1H), 11.91 (s, 1H), 8.19 (d, J=1.9 Hz, 1H), 7.90 (m, J=6.6 Hz, 1H), 7.56 (q, J=11.7 Hz, 4H), 6.45 (m, J=4.3 Hz, 1H), 5.88 (q, J=4.8 Hz, 1H), 5.01 (d, J=17.3 Hz, 1H), 4.44 (s, 2H), 4.12 (t, J=4.9 Hz, 2H), 2.21 (m, J=7.0 Hz, 2H), 1.86 (q, J=5.4 Hz, 2H).

Example 4. NX-64-4

Figure 2C:
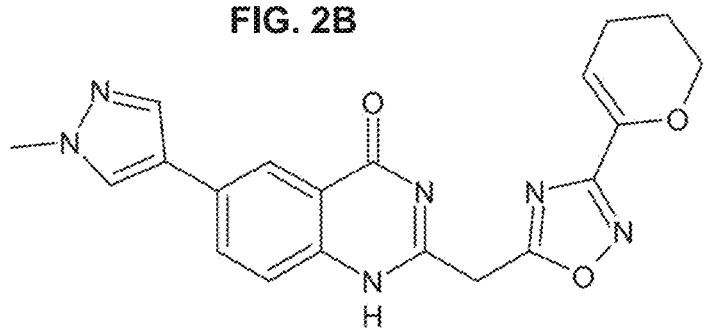

The synthesis of 2-((3-(3,4-dihydro-2H-pyran-6-yl)-1,2,4-oxadiazol-5-yl)methyl)-6-(1-methyl-1H-pyrazol-4-yl)quinazolin-4(1H)-one (NX-64-4, FIG. 2C) was a five step process as detailed below.

NH$_2$OH.HCl and Na$_2$CO$_3$ were added to a stirred solution of 5,6-dihydro-4H-pyran-2-carbonitrile in ethanol and were allowed to stir for 2 hours at 82° C. After the completion of reaction, the reaction mixture was filtered through celite, and the celite bed was washed twice. The combined organic filtrate was evaporated under reduced pressure, and the obtained solid, (E)-N'-hydroxy-3, 4-dihydro-2H-pyran-6-carboximidamide, was directly taken to the next step.

K$_2$CO$_3$ was added to a stirred solution of 2-amino-5-bromobenzamide and 1-methyl-4-(4,4,5,5-tetramethyl-1,3,2-dioxaborolan-2-yl)-1H-pyrazole in 1,4-dioxane and water (8:2). The reaction mixture was purged for 15 minutes with nitrogen. Pd(dppf)Cl$_2$ was added, and the reaction mixture was again purged for 10 minutes with nitrogen. The reaction mixture was stirred at 80° C. for 16 hours. The reaction mixture was filtered through celite, the filtrate was concentrated under reduced pressure, and the obtained residue was extracted. The organic layer was dried over sodium sulfate, and the resulting product was concentrated using rotary evaporator. The crude was purified to obtain 2-amino-5-(1-methyl-1H-pyrazol-4-yl) benzamide as white solid.

Pyridine was added to a stirred solution of 2-amino-5-(1-methyl-1H-pyrazol-4-yl) benzamide in DCM. The reaction mixture was allowed to stir for 20 minutes at room temperature. Ethyl 3-chloro-3-oxopropionate was added portion-wise while cooling. The reaction mixture was stirred at room temperature for 3 hours. The Reaction mixture was quenched with water and extracted. The organic layer was dried over sodium sulfate, and product was concentrated using rotary evaporator. The obtained crude was purified to obtain ethyl 3-((2-carbamoyl-4-(1-methyl-1H-pyrazol-4-yl) phenyl) amino)-3-oxopropanoate as white solid.

Potassium hydroxide was added to a stirred solution of ethyl 3-((2-carbamoyl-4-(1-methyl-1H-pyrazol-4-yl)phenyl)amino)-3-oxopropanoate in ethanol. The reaction mixture was allowed to stir for 2 hours at room temperature. After the completion of reaction, solvent was evaporated, and the obtained residue was extracted. The combined organic layer was dried over sodium sulphate and evaporated under reduced pressure. The obtained solid, containing ethyl 2-(6-(1-methyl-1H-pyrazol-4-yl)-4-oxo-1,4-dihydroquinazolin-2-yl)acetate, was directly taken to the next step.

Ethyl 2-(6-(1-methyl-1H-pyrazol-4-yl)-4-oxo-1,4-dihydroquinazolin-2-yl)acetate and (E)-N'-hydroxy-3,4-dihydro-2H-pyran-6-carboximidamide were stirred in DMF. Potassium carbonate was added to the reaction mixture. The reaction mixture was irradiated by microwave for 2 hours. After the completion of reaction, solvent was evaporated, and the obtained residue was extracted. The combined organic layer was dried over sodium sulphate and evaporated under reduced pressure. The obtained crude was purified to obtain 2-((3-(3,4-dihydro-2H-pyran-6-yl)-1,2,4-oxadiazol-5-yl)methyl)-6-(1-methyl-1H-pyrazol-4-yl)quinazolin-4(1H)-one as NX-64-4. $^1$H NMR (401 MHz, DMSO) δ 11.71 (s, 1H), 8.00 (m, J=22.0 Hz, 4H), 7.54 (d, J=8.4 Hz, 1H), 5.86 (s, 1H), 4.38 (s, 1.3H), 4.11 (t, J=5.0 Hz, 2H), 3.87 (s, 3H), 2.25 (t, J=25.3 Hz, 2H), 1.86 (t, J=5.2 Hz, 2H).

Example 5. NX-64-5

Figure 2D:
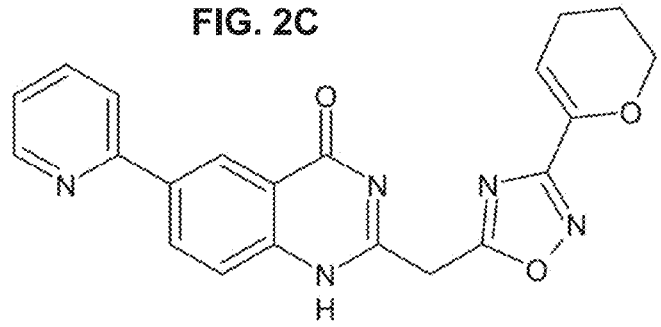

The synthesis of 2-((3-(3,4-dihydro-2H-pyran-6-yl)-1,2,4-oxadiazol-5-yl)methyl)-6-(pyridin-3-yl)quinazolin-4 (1H)-one (NX-64-5, FIG. 2D) was a five-step process as detailed below.

NH$_2$OH.HCl and Na$_2$CO$_3$ were added to a stirred solution of 5,6-dihydro-4H-pyran-2-carbonitrile in ethanol and were allowed to stir for 2 hours at 82° C. After the completion of reaction, the reaction mixture was filtered through celite, and the celite bed was washed twice. The combined organic filtrate was evaporated under reduced pressure. The obtained solid, (E)-N'-hydroxy-3, 4-dihydro-2H-pyran-6-carboximidamide, was directly taken to the next step.

Pyridine was added to a stirred solution of 2-amino-5-bromobenzamide in DCM. The reaction mixture was allowed to stir for 20 minutes at room temperature. Ethyl 3-chloro-3-oxopropionate was added portion wise while cooling. The reaction mixture was stirred at room temperature for 5 hours. The reaction mixture was quenched with water and extracted. The organic layer was dried over sodium sulfate and concentrated using a rotary evaporator. The obtained crude was purified to obtain ethyl 2-((5-bromobenzamide) amino)-3-oxopropanoate.

Potassium hydroxide was added to a stirred solution of ethyl 2-((5-bromobenzamide) amino)-3-oxopropanoate in ethanol. The reaction mixture was stirred for 2 hours at room temperature. After the completion of reaction, solvent was evaporated, and the obtained residue was extracted. The combined organic layer was dried over sodium sulphate and evaporated under reduced pressure. The obtained solid, containing 4(1H)-quinazolinone, 6-bromo-2-yl-ethyl acetate, was directly taken to the next step. 4(1H)-quinazolinone, 6-bromo-2-yl-ethyl acetate and (E)-N'-hydroxy-3, 4-dihydro-2H-pyran-6-carboximidamide were stirred in toluene. The reaction mixture was irradiated by microwave for 12 hours. After the completion of reaction, solvent was evaporated, and the obtained residue was extracted. The combined organic layer was dried over sodium sulphate and evaporated under reduced pressure. The obtained crude was purified to obtain 2-((3-(3,4-dihydro-2H-pyran-6-yl)-1,2,4-oxadiazol-5-yl)methyl)-6-bromoquinazolin-4(1H)-one.

3-(tributylstannyl)pyridine was added to a stirred solution of 2-((3-(3,4-dihydro-2H-pyran-6-yl)-1,2,4-oxadiazol-5-yl)methyl)-6-bromoquinazolin-4(1H)-one. The reaction mixture was purged for 15 minutes with nitrogen. The reaction mixture was irradiated by microwave for 2 hours. The reaction mixture was filtered through celite, the filtrate was concentrated under reduced pressure, and the obtained residue was extracted. The organic layer was dried over sodium sulfate. The product was concentrate using a rotary evaporator. The crude was purified to obtain 2-((3-(3,4-dihydro-2H-pyran-6-yl)-1,2,4-oxadiazol-5-yl)methyl)-6-(pyridin-3-yl)quinazolin-4(1H)-one as NX-64-5. $^1$H NMR (401 MHz, DMSO) δ 12.64 (s, 1H), 11.80 (m, 1H), 11.39 (s, 1H), 11.08 (s, 1H), 8.83 (s, 1H), 8.67 (m, J=11.0 Hz, 2H), 8.46 (m, J=17.4 Hz, 1H), 8.06 (m, J=11.3 Hz, 1H), 7.93 (m, J=8.0 Hz, 1H), 7.64 (m, J=13.5 Hz, 1H), 7.36 (m, J=6.5 Hz, 1H), 6.23 (s, 1H), 5.90 (s, 1H), 5.05 (d, J=18.8, 1H), 4.47 (s, 1H), 4.12 (s, 1H), 2.24 (m, J=19.8 Hz, 2H), 1.87 (m, J=5.0 Hz, 2H), 1.24 (s, 2H).

Example 6. NX-64-9

Figure 2E:
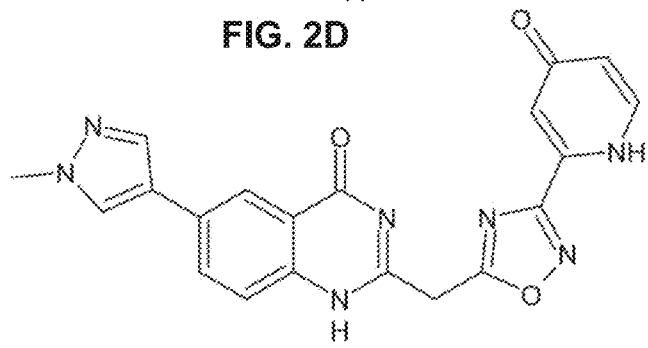

The synthesis of 2-((3-(4-oxo-1H-pyridin-2-yl)-1,2,4-oxadiazol-5-yl)methyl)-6-(1-methyl-1H-pyrazol-4-yl)quinazolin-4(1H)-one (NX-64-9, FIG. 2E) was a five step process as detailed below.

NH$_2$OH.HCl and Na$_2$CO$_3$ were added to a stirred solution of 4-hydroxypicolinonitrile in ethanol and were allowed to stir for 2 hours at 80° C. After the completion of reaction, the reaction mixture was filtered through celite, and the celite bed was washed twice. The combined organic filtrate was evaporated under reduced pressure.

The obtained solid, N'-hydroxy-4-oxo-1H-pyridine-2-carboximidamide, was directly taken to the next step.

K$_2$CO$_3$ was added to a stirred solution of 2-amino-5-bromobenzamide and 1-methyl-4-(4,4,5,5-tetramethyl-1,3, 2-dioxaborolan-2-yl)-1H-pyrazole in 1,4-dioxane and water (8:2). The reaction mixture was purged for 15 minutes with nitrogen. Pd(dppf)Cl$_2$ was added, and the reaction mixture was again purged for 10 minutes with nitrogen. The reaction mixture was stirred at 80° C. for 16 hours. The reaction mixture was filtered through celite, the filtrate was concentrated under reduced pressure, and the obtained residue was extracted. The organic layer was dried over sodium sulfate, and product was concentrated using a rotary evaporator. The crude was purified to obtain 2-amino-5-(1-methyl-1H-pyrazol-4-yl) benzamide as white solid.

Pyridine was added to a stirred solution of 2-amino-5-(1-methyl-1H-pyrazol-4-yl) benzamide in DCM. The reaction mixture was allowed to stir for 20 minutes at room temperature. Ethyl 3-chloro-3-oxopropionate was added portion-wise while cooling. The reaction mixture was stirred at room temperature for 3 hours. The reaction mixture was quenched with water and extracted. The organic layer was dried over sodium sulfate, and product was concentrated using a rotary evaporator. The obtained crude was purified to obtain ethyl 3-((2-carbamoyl-4-(1-methyl-1H-pyrazol-4-yl) phenyl) amino)-3-oxopropanoate as white solid.

Potassium hydroxide was added to a stirred solution of ethyl 3-((2-carbamoyl-4-(1-methyl-1H-pyrazol-4-yl)phenyl)amino)-3-oxopropanoate in ethanol. The reaction mixture was allowed to stir for 2 hours at room temperature. After the completion of reaction, solvent was evaporated, and the obtained residue was extracted. The combined organic layer was dried over sodium sulphate and evaporated under reduced pressure. The obtained solid, containing ethyl 2-(6-(1-methyl-1H-pyrazol-4-yl)-4-oxo-1,4-dihydroquinazolin-2-yl)acetate, was directly taken to the next step.

Ethyl 2-(6-(1-methyl-1H-pyrazol-4-yl)-4-oxo-1,4-dihydroquinazolin-2-yl)acetate and N'-hydroxy-4-oxo-1H-pyridine-2-carboximidamide were stirred in toluene. Potassium carbonate was added to the reaction mixture. The reaction mixture was irradiated by microwave for 3 hours. After the completion of reaction, solvent was evaporated, and the obtained residue was extracted. The combined organic layer was dried over sodium sulphate and evaporated under reduced pressure. The obtained crude was purified to obtain 2-((3-(4-oxo-1H-pyridin-2-yl)-1,2,4-oxadiazol-5-yl) methyl)-6-(1-methyl-1H-pyrazol-4-yl)quinazolin-4(1H)-one as NX-64-9. $^1$H NMR (401 MHz, DMSO) δ 11.55 (s, 1H), 8.40 (s, 1H), 8.25 (m, J=25.7 Hz, 2H), 7.89 (m, J=20.6 Hz, 2H), 7.48 (m, J=17.9 Hz, 1H), 7.18 (m, J=6.4 Hz, 1H), 6.87 (s, 1H), 4.99 (m, J=89.4 Hz, 1H), 4.53 (s, 1H), 3.87 (s, 3H), 1.23 (s, 2H).

EXPERIMENTAL STUDIES

Example 7. Immunological Screening In Vitro in CD4+ T Cells

Introduction

CD4+ T cells are central to the pathogenesis of many autoimmune diseases and the amplification of inflammatory responses that can contribute to organ damage. As such, the trafficking and differentiation of these cells is an effective option for the amelioration of symptoms and prevention of flares in autoimmune disease. With the loss of NLRX1, CD4+ T cells produced greater amounts of IFNγ and TNFα and have a higher likelihood of differentiating into inflammatory subsets, such as Th17 and Th1.

Methods

Cell culture. Spleens were excised from C57BL/6 mice. Spleens were crushed between the frosted ends of microscope slides and filtered to provide a cellular suspension. Red blood cells were lysed through hypotonic lysis. Remaining cells were washed and filtered. CD4+ T cells were enriched within the suspension using magnetic sorting based negative selection. Cells were collected and plated within 96 well plates coated with anti-CD3/CD28 and cultured in the presence of NX-64-2, NX-64-3, NX-64-4, NX-64-5, or NX-64-9 at 0 or 50 nanomolar for 24 h. During the last 6 h of culture, cells were stimulated with phorbol 12-myristate-13-acetate (PMA) and ionomycin.

Immunological analysis. Cells were collected from 96 well plates and stained with a cocktail of antibodies for immunophenotyping by flow cytometry. Culture supernatant was collected and assayed for cytokine concentrations by cytometric bead array. Data was captured on a BD FACS Celesta and analyzed using FACSDiva.

Results

Figure 3A:
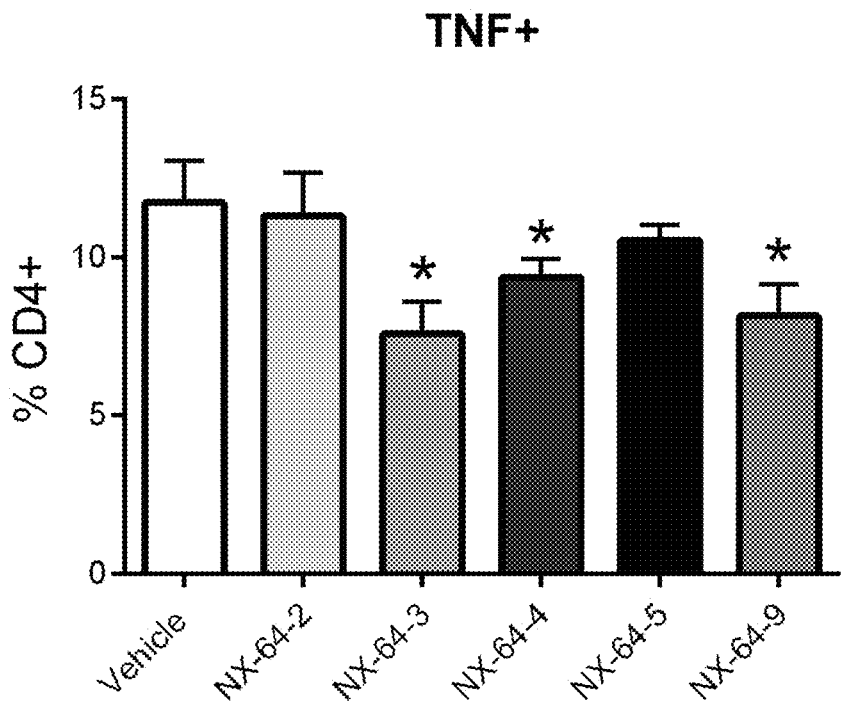
FIGS. 3A and 3B. Immunological validation of NX-64-2, NX-64-3, NX-64-4, NX-64-5, and NX-64-9 activity in CD4+ T cells. Percentages of TNFα+ (FIG. 3A) and IFNγ+ (FIG. 3B) CD4+ T cells were measured by flow cytometry after in vitro treatment of cells with NX compounds at concentrations of 50 nanomolar. Statistical significance ($p<0.05$) is marked by asterisks.
Figure 3B:
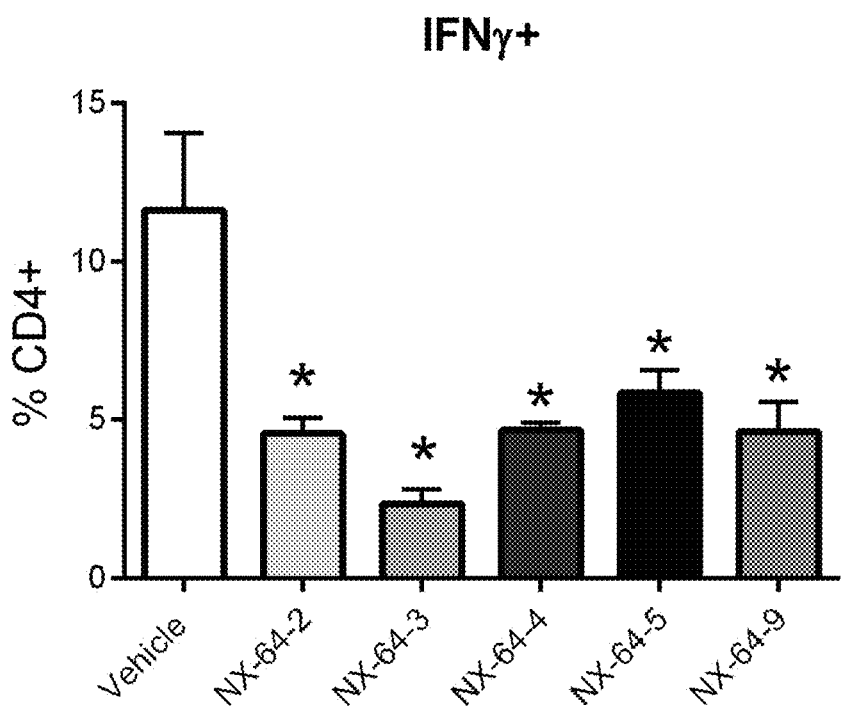

The five tested NLRX1 ligands all decreased production of TNFα (FIG. 3A) and IFNγ (FIG. 3B) in CD4+ T cell culture. NX-64-3, NX-64-4, and NX-64-9 were observed to have the largest magnitude of response in TNF+ CD4+ T cells, providing a significant reduction at 50 nanomolar. All tested compounds were observed to provide greater than 50% reduction in IFNγ+ CD4+ T cells, with NX-64-3 providing the greatest magnitude of response relative to vehicle control. We predict similar results with the other compounds defined herein, including NX-64-1, NX-64-2, NX-64-5, NX-64-6, NX-64-7, NX-64-8, NX-64-10, NX-64-11, NX-64-12, NX-64-13, NX-64-14, NX-64-15, NX-64-16, NX-64-17, NX-64-18, NX-64-19, NX-64-20, NX-64-21, NX-64-22, NX-64-23, NX-64-24, NX-64-25, NX-64-26, NX-64-27, NX-64-28, NX-64-29, and NX-64-30.

Example 8. Use of NX-64-3 in an Acute Model of IBD

Introduction

Inflammatory bowel disease is a multifactorial disease with many disease processes initiated by actions or dysfunction of the epithelial barrier (Abreu et al. 2010). A prominent and accepted animal model of the disease is induced by the administration of dextran sulfate sodium (DSS) in the drinking water of mice. Intake of DSS acts to disrupt and destroy the epithelial barrier in the distal gastrointestinal tract, in particular the colon. The disruption of the epithelial barrier allows for infiltration of the microbiome in the colonic mucosa and the ensuing recruitment and activation of immune cells. While CD4+ T cells are a major focus of development of therapeutics for IBD, recruitment of neutrophils in the intestinal lamina propria of IBD patients is one of the most predictive markers of response to treatment histological. Loss of NLRX1 results in worsened histopathology scores and increased infiltration of neutrophils and lamina propria Th17 cells.

Methods

DSS model. Mice were given DSS in drinking water for seven days to induce disruption of the epithelial layer. At project initiation, mice were 8 weeks of age and began dosing 24 hours after being placed on DSS. Mice were weighed and scored daily for symptoms of disease (diarrhea, rectal bleeding, rectal inflammation, overall behavior). NX-64-3 was prepared within a 0.5% methylcellulose (12-15 cP) solution. Dosage used was 20 mg/kg delivered once daily. Dosage was calculated based off mean body weights for each gender. Oral dosage was delivered by orogastric gavage of dosage in 0.2 mL volume.

Flow Cytometry. Colons were collected into RPMI/FBS buffer containing collagenase (300 U/mL) and DNase (50 U/mL) for digestion. Tissues were digested for 60 minutes under stirring at 37° C. Resultant cellular suspensions were filtered through 100 μm strainers, centrifuged (300×g, 8 min), and washed in fresh RPMI. Following filtration of the resulting single cell suspensions, immune cells were purified by Percoll gradient of cell-containing 40% Percoll overlayed onto 70% Percoll solution. After centrifugation, interphase was collected and washed to obtain enriched colonic lamina propria cell fractions. Cells were labeled with mixtures of extracellular (CD45, CD3, CD4, CD8, CD19, NK1.1, F4/80, CD11b, Gr1) antibodies in a sequential live staining in 96-well plates. Data was acquired using a FACS Celesta flow cytometer with FACSDiva software.

Results

Figure 4A:
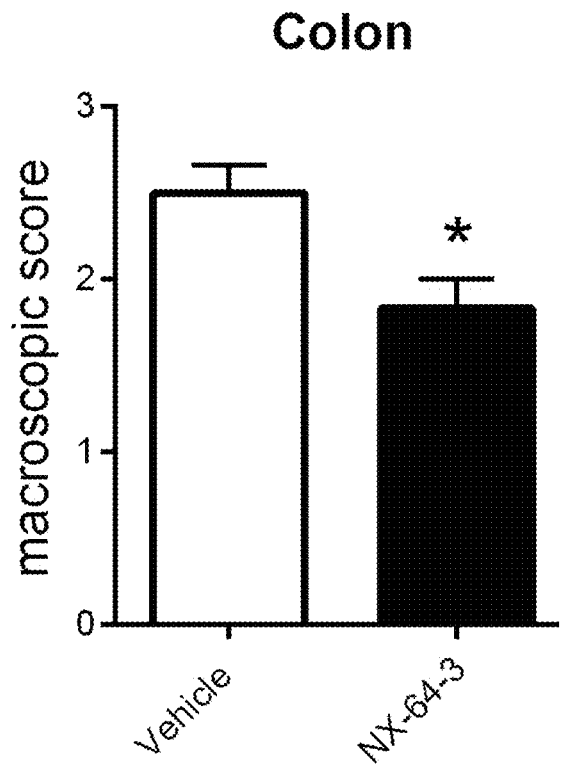
FIGS. 4A-4B. In vivo validation of NX-64-3 efficacy in a DSS model of colitis. Macroscopic scoring of colonic lesions after 7 days of DSS challenge (FIG. 4A) and flow cytometry measures of neutrophils (FIG. 4B) within the colonic lamina propria on day 7 of mice treated with vehicle or NX-64-3 (20 mg/kg) daily by oral gavage. Statistical significance ($p<0.05$) is marked by asterisks.
Figure 4B:
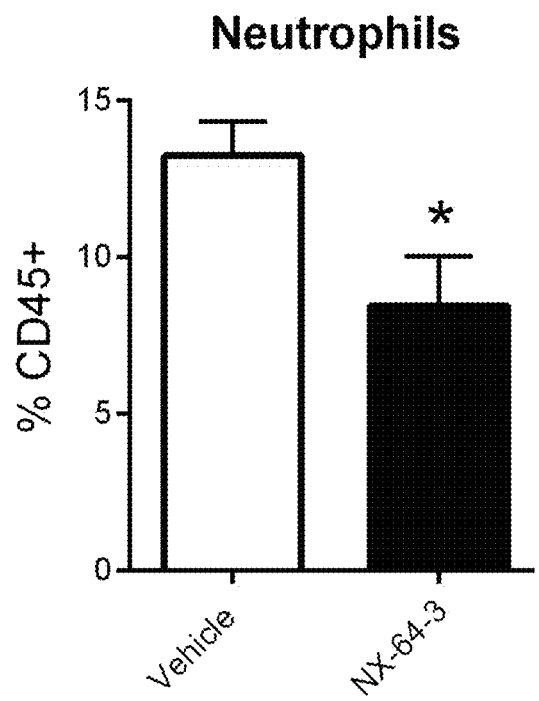

Oral NX-64-3 treatment decreased the severity of macroscopic lesions of mice challenged with DSS (FIG. 4A). Macroscopic scoring is based off of friability of the colon, thickness of intestinal wall, presence of blood, stool consistency, and colonic length. Immunologically, NX-64-3 decreased the presence of neutrophils in the colonic lamina propria (FIG. 4B). We predict similar results with the other compounds defined herein, including NX-64-1, NX-64-2, NX-64-4, NX-64-5, NX-64-6, NX-64-7, NX-64-8, NX-64-9, NX-64-10, NX-64-11, NX-64-12, NX-64-13, NX-64-14, NX-64-15, NX-64-16, NX-64-17, NX-64-18, NX-64-19, NX-64-20, NX-64-21, NX-64-22, NX-64-23, NX-64-24, NX-64-25, NX-64-26, NX-64-27, NX-64-28, NX-64-29, and NX-64-30.

Example 9. Use of NX-64-3 in a Model of Experimental Autoimmune Encephalomyelitis Multiple sclerosis (MS) afflicts over 700,000 people in the United States and 2.2 million worldwide. This widespread and debilitating illness results in decreased quality of life, with over 1.1 million DALYs, and significant healthcare related costs, over $28 billion yearly in the US (National Multiple Sclerosis Society). The global therapeutic market for MS is currently $20.5 billion per year and growing at 2.5% per year. MS patients have a higher rate of nonparticipation in the labor force with nearly 60% of patients unemployed, with 25% of patients progressing to the point of requiring home care due to disability. Despite advances and new therapies, no evidence of disease activity (NEDA) rates are 30-40%, yearly relapse rates for MS are still 30%, with only minimal effects on the progression of disease and time to disability. The pathogenesis of MS is thought to involve pathogenic Th17 cells, which are increased in the absence of NLRX1.

Methods

Mouse model. C57BL6 mice were challenged at 6- to 8-weeks of age with MOG immunization. Complete Freund's adjuvant (CFA) was prepared by suspension of heat-killed *Mycobacterium tuberculosis* (H37RA) at 10 mg/mL in incomplete Freund's adjuvant. MOG35-55 was resuspended in sterile nanopure water to a concentration of 2 mg/mL. CFA and MOG35-55 solution were emulsified in a 1:1 ratio using glass syringes and a near-closed three-way valve for 10 minutes. Emulsion was left to sit for 30 prior to immunization to ensure it is stable. Pertussis toxin was resuspended to a concentration of 2 µg/mL in PBS. MOG emulsion was administered to the left and right flank at 100 µL per site to each mouse. Pertussis toxin was administered by intraperitoneal injection (200 µL) on days 0 and 2 of the study to each mouse. Mice were treated daily with NX-64-3 at 20 mg/kg. Treatment was delivered by oral gavage. Mice were weighed and scored (0-4) daily for disease activity (coordination, gait, paralysis). Necropsies for tissue collection occurred on d 18.

Gene expression. Total RNA from spinal cord was generated using the Qiagen RNeasy mini kit. cDNA was generated using the BioRad iScript cDNA synthesis kit. Standard curves were generated by serial dilution of purified product from a standard PCR reaction with Taq DNA polymerase followed by purification using the Qiagen MinElute PCR purification kit. Expression levels were obtained from quantitative real-time PCR with SybrGreen supermix on a BioRad CFX96 Thermal cycler followed by normalization to expression of β-actin. Gene expression was measured for inflammatory cytokines, IL-1β, and TNF.

Results

Figure 5:
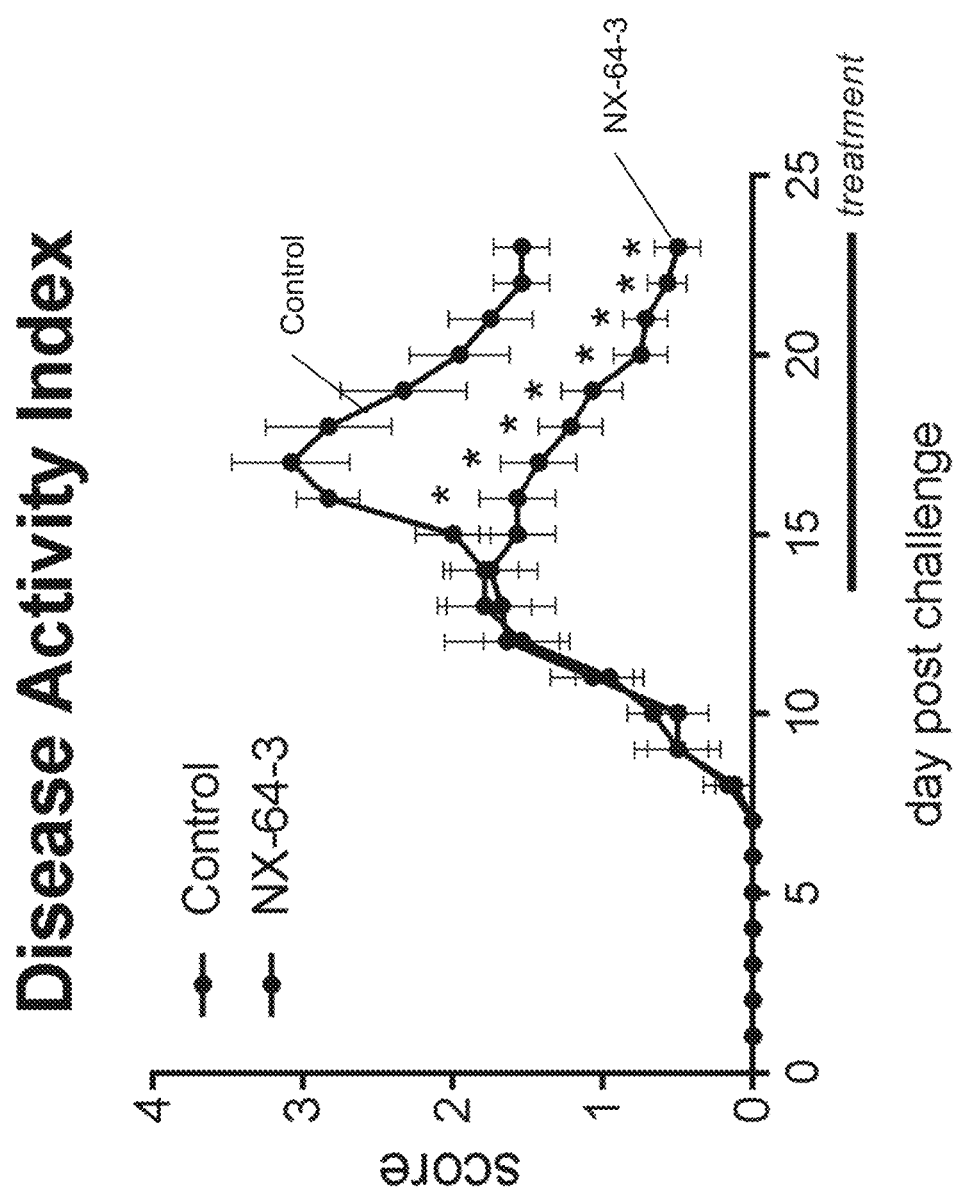
FIG. 5. In vivo validation of NX-64-3 efficacy in an experimental autoimmune encephalomyelitis model of CNS inflammation. Disease activity measurement of mice treated with vehicle or NX-64-3 (20 mg/kg) in a $MOG_{35-55}$ induced EAE model. Statistical significance ($p<0.05$) is marked by asterisks.
Figure 6A:
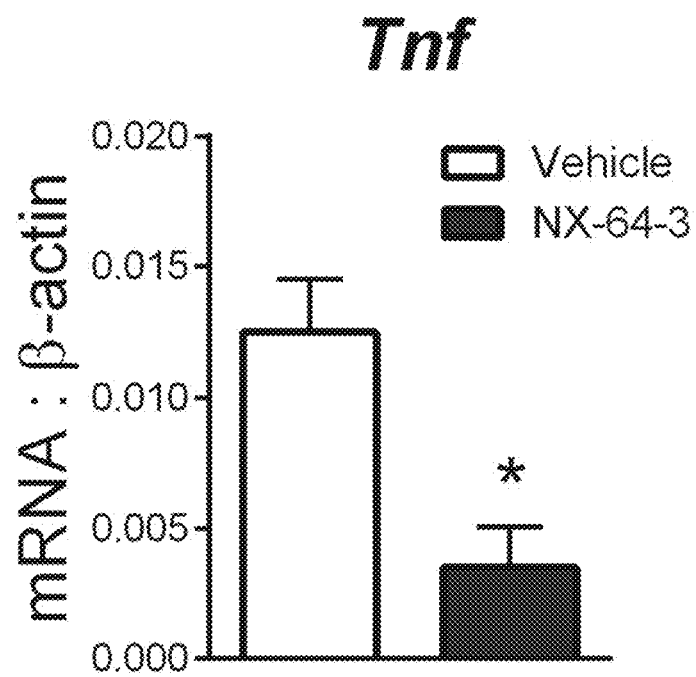
FIGS. 6A-6B. In vivo validation of NX-64-3 anti-inflammatory effects in an experimental autoimmune encephalomyelitis model. RNA expression of TNF (FIG. 6A) and Il 1b (FIG. 6B) in the spinal cord of mice on day 18 of a $MOG_{35-55}$ induced EAE model, normalized to the expression of beta-actin. Statistical significance ($p<0.05$) is marked by asterisks.
Figure 6B:
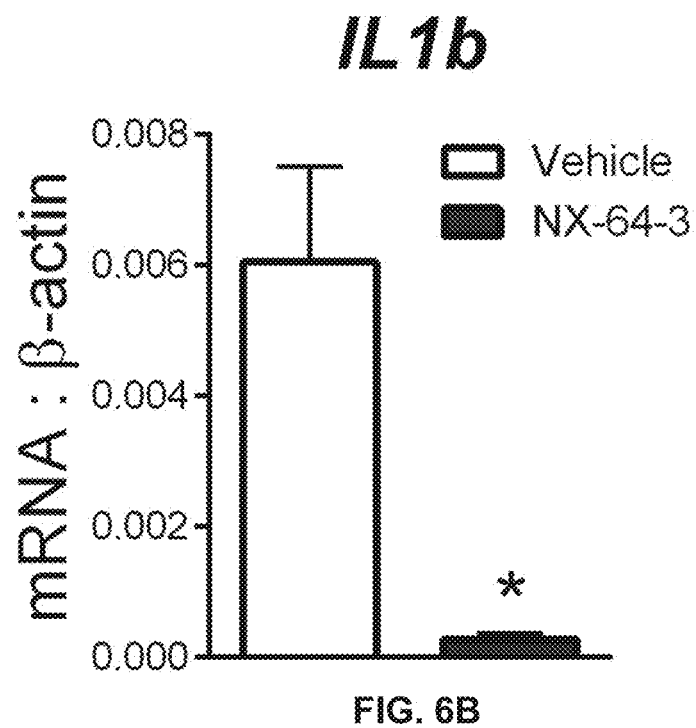

Oral NX-64-3 reduced the disease activity index of mice challenged with MOG emulsion and accelerated recovery from neurological deficiencies (FIG. 5). In spinal cord, oral NX-64-3 reduced expression of Tnf (FIG. 6A) and Il1b (FIG. 6B), suggesting an ability to reduce inflammation in the central nervous system. We predict similar results with the other compounds defined herein, including NX-64-1, NX-64-2, NX-64-4, NX-64-5, NX-64-6, NX-64-7, NX-64-8, NX-64-9, NX-64-10, NX-64-11, NX-64-12, NX-64-13, NX-64-14, NX-64-15, NX-64-16, NX-64-17, NX-64-18, NX-64-19, NX-64-20, NX-64-21, NX-64-22, NX-64-23, NX-64-24, NX-64-25, NX-64-26, NX-64-27, NX-64-28, NX-64-29, and NX-64-30.

Example 10. Use of NX-64-3 in a Model of Asthma

Asthma is a common disease affecting nearly 10% of the population with high proportions of patients unresponsive to current medications. In particular, non-type 2 asthma has a lower responsiveness to current treatments. Defects in airway epithelial cells, increased neutrophil recruitment and underlying pulmonary fibrosis create a more complex pathogenesis in many refractory patients relative to allergic asthma. Previously, the loss of NLRX1 has been identified to disrupt metabolism and cause cell death in airway epithelial cells and increase neutrophil recruitment in a variety of inflammatory conditions.

Methods

OVA-induced model. C57BL6 mice were immunized with 10 µg of ovalbumin (OVA) in aluminum hydroxide gel by intraperitoneal injection on day 0 and 7 of the experiment. Mice were then exposed to OVA (8% w/v) by aerosolization for 25 minutes daily between days 14 and 17. Treatment with NX-64-3 (20 mg/kg) or vehicle control occurred daily between days 14 and 17 by oral gavage. Dosage was calculated based off mean body weights.

Immunological analysis. Lungs were collected on day 18. Lung tissue was minced and digested in RPMI supplemented with FBS, HEPES, and calcium chloride containing 300 U/mL collagenase and 50 U/mL DNase for 45 minutes at 37° C. After filtration, red blood cells were lysed. Cells were labeled with mixtures of extracellular (CD45, CD3, CD4, CD8, MHCII, CD11b, CD11c, SiglecF, Ly6C) and intracellular (IL10) antibodies in a sequential live staining in 96-well plates in preparation for flow cytometry. Data was captured on a BD FACS Celesta and analyzed using FACSDiva.

Results

Figure 7A:
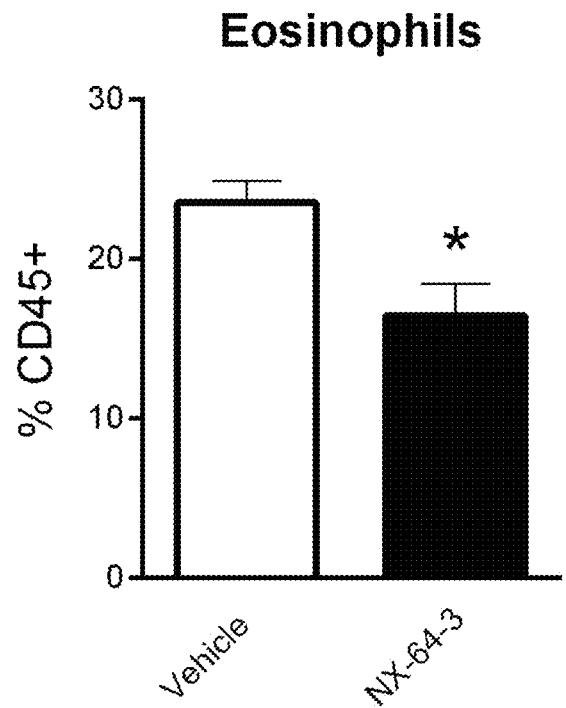
FIGS. 7A-7B. In vivo validation of NX-64-3 efficacy in a model of asthma. Flow cytometry measures of eosinophils (FIG. 7A) and CD4+ IL10+ T cells (FIG. 7B) within the lung on day 18 of an OVA-induced model of experimental asthma in mice treated with vehicle or NX-64-3 (20 mg/kg) daily by oral gavage. Statistical significance ($p<0.05$) is marked by asterisks.
Figure 7B:
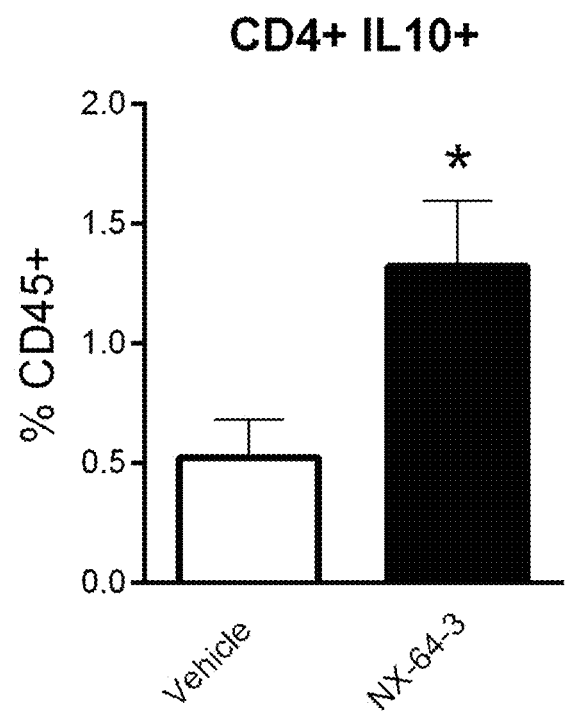

Oral NX-64-3 reduced the percentage of eosinophils (FIG. 7A) within the lung on 15 day 18 and increased the percentage of IL10+CD4+ T cells (FIG. 7B) within the lung on day 18, suggesting the potential for NLRX1 ligands to decrease pulmonary inflammation. We predict similar results with the other compounds defined herein, including NX-64-1, NX-64-2, NX-64-4, NX-64-5, NX-64-6, NX-64-7, NX-64-8, NX-64-9, NX-64-10, NX-64-11, NX-64-12, NX-64-13, NX-64-14, NX-64-15, NX-64-16, NX-64-17, NX-64-18, NX-64-19, NX-64-20, NX-64-21, NX-64-22, NX-64-23, NX-64-24, NX-64-25, NX-64-26, NX-64-27, NX-64-28, NX-64-29, and NX-64-30.

REFERENCES

Abreu, M. T., Toll-like receptor signalling in the intestinal epithelium: how bacterial recognition shapes intestinal function. Nat Rev Immunol, 2010. 10(2): p. 131-144.

Allen, I. C., C. B. Moore, M. Schneider, Y. Lei, B. K. Davis, M. A. Scull, D. Gris, K. E. Roney, A. G. Zimmermann, J. B. Bowzard, P. Ranjan, K. M. Monroe, R. J. Pickles, S. Sambhara, and J. P. Ting, NLRX1 protein attenuates inflammatory responses to infection by interfering with the RIG-I-MAVS and TRAF6-NF-kappaB signaling pathways. Immunity, 2011. 34(6): p. 854-865.

Arnoult, D., F. Soares, I. Tattoli, C. Castanier, D. J. Philpott, and S. E. Girardin, An N-terminal addressing sequence targets NLRX1 to the mitochondrial matrix. J Cell Sci, 2009. 122(Pt 17): p. 3161-3168.

Costford, S. R., I. Tattoli, F. T. Duan, A. Volchuk, A. Klip, D. J. Philpott, M. Woo, and S. E. Girardin, Male Mice Lacking NLRX1 Are Partially Protected From High-Fat Diet-Induced Hyperglycemia. J Endocr Soc, 2018. 2(4): p. 336-347.

Coutermarsh-Ott, S., A. Simmons, V. Capria, T. LeRoith, J. E. Wilson, B. Heid, C. W. Philipson, Q. Qin, R. Hontecillas-Magarzo, J. Bassaganya-Riera, J. P. Ting, N. Dervisis, and I. C. Allen, NLRX1 suppresses tumorigenesis and attenuates histiocytic sarcoma through the negative regulation of NF-kappaB signaling. Oncotarget, 2016. 7(22): p. 33096-33110.

Davis, B. K., C. Philipson, R. Hontecillas, K. Eden, J. Bassaganya-Riera, and FC. Allen, Emerging significance of NLRs in inflammatory bowel disease. Inflamm Bowel Dis, 2014. 20(12): p. 2412-2432.

Eitas, T. K., W. C. Chou, H. Wen, D. Gris, G. R. Robbins, J. Brickey, Y. Oyama, and J. P. Ting, The nucleotide-binding leucine-rich repeat (NLR) family member NLRX1 mediates protection against experimental autoimmune encephalomyelitis and represses macrophage/microglia-induced inflammation. J Biol Chem, 2014. 289 (7): p. 4173-4179.

Feng, H., E. M. Lenarcic, D. Yamane, E. Wauthier, J. Mo, H. Guo, D. R. McGivern, O. Gonzalez-Lopez, I. Misumi, L. M. Reid, J. K. Whitmire, J. P. Ting, J. A. Duncan, N. J. Moorman, and S. M. Lemon, NLRX1 promotes immediate IRF1-directed antiviral responses by limiting dsRNA-activated translational inhibition mediated by PKR. Nat Immunol, 2017. 18(12): p. 1299-1309.

Guo, H., R. Konig, M. Deng, M. Riess, J. Mo, L. Zhang, A. Petrucelli, S. M. Yoh, M. Barefoot, M. Samo, G. D. Sempowski, A. Zhang, A. M. Colberg-Poley, H. Feng, S. M. Lemon, Y. Liu, Y. Zhang, H. Wen, Z. Zhang, B. Damania, L. C. Tsao, Q. Wang, L. Su, J. A. Duncan, S. K. Chanda, and J. P. Ting, NLRX1 Sequesters STING to Negatively Regulate the Interferon Response, Thereby Facilitating the Replication of HIV-1 and DNA Viruses. Cell Host Microbe, 2016. 19(4): p. 515-528.

Hong, M., S. I. Yoon, and I. A. Wilson, Structure and functional characterization of the RNA-binding element of the NLRX1 innate immune modulator. Immunity, 2012. 36(3): p. 337-347.

Jaworska, J., F. Coulombe, J. Downey, F. Tzelepis, K. Shalaby, I. Tattoli, J. Berube, S. Rousseau, J. G. Martin, S. E. Girardin, J. A. McCullers, and M. Divangahi, NLRX1 prevents mitochondrial induced apoptosis and enhances macrophage antiviral immunity by interacting with influenza virus PB1-F2 protein. Proc Natl Acad Sci USA, 2014. 111(20): p. E2110-2119.

Kale, S. D., T. Ayubi, D. Chung, N. Tubau-Juni, A. Leber, H. X. Dang, S. Karyala, R. Hontecillas, C. B. Lawrence, R. A. Cramer, and J. Bassaganya-Riera, Modulation of Immune Signaling and Metabolism Highlights Host and Fungal Transcriptional Responses in Mouse Models of Invasive Pulmonary Aspergillosis. Sci Rep, 2017. 7(1): p. 17096.

Kang, M. J., C. M. Yoon, B. H. Kim, C. M. Lee, Y. Zhou, M. Sauler, R. Homer, A. Dhamija, D. Boffa, A. P. West, G. S. Shadel, J. P. Ting, J. R. Tedrow, N. Kaminski, W. J. Kim, C. G. Lee, Y. M. Oh, and J. A. Elias, Suppression of NLRX1 in chronic obstructive pulmonary disease. J Clin Invest, 2015. 125(6): p. 2458-2462.

Kim, J. H., ME. Park, C. Nikapitiya, T. H. Kim, M B. Uddin, H. C. Lee, E. Kim, J. Y. Ma, J. U. Jung, C. J. Kim, and J. S. Lee, FAS-associated factor-1 positively regulates type I interferon response to RNA virus infection by targeting NLRX1. PLoS Pathog, 2017. 13(5): p. e1006398.

Koblansky, A. A., A. D. Truax, R. Liu, S. A. Montgomery, S. Ding, J. E. Wilson, W. J. Brickey, M. Muhlbauer, R. M. McFadden, P. Hu, Z. Li, C. Jobin, P. K. Lund, and J. P. Ting, The Innate Immune Receptor NLRX1 Functions as a Tumor Suppressor by Reducing Colon Tumorigenesis and Key Tumor-Promoting Signals. Cell Rep, 2016. 14(11): p. 2562-2575.

Kors, L., E. Rampanelli, G. Stokman, L. M. Butter, N. M. Held, N. Claessen, P. W. B. Larsen, J. Verheij, C. J. Zuurbier, G. Liebisch, G. Schmitz, S. E. Girardin, S. Florquin, R. H. Houtkooper, and J. C. Leemans, Deletion of NLRX1 increases fatty acid metabolism and prevents diet-induced hepatic steatosis and metabolic syndrome. Biochim Biophys Acta, 2018. 1864(5 Pt A): p. 1883-1895.

Leber, A., R. Hontecillas, N. Tubau-Juni, V. Zoccoli-Rodriguez, M. Hulver, R. McMillan, K. Eden, I. C. Allen, and J. Bassaganya-Riera, NLRX1 Regulates Effector and Metabolic Functions of CD4+ T Cells. J Immunol, 2017.

Leber, A., R. Hontecillas, N. Tubau-Juni, V. Zoccoli-Rodriguez, V. Abedi, and J. Bassaganya-Riera, NLRX1 Modulates Immunometabolic Mechanisms Controlling the Host-Gut Microbiota Interactions during Inflammatory Bowel Disease. Front Immunol, 2018. 9: p. 363.

Lei, Y., B. A. Kansy, J. Li, L. Cong, Y. Liu, S. Trivedi, H. Wen, J. P. Ting, H. Ouyang, and R. L. Ferris, EGFR-targeted mAb therapy modulates autophagy in head and neck squamous cell carcinoma through NLRX1-TUFM protein complex. Oncogene, 2016. 35(36): p. 4698-4707.

Li, H., S. Zhang, F. Li, and L. Qin, NLRX1 attenuates apoptosis and inflammatory responses in myocardial ischemia by inhibiting MAVS-dependent NLRP3 inflammasome activation. Mol Immunol, 2016. 76: p. 90-97.

Lu, P., R. Hontecillas, V. Abedi, S. Kale, A. Leber, C. Heltzel, M. Langowski, V. Godfrey, C. Philipson, N. Tubau-Juni, A. Carbo, S. Girardin, A. Uren, and J. Bassaganya-Riera, Modeling-Enabled Characterization of Novel NLRX1 Ligands. PLoS One, 2015. 10(12): p. e0145420.

Ma, Z., S. E. Hopcraft, F. Yang, A. Petrucelli, H. Guo, J. P. Ting, D. P. Dittmer, and B. Damania, NLRX1 negatively modulates type I IFN to facilitate KSHV reactivation from latency. PLoS Pathog, 2017. 13(5): p. e1006350.

Moore, C. B., D. T. Bergstralh, J. A. Duncan, Y. Lei, T. E. Morrison, A. G. Zimmermann, M. A. Accavitti-Loper, V. J. Madden, L. Sun, Z. Ye, J. D. Lich, M. T. Heise, Z. Chen, and J. P. Ting, NLRX1 is a regulator of mitochondrial antiviral immunity. Nature, 2008. 451(7178): p. 573-577.

Philipson, C. W., J. Bassaganya-Riera, M. Viladomiu, B. Kronsteiner, V. Abedi, S. Hoops, P. Michalak, L. Kang, S. E. Girardin, and R. Hontecillas, Modeling the Regulatory Mechanisms by Which NLRX1 Modulates Innate Immune Responses to *Helicobacter pylori* Infection. PLoS One, 2015. 10(9): p. e0137839.

Singh, K., A. Poteryakhina, A. Zheltukhin, K. Bhatelia, P. Prajapati, L. Sripada, D. Tomar, R. Singh, A. K. Singh, P. M. Chumakov, and R. Singh, NLRX1 acts as tumor suppressor by regulating TNF-alpha induced apoptosis and metabolism in cancer cells. Biochim Biophys Acta, 2015. 1853(5): p. 1073-1086.

Soares, F., I. Tattoli, M. A. Rahman, S. J. Robertson, A. Belcheva, D. Liu, C. Streutker, S. Winer, D. A. Winer, A. Martin, D. J. Philpott, D. Arnoult, and S. E. Girardin, The mitochondrial protein NLRX1 controls the balance between extrinsic and intrinsic apoptosis. J Biol Chem, 2014. 289(28): p. 19317-19330.

Tattoli, I., S. A. Killackey, E. G. Foerster, R. Molinaro, C. Maisonneuve, M. A. Rahman, S. Winer, D. A. Winer, C. J. Streutker, D. J. Philpott, and S. E. Girardin, NLRX1 Acts as an Epithelial-Intrinsic Tumor Suppressor through the Modulation of TNF-Mediated Proliferation. Cell Rep, 2016. 14(11): p. 2576-2586.

Theus, M. H., T. Brickler, A. L. Meza, S. Coutermarsh-Ott, A. Hazy, D. Gris, and I. C. Allen, Loss of NLRX1 Exacerbates Neural Tissue Damage and NF-kappaB Signaling following Brain Injury. J Immunol, 2017. 199(10): p. 3547-3558.

Qin, Y., B. Xue, C. Liu, X. Wang, R. Tian, Q. Xie, M. Guo, G. Li, D. Yang, and H. Zhu, NLRX1 mediates MAVS degradation to attenuate hepatitis C virus-induced innate immune response through PCBP2. J Virol, 2017.

Wang, Y. G., W. L. Fang, J. Wei, T. Wang, N. Wang, J. L. Ma, and M. Shi, The involvement of NLRX1 and NLRP3 in the development of nonalcoholic steatohepatitis in mice. J Chin Med Assoc, 2013. 76(12): p. 686-692.

EXEMPLARY EMBODIMENTS OF THE INVENTION

1. A compound of Formula (I) having an A ring, a B ring, a C ring, a D ring, and an E ring:

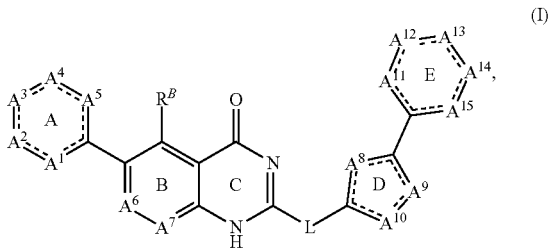

or a salt or ester thereof, wherein:

$A^1$ and $A^5$ are each independently O, $N(R^A)$, $N(R^{ALK})$, $C(R^A)_2$, $C(R^A)$, or N;

$A^2$, $A^3$, and $A^4$ are each independently O, $N(R^A)$, $N(R^{ALK})$, $C(R^A)_2$, $C(R^A)$, N, $C(R^A)(R^O)$, $C(R^O)$, or C(=O), with the proviso that $A^4$ is optionally absent;

$A^6$ and $A^7$ are each independently $C(R^A)$ or N;

$A^8$, $A^9$, and $A^{10}$ are each independently O, $N(R^A)$, $N(R^{ALK})$, $C(R^A)_2$, $C(R^A)$, or N;

$A^{11}$, $A^{12}$, $A^{13}$, $A^{14}$, and $A^{15}$ are each independently O, $N(R^A)$, $N(R^{ALK})$, $C(R^A)_2$, $C(R^A)$, N, $C(R^A)(R^O)$, $C(R^O)$, or C(=O), with the proviso that $A^{14}$ is optionally absent;

each - - - between adjacent atoms represents a bond that is present or absent;

L is O, $N(R^L)$, or $C(R^L)_2$;

$R^O$ in each instance is independently hydroxyl or optionally substituted alkyloxy;

$R^{ALK}$ in each instance is independently C1-C6 alkyl;

$R^A$, $R^B$, and $R^L$ in each instance is independently, hydrogen, halogen, optionally substituted alkyl, optionally substituted alkenyl, optionally substituted alkynyl, optionally substituted cycloalkyl, optionally substituted cycloalkenyl, hydroxyl, carboxyl, optionally substituted alkyloxy, optionally substituted alkenyloxy, optionally substituted alkynyloxy, optionally substituted cycloalkyloxy, optionally substituted cycloalkenyloxy, mercapto, optionally substituted alkylthio, optionally substituted alkenylthio, optionally substituted alkynylthio, optionally substituted alkylsulfinyl, optionally substituted alkylsulfonyl, optionally substituted alkylsulfonyloxy, optionally substituted cycloalkylthio, optionally substituted cycloalkylsulfinyl, optionally substituted cycloalkylsulfonyl, optionally substituted cycloalkylsulfonyloxy, optionally substituted cycloalkenylthio, optionally substituted cycloalkenylsulfinyl, optionally substituted cycloalkenylsulfonyl, optionally substituted cycloalkenylsulfonyloxy, optionally substituted amino, acyl, optionally substituted alkyloxycarbonyl, optionally substituted alkenyloxycarbonyl, optionally substituted alkynyloxycarbonyl, optionally substituted aryloxy carbonyl, optionally substituted carbamoyl, optionally substituted sulfamoyl, cyano, nitro, optionally substituted aryl, optionally substituted aryloxy, optionally substituted arylthio, optionally substituted arylsulfinyl, optionally substituted arylsulfonyl, optionally substituted arylsulfonyloxy, optionally substituted heteroaryl, optionally substituted heteroaryloxy, optionally substituted heteroarylthio, optionally substituted heteroarylsulfinyl, optionally substituted heteroarylsulfonyl, optionally substituted heteroarylsulfonyloxy, or an optionally substituted non-aromatic heterocyclic group.

2. The compound of embodiment 1, wherein at least one of $A^1$, $A^2$, $A^3$, $A^4$, and $A^5$ is O, $N(R^A)$, $N(R^{ALK})$, or N.

3. The compound of embodiment 1, wherein at least one of $A^1$, $A^2$, and $A^3$ is O, $N(R^A)$, $N(R^{ALK})$, or N.

4. The compound of embodiment 1, wherein at least one of $A^1$, $A^2$, and $A^3$ is N.

5. The compound of embodiment 1, wherein $A^2$ is O, $N(R^A)$, $N(R^{ALK})$, or N.

6. The compound of embodiment 1, wherein $A^2$ is N.

7. The compound of any one of embodiments 1 and 6, wherein $A^3$ is O, $N(R^A)$, $N(R^{ALK})$, N, $C(R^O)$, or C(=O).

8. The compound of embodiment 1, wherein:

$A^4$ is present; $A^1$ and $A^5$ are each independently $C(R^A)$ or N; and $A^2$, $A^3$, and $A^4$ are each independently $C(R^A)$, N, or $C(R^O)$; or $A^4$ is absent and $A^1$, $A^2$, $A^3$, and $A^5$ are each independently O, $N(R^A)$, $N(R^{ALK})$, $C(R^A)$, or N, with the proviso that exactly one of $A^1$, $A^2$, $A^3$, and $A^5$ is O, $N(R^A)$, or $N(R^{ALK})$.

9. The compound of embodiment 8, wherein $A^2$ is N.

10. The compound of any one of embodiments 8-9, wherein $A^3$ is $C(R^O)$, O, $N(R^A)$, or $N(R^{ALK})$.

11. The compound of any one of embodiments 8-10, wherein $A^3$ is $C(R^O)$ or $N(R^{ALK})$.

12. The compound of embodiment 1, wherein $A^4$ is present; $A^1$ and $A^5$ are each independently $C(R^A)$ or N; and $A^2$, $A^3$, and $A^4$ are each independently $C(R^A)$, N, or $C(R^O)$.

13. The compound of embodiment 12, wherein $A^2$ is N.

14. The compound of any one of embodiments 12-13, wherein $A^3$ is $C(R^O)$.

15. The compound of embodiment 14, wherein the $R^O$ of $A^3$ is hydroxyl.

16. The compound of any one of embodiments 12-15, wherein $A^1$, $A^4$, and $A^5$ are each $C(R^4)$.

17. The compound of embodiment 1, wherein $A^4$ is absent and $A^1$, $A^2$, $A^3$, and $A^5$ are each independently O, $N(R^4)$, $N(R^{ALK})$, $C(R^4)$, or N, with the proviso that exactly one of $A^1$, $A^2$, $A^3$, and $A^5$ is O, $N(R^4)$, or $N(R^{ALK})$.

18. The compound of embodiment 17, wherein $A^2$ is N.

19. The compound of any one of embodiments 17-18, wherein $A^3$ is O, $N(R^4)$ or $N(R^{ALK})$.

20. The compound of any one of embodiments 17-19, wherein $A^3$ is $N(R^4)$ or $N(R^{ALK})$.

21. The compound of any one of embodiments 17-20, wherein $A^1$ and $A^5$ are each $C(R^4)$.

22. The compound of any one of embodiments 1-21, wherein each $R^4$ of each of $A^1$, $A^2$, $A^3$, $A^4$, and $A^5$, if present, is in each instance independently hydrogen or halogen.

23. The compound of embodiment 1, wherein the A ring is:

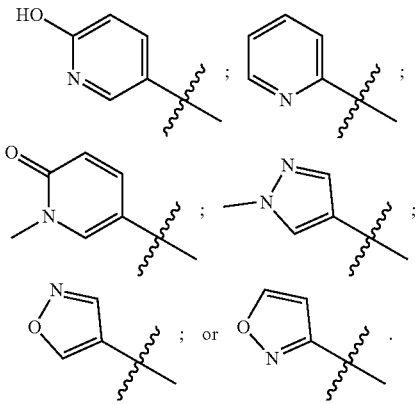

24. The compound of any one of embodiments 1-23, wherein one or both of $A^6$ and $A^7$ is $C(R^4)$.

25. The compound of any one of embodiments 1-24, wherein $R^B$ and the $R^4$ of $A^6$ and $A^7$, if present, are in each instance independently hydrogen or halogen.

26. The compound of any one of embodiments 1-23, wherein the B and the C rings together are:

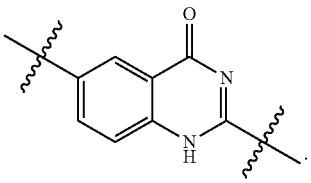 [SMILES: *c1ccc2[nH]c(*)nc(=O)c2c1]

27. The compound of any one of embodiments 1-26, wherein L is $C(R^L)_2$.

28. The compound of embodiment 27 wherein each $R^L$ is independently hydrogen, halogen, or unsubstituted C1-C6 alkyl.

29. The compound of any one of embodiments 1-28, wherein $A^{10}$ is O, N, or NH.

30. The compound of any one of embodiments 1-29, wherein each $R^4$ of $A^8$, $A^9$, and $A^{10}$, if present, is in each instance independently hydrogen or halogen.

31. The compound of any one of embodiments 1-28, wherein the D ring is:

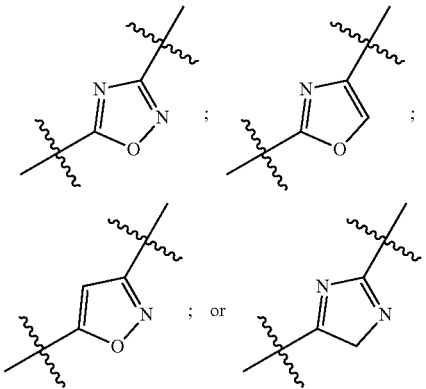

32. The compound of any one of embodiments 1-31, wherein $A^{15}$ is O, $N(R^4)$, $N(R^{ALK})$, or N.

33. The compound of any one of embodiments 1-32, wherein $A^{12}$ is C(=O).

34. The compound of any one of embodiments 1-32, wherein $A^{14}$ is present.

35. The compound of embodiment 34, wherein $A^{11}$, $A^{12}$, $A^{13}$, and $A^{14}$ are each independently $C(R^4)_2$ or $C(R^4)$.

36. The compound of embodiment 34, wherein $A^{12}$ is C(=O).

37. The compound of embodiment 36, wherein $A^{11}$, $A^{13}$, and $A^{14}$ are each independently $C(R^4)_2$ or $C(R^4)$.

38. The compound of any one of embodiments 1-32, wherein $A^{14}$ is absent.

39. The compound of embodiment 38, wherein $A^{15}$ is O, $N(R^4)$, or $N(R^{ALK})$.

40. The compound of any one of embodiments 38-39, wherein at least one of $A^{11}$, $A^{12}$, and $A^{13}$ is $C(R^4)_2$ or $C(R^4)$.

41. The compound of any one of embodiments 1-40, wherein each $R^4$ of each of $A^{11}$, $A^{12}$, $A^{13}$, $A^{14}$, and $A^{15}$, if present, is in each instance independently hydrogen or halogen.

42. The compound of any one of embodiments 1-31, wherein the E ring is:

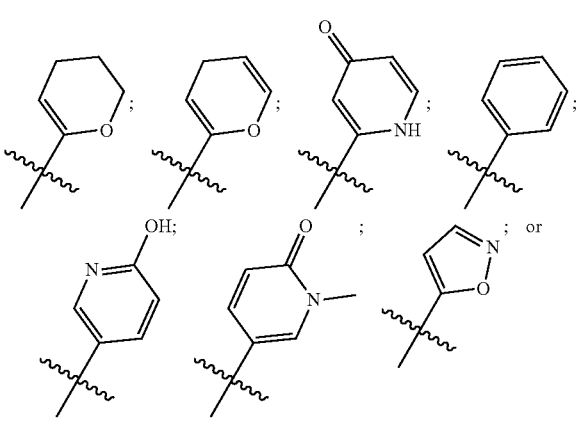

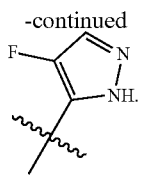

43. The compound of any one of embodiments 1-42, wherein R, R, and $R^L$ in each instance are independently hydrogen, halogen, optionally substituted C1-C6 alkyl, hydroxyl, carboxyl, optionally substituted cycloalkyl, optionally substituted C1-C6 alkyloxy, optionally substituted amino, acyl, optionally substituted alkyloxycarbonyl, optionally substituted aryl, optionally substituted heteroaryl, or optionally substituted non-aromatic heterocyclic group.

44. The compound of any one of embodiments 1-42, wherein $R^A$, $R^B$, and $R^L$ in each instance are independently hydrogen, halogen, unsubstituted C1-C6 alkyl, hydroxyl, carboxyl, unsubstituted cycloalkyl, unsubstituted C1-C6 alkyloxy, unsubstituted amino, acyl, unsubstituted alkyloxycarbonyl, unsubstituted aryl, unsubstituted heteroaryl, or unsubstituted non-aromatic heterocyclic group.

45. The compound of any one of embodiments 1-42, wherein $R^A$, $R^B$, and $R^L$ in each instance are hydrogen or halogen.

46. The compound of any one of embodiments 1-42, wherein $R^A$, $R^B$, and $R^L$ in each instance are hydrogen.

47. The compound of embodiment 1, wherein the compound is any one of NX-64-1, NX-64-2, NX-64-3, NX-64-4, NX-64-5, NX-64-6, NX-64-7, NX-64-8, NX-64-9, NX-64-10, NX-64-11, NX-64-12, NX-64-13, NX-64-14, NX-64-15, NX-64-16, NX-64-17, NX-64-18, NX-64-19, NX-64-20, NX-64-21, NX-64-22, NX-64-23, NX-64-24, NX-64-25, NX-64-26, NX-64-27, NX-64-28, NX-64-29, and NX-64-30, or a salt or ester thereof.

48. A method of treating a condition in an animal with a compound as recited in any one of embodiments 1-47, the method comprising administering an effective amount of the compound to the animal, wherein the condition is selected from the group consisting of an autoimmune disease, an allergic disease, a chronic and/or inflammatory central nervous system disease, a chronic and/or inflammatory respiratory disease, cancer, and an infectious disease.

49. The method of embodiment 48, wherein the condition is an autoimmune disease and the autoimmune disease comprises multiple sclerosis.

50. The method of embodiment 49, wherein the multiple sclerosis comprises a relapsing-remitting form of multiple sclerosis.

51. The method of embodiment 49, wherein the multiple sclerosis comprises a secondary progressive form of multiple sclerosis.

52. The method of embodiment 49, wherein the multiple sclerosis comprises a primary progressive form of multiple sclerosis.

53. The method of embodiment 48, wherein the condition is an allergic disease and the allergic disease comprises asthma.

54. The method of embodiment 48, wherein the condition is a chronic and/or inflammatory central nervous system disease and the chronic and/or inflammatory central nervous system disease comprises Alzheimer's disease.

55. The method of embodiment 48, wherein the condition is a chronic and/or inflammatory central nervous system disease and the chronic and/or inflammatory central nervous system disease comprises Parkinson's disease.

56. The method of embodiment 48, wherein the condition is a chronic and/or inflammatory central nervous system disease and the chronic and/or inflammatory central nervous system disease comprises neuroinflammation resulting from stroke, traumatic brain injury, or spinal cord injury.

57. The method of embodiment 48, wherein the condition is a chronic and/or inflammatory respiratory disease and the chronic and/or inflammatory respiratory disease comprises chronic obstructive pulmonary disease.

58. The method of embodiment 48, wherein the condition is a chronic and/or inflammatory respiratory disease and the chronic and/or inflammatory respiratory disease comprises idiopathic pulmonary fibrosis.

59. The method of embodiment 48, wherein the condition is an autoimmune disease and the autoimmune disease comprises inflammatory bowel disease.

What is claimed is:

1. A compound of Formula (I) having an A ring, a B ring, a C ring, a D ring, and an E ring:

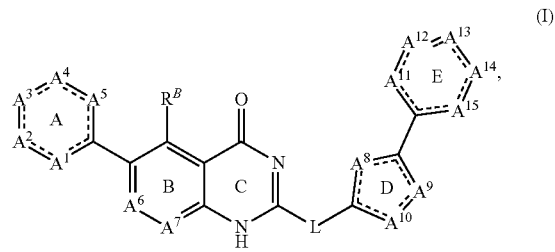

(I)

or a salt or ester thereof, wherein:
$A^1$ and $A^5$ are each independently O, $N(R^A)$, $N(R^{ALK})$, $C(R^A)_2$, $C(R^A)$, or N;
$A^2$, $A^3$, and $A^4$ are each independently O, $N(R^A)$, $N(R^{ALK})$, $C(R^A)_2$, $C(R^A)$, N, $C(R^A)(R^O)$, $C(R^O)$, or $C(=O)$, with the proviso that $A^4$ is optionally absent;
$A^6$ and $A^7$ are each independently $C(R^A)$ or N;
$A^8$, $A^9$, and $A^{10}$ are each independently O, $N(R^A)$, $N(R^{ALK})$, $C(R^A)_2$, $C(R^A)$, or N;
$A^{11}$, $A^{12}$, $A^{13}$, $A^{14}$, and $A^{15}$ are each independently O, $N(R^A)$, $N(R^{ALK})$, $C(R^A)_2$, $C(R^A)$, N, $C(R^A)(R^O)$, $C(R^O)$, or $C(=O)$, with the proviso that $A^{14}$ is optionally absent;
each - - - between adjacent atoms represents a bond that is present or absent;
L is O, $N(R^L)$, or $C(R^L)_2$;
$R^O$ in each instance is independently hydroxyl or optionally substituted alkyloxy;
$R^{ALK}$ in each instance is independently C1-C6 alkyl;
$R^A$, $R^B$, and $R^L$ in each instance is independently, hydrogen, halogen, optionally substituted alkyl, optionally substituted alkenyl, optionally substituted alkynyl, optionally substituted cycloalkyl, optionally substituted cycloalkenyl, hydroxyl, carboxyl, optionally substituted alkyloxy, optionally substituted alkenyloxy, optionally substituted alkynyloxy, optionally substituted cycloalkyloxy, optionally substituted cycloalkenyloxy, mercapto, optionally substituted alkylthio, optionally substituted alkenylthio, optionally substituted alkynylthio, optionally substituted alkylsulfinyl, optionally substituted alkylsulfonyl, optionally substituted alkylsulfonyloxy, optionally substituted cycloalkylthio, optionally substituted cycloalkylsulfinyl, optionally substituted cycloalkylsulfonyl, optionally substituted cycloalkylsulfonyloxy, optionally substituted cycloalkenylthio, optionally substituted cycloalkenylsulfinyl, optionally substituted cycloalkenylsulfonyl, optionally substituted cycloalkenylsulfonyloxy, optionally substituted amino, acyl, optionally substituted alkyloxycarbonyl, optionally substituted alkenyloxycarbonyl, optionally substituted alkynyloxycarbonyl, optionally substituted aryloxycarbonyl, optionally substituted carbamoyl, optionally substituted sulfamoyl, cyano, nitro, optionally substituted aryl, optionally substituted aryloxy, optionally substituted arylthio, optionally substituted arylsulfinyl, optionally substituted arylsulfonyl, optionally substituted arylsulfonyloxy, optionally substituted heteroaryl, optionally substituted heteroaryloxy, optionally substituted heteroarylthio, optionally substituted heteroarylsulfinyl, optionally substituted heteroarylsulfonyl, optionally substituted heteroarylsulfonyloxy, or an optionally substituted non-aromatic heterocyclic group.

2. The compound of claim 1, wherein $A^2$ is N.

3. The compound of claim 1, wherein $A^3$ is O, N($R^A$), N($R^{ALK}$), N, C($R^O$), or C(=O).

4. The compound of claim 1, wherein:
$A^4$ is present; $A^1$ and $A^5$ are each independently C($R^A$) or N; and $A^2$, $A^3$, and $A^4$ are each independently C($R^A$), N, or C($R^O$); or
$A^4$ is absent and $A^1$, $A^2$, $A^3$, and $A^5$ are each independently O, N($R^A$), N($R^{ALK}$), C($R^A$), or N, with the proviso that exactly one of $A^1$, $A^2$, $A^3$, and $A^5$ is O, N($R^A$), or N($R^{ALK}$).

5. The compound of claim 4, wherein $A^2$ is N.

6. The compound of claim 4, wherein $A^3$ is C($R^O$), O, N($R^A$), or N($R^{ALK}$).

7. The compound of claim 1, wherein $A^4$ is present; $A^1$ and $A^5$ are each independently C($R^A$) or N; and $A^2$, $A^3$, and $A^4$ are each independently C($R^A$), N, or C($R^O$).

8. The compound of claim 7, wherein $A^2$ is N.

9. The compound of claim 8, wherein $A^3$ is C($R^O$).

10. The compound of claim 9, wherein the $R^O$ of $A^3$ is hydroxyl.

11. The compound of claim 10, wherein $A^1$, $A^4$, and $A^5$ are each C($R^A$).

12. The compound of claim 1, wherein $A^4$ is absent and $A^1$, $A^2$, $A^3$, and $A^5$ are each independently O, N($R^A$), N($R^{ALK}$), C($R^A$), or N, with the proviso that exactly one of $A^1$, $A^2$, $A^3$, and $A^5$ is O, N($R^A$), or N($R^{ALK}$).

13. The compound of claim 12, wherein $A^2$ is N.

14. The compound of claim 13, wherein $A^3$ is O, N($R^A$) or N($R^{ALK}$).

15. The compound of claim 14, wherein $A^1$ and $A^5$ are each C($R^A$).

16. The compound of claim 1, wherein the A ring is:

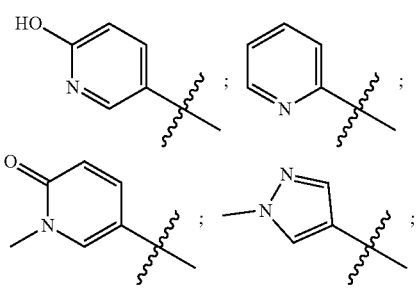

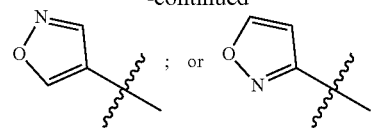

17. The compound of claim 1, wherein $A^{10}$ is O, N, or NH.

18. The compound of claim 1, wherein the D ring is:

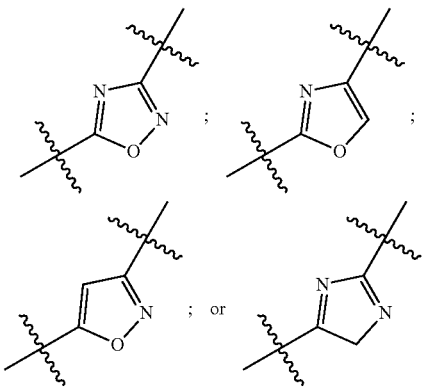

19. The compound of claim 1, wherein $A^{15}$ is O, N($R^A$), N($R^{ALK}$), or N.

20. The compound of claim 19, wherein $A^{12}$ is C(=O).

21. The compound of claim 19, wherein $A^{14}$ is present.

22. The compound of claim 19, wherein $A^{14}$ is absent.

23. The compound of claim 1, wherein the E ring is:

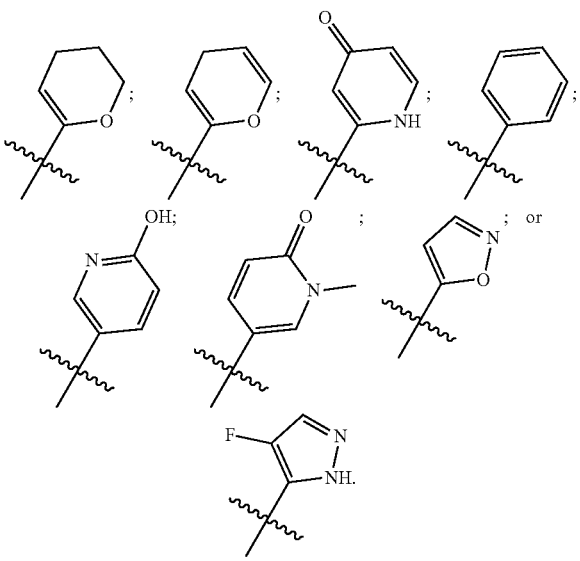

24. The compound of claim 1, wherein $R^A$, $R^B$, and $R^L$ in each instance are independently hydrogen, halogen, unsubstituted C1-C6 alkyl, hydroxyl, carboxyl, unsubstituted cycloalkyl, unsubstituted C1-C6 alkyloxy, unsubstituted amino, acyl, unsubstituted alkyloxycarbonyl, unsubstituted aryl, unsubstituted heteroaryl, or unsubstituted non-aromatic heterocyclic group.

25. The compound of claim 1, wherein $R^A$, $R^B$, and $R^L$ in each instance are hydrogen or halogen.

26. The compound of claim 1, wherein $R^A$, $R^B$, and $R^L$ in each instance are hydrogen.
27. The compound of claim 1, wherein the compound is any one of:
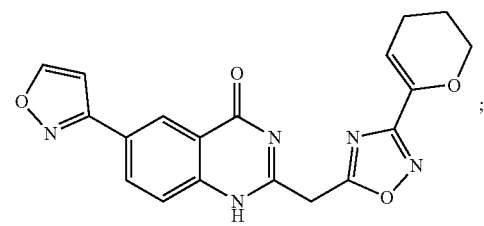;
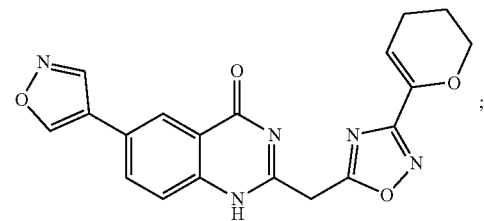;
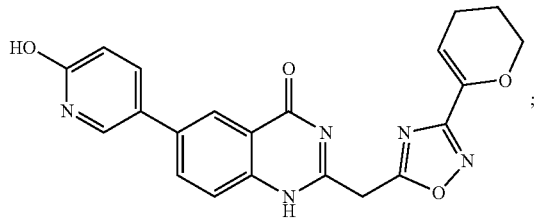;
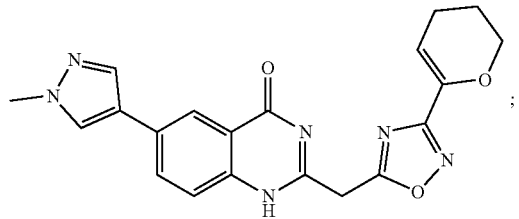;
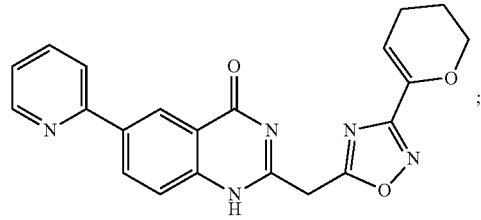;
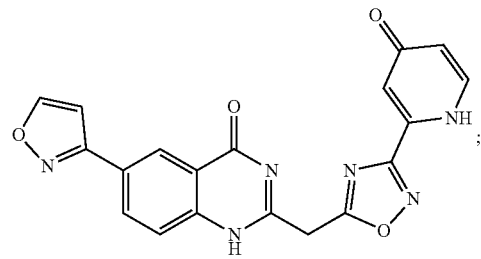;
-continued
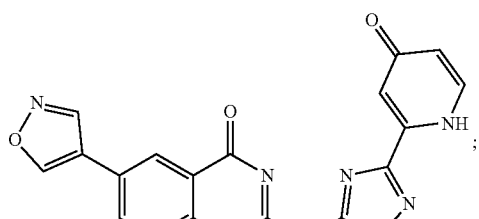;
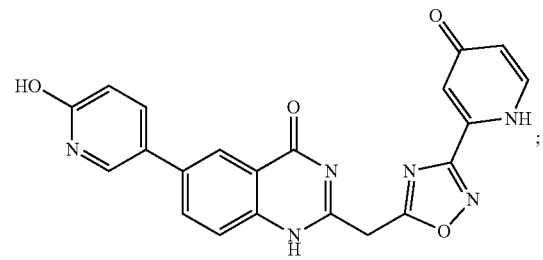;
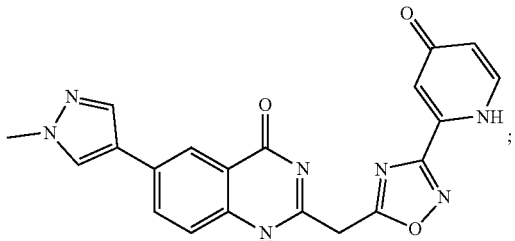;
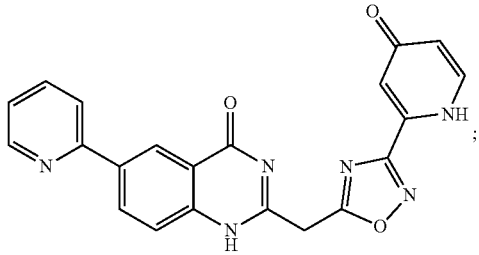;
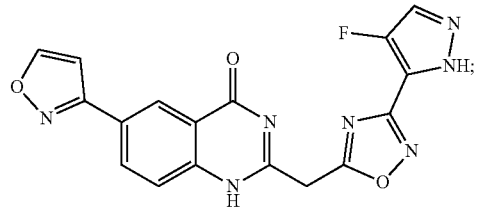;
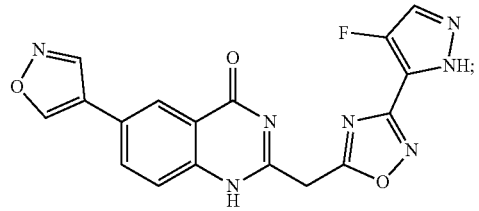;
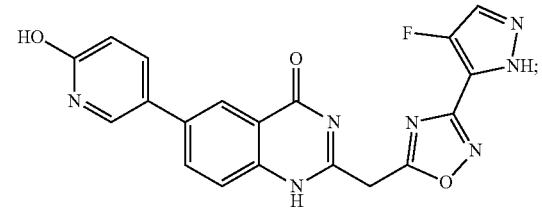;

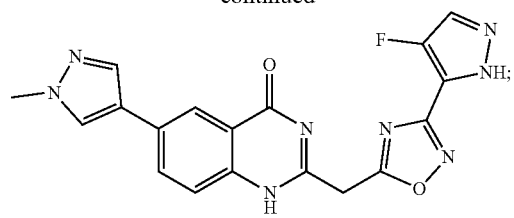
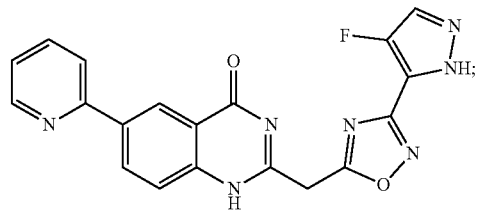
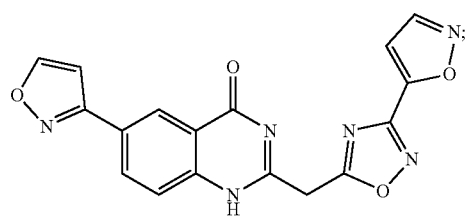
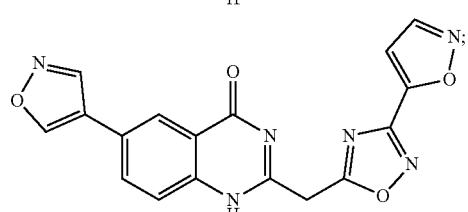
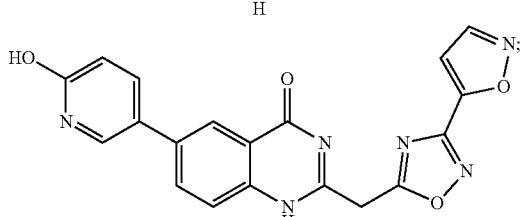
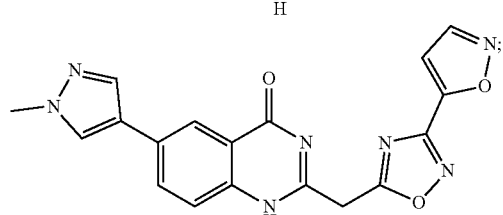
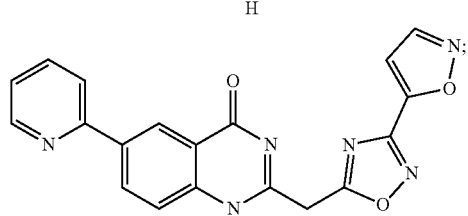
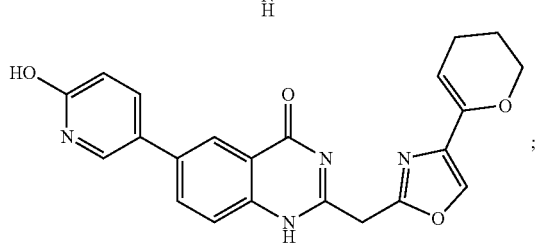
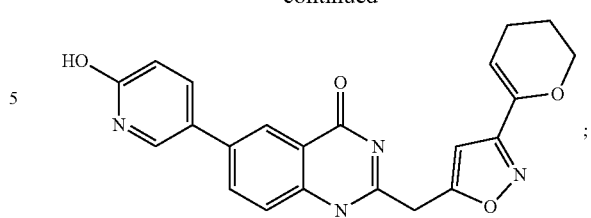
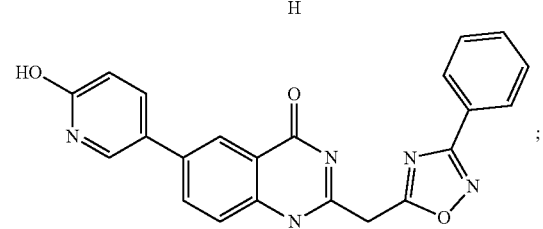
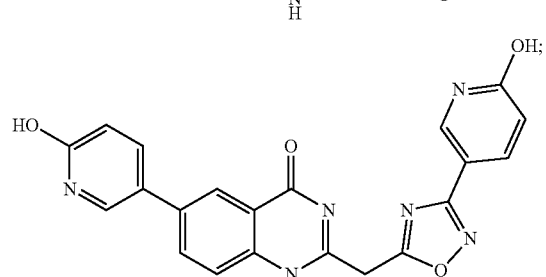
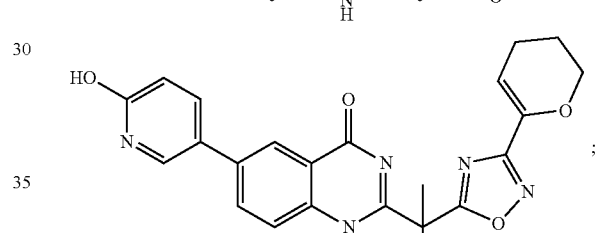
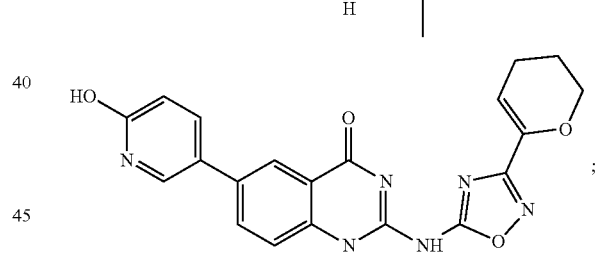
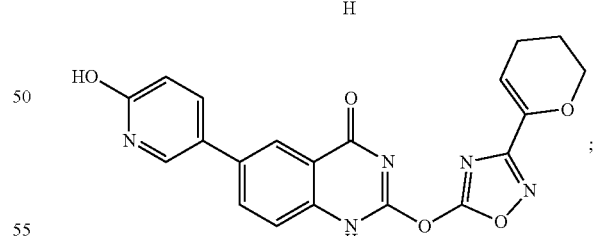
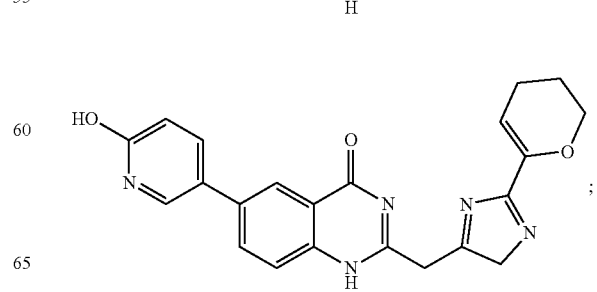

-continued

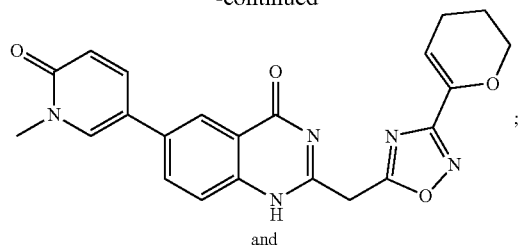

and

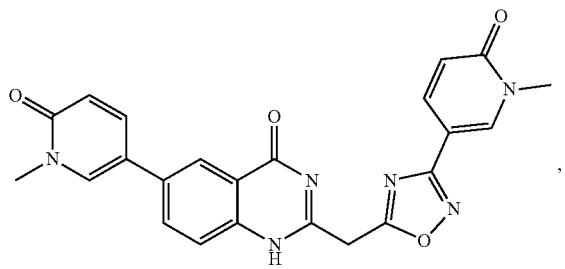

or a salt or ester thereof.

28. The compound of claim 1, wherein the compound is any one of:

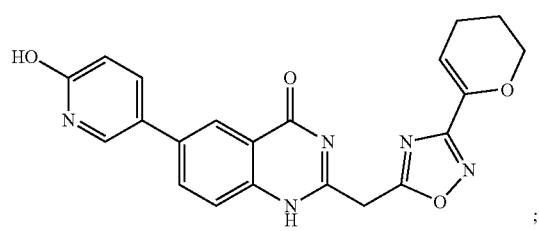

-continued

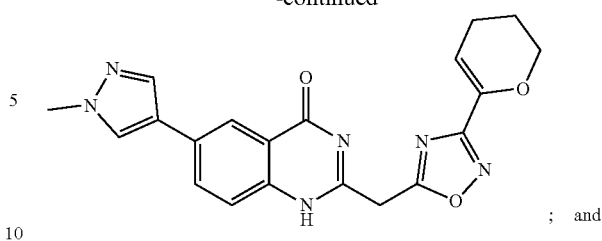

; and

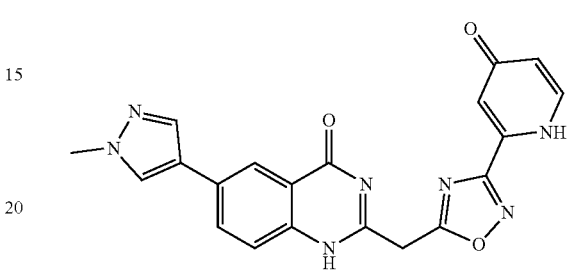

, or a salt or ester thereof.

29. A method of ameliorating or reducing a symptom of a condition in which NLRX1 is implicated in an animal with a compound as recited in claim 1, the method comprising administering an effective amount of the compound to the animal, wherein the condition is multiple sclerosis, asthma, Alzheimer's disease, Parkinson's disease, neuroinflammation, chronic obstructive pulmonary disease, idiopathic pulmonary fibrosis, or inflammatory bowel disease.

* * * * *